(12) United States Patent
Ludowise

(10) Patent No.: US 9,938,569 B2
(45) Date of Patent: Apr. 10, 2018

(54) COMPENSATION FOR SPECTRAL CROSSTALK IN MULTIPLEX NUCLEIC ACID AMPLIFICATION

(75) Inventor: Peter D. Ludowise, St. Paul, MN (US)

(73) Assignee: DIASORIN S.P.A., Vercelli (IT)

( * ) Notice: Subject to any disclaimer, the term of this patent is extended or adjusted under 35 U.S.C. 154(b) by 791 days.

(21) Appl. No.: 13/394,944

(22) PCT Filed: Aug. 31, 2010

(86) PCT No.: PCT/US2010/047265
§ 371 (c)(1),
(2), (4) Date: Mar. 8, 2012

(87) PCT Pub. No.: WO2011/031585
PCT Pub. Date: Mar. 17, 2011

(65) Prior Publication Data
US 2012/0171677 A1    Jul. 5, 2012

Related U.S. Application Data

(60) Provisional application No. 61/358,287, filed on Jun. 24, 2010, provisional application No. 61/241,307, filed on Sep. 10, 2009.

(51) Int. Cl.
*G01N 33/48* (2006.01)
*G01N 33/50* (2006.01)
(Continued)

(52) U.S. Cl.
CPC .......... *C12Q 1/6851* (2013.01); *G06F 19/18* (2013.01); *G06F 19/20* (2013.01)

(58) Field of Classification Search
None
See application file for complete search history.

(56) References Cited

U.S. PATENT DOCUMENTS

| 6,156,465 A | 12/2000 | Cao |
| 6,333,501 B1 | 12/2001 | Labrenz |

(Continued)

FOREIGN PATENT DOCUMENTS

| WO | WO 2005-068975 | 7/2005 |
| WO | WO 2006-107619 | 10/2006 |

(Continued)

OTHER PUBLICATIONS

Bagwell, "Fluorescence Spectral Overlap Compensation for Any Number of Flow Cytometry Parameters" Annals of the New York Academy of Sciences, 1993, vol. 677. pp. 167-184.

(Continued)

*Primary Examiner* — Russell S Negin
(74) *Attorney, Agent, or Firm* — Arent Fox LLP

(57) ABSTRACT

A method includes performing a nucleic acid amplification of a nucleic acid sample using a detection probe, wherein the nucleic acid amplification occurs over one or more interrogation periods, and, from the nucleic acid amplification, acquiring amplification data that indicates an amount of nucleic acid present for each of the one or more interrogation periods. The method also includes, based on the amplification data, determining a crosstalk correction value associated with a spectral neighbor to the probe to reduce spectral crosstalk from the spectral neighbor; and applying the crosstalk correction value to amplification data collected from multiplex nucleic acid amplifications of nucleic acid samples.

18 Claims, 33 Drawing Sheets

(51) Int. Cl.
*C12Q 1/68* (2018.01)
*G06F 19/20* (2011.01)
*G06F 19/18* (2011.01)

(56) References Cited

U.S. PATENT DOCUMENTS

| | | |
|---|---|---|
| 6,627,159 B1 | 9/2003 | Bedingham |
| 6,734,401 B2 | 5/2004 | Bedingham |
| 7,023,451 B2 | 4/2006 | Feng |
| 7,177,023 B2 | 2/2007 | Reel |
| 7,435,602 B2 | 10/2008 | Gunstream |
| 2002/0028452 A1 | 3/2002 | Wittwer |
| 2002/0048533 A1 | 4/2002 | Harms |
| 2002/0064885 A1 | 5/2002 | Bedingham |
| 2003/0044826 A1 | 3/2003 | Ward |
| 2004/0259260 A1 | 12/2004 | Gunstream |
| 2006/0038109 A1 | 2/2006 | Kinney |
| 2006/0051796 A1 | 3/2006 | Boell |
| 2006/0223169 A1* | 10/2006 | Bedingham et al. ...... 435/287.2 |
| 2006/0223172 A1 | 10/2006 | Bedingham |
| 2006/0286587 A1 | 12/2006 | Lee |
| 2006/0291706 A1 | 12/2006 | Gunstream |
| 2006/0292571 A1* | 12/2006 | Babiel ................. C12Q 1/6851 435/6.12 |
| 2007/0009382 A1 | 1/2007 | Bedingham |
| 2007/0009383 A1 | 1/2007 | Bedingham |
| 2007/0010007 A1 | 1/2007 | Aysta |
| 2007/0098594 A1 | 5/2007 | Elkin |
| 2007/0100569 A1 | 5/2007 | DeSimas |
| 2007/0113880 A1 | 5/2007 | Atwood |
| 2007/0143385 A1 | 6/2007 | Kurnik |
| 2008/0018898 A1* | 1/2008 | Gunstream et al. .......... 356/416 |
| 2008/0033677 A1 | 2/2008 | Tomaney |
| 2008/0154512 A1 | 6/2008 | Leong |
| 2008/0178653 A1 | 7/2008 | Gunstream |
| 2009/0035779 A1 | 2/2009 | Kurnik |
| 2009/0167639 A1 | 7/2009 | Casner |
| 2009/0218517 A1 | 9/2009 | Bedingham |

FOREIGN PATENT DOCUMENTS

| | | |
|---|---|---|
| WO | WO 2009003645 A1 * | 1/2009 |
| WO | WO 2009-132268 | 10/2009 |

OTHER PUBLICATIONS

Torrence, "A Practical Guide to Wavelet Analysis", Bulletin of the American Meteorological Society, 1997, pp. 61-78.

Daubechies, "The Wavelet Transform, Time-Frequency Localization and Signal Analysis", IEEE Transactions on Information Theory, Sep. 1990, vol. 36, No. 5, pp. 961-1005.

Verwer. BD FACSDiVa Option White Paper, BD Biosciences, 2002, http://www.bdbiosciences.comlecatIdocumentSearch. do?key=verwer&prodCounr-O&charser-ut f-8 &MatchAllTerms=true. past visited Oct. 8, 2010., pp. 1-18.

International Search Report for PCT/US2010/47265, dated Oct. 27, 2010, 2 pages.

Written Opinion for PCT/US2010/47265, dated Oct. 27, 2010, 8 pages.

U.S. Appl. No. 60/260,063, filed Jan. 6, 2001, entitled Sample Processing Devices, Systems and Methods.

U.S. Appl. No. 60/284,637, filed Apr. 18, 2001, entitled Enhanced Sample Processing Devices, Systems and Methods.

* cited by examiner

COMPENSATION FOR SPECTRAL CROSSTALK IN MULTIPLEX NUCLEIC ACID AMPLIFICATION

CROSS REFERENCE TO RELATED APPLICATIONS

This application is a national stage filing under 35 U.S.C. 371 of PCT/US2010/047265, filed Aug. 31, 2010, which claims priority from U.S. Provisional Application Ser. No. 61/358,287 filed Jun. 24, 2010, and U.S. Provisional Application Ser. No. 61/241,307, filed Sep. 10, 2009, the disclosure of which is incorporated by reference in their entirety herein.

TECHNICAL FIELD

The disclosure relates to techniques for nucleic acid amplification and, more particularly, techniques for compensation for spectral crosstalk during detection of target species using fluorescent dyes.

BACKGROUND

Nucleic acid amplification can be used for sequencing, cloning, genetic mapping, and other forms of nucleic acid sequence amplification, or to determine an initial concentration of nucleic acid in a sample by constructing a standard curve of results from samples including known concentrations, or other forms of nucleic acid amplification. Nucleic acid amplification can be used for analyzing nucleic acids including, for example, DNA and RNA. Types of nucleic acid amplification include polymerase chain reaction (PCR), transcription mediated amplification (TMA), ligase chain reaction (LCR), strand-displacement amplification (SDA) and nucleic acid sequence based amplification (NASBA).

In general, PCR relies on the ability of DNA-copying enzymes to remain stable at high temperatures. A single PCR cycle includes three major steps: denaturation, annealing, and extension. During the denaturation, a liquid sample is heated at approximately 94° C. During this process, double DNA strands "melt" open into single stranded DNA and all enzymatic reactions stop. During annealing, the single stranded DNA is cooled to 54° C. At this temperature, primers bind or "anneal" to the ends of the DNA strands. During extension, the sample is heated to 75° C. At this temperature, nucleotides add to the primers and eventually a complementary copy of the DNA template is formed. PCR analyses typically repeat this PCR cycle multiple times (e.g., about 40) to produce a large number of replicate DNA strands.

Real-time PCR can be used to detect a relative amount of nucleic acid present in a sample as the sample undergoes a plurality of PCR interrogation periods (e.g., cycles). For example, the sample may include markers that fluoresce when attached to double-stranded DNA. In this example, fluorescence detected by a detector is proportionate to the number of double-stranded DNA present in the sample. Thus, as PCR proceeds, fluorescence increases.

Transcription-associated amplification embodiments, e.g., nucleic acid sequence based amplification (NASBA) and transcription-mediated amplification (TMA), use substantially isothermal conditions and an RNA polymerase to produce multiple RNA transcripts from a nucleic acid template by using a promoter-primer, a primer, an RNA polymerase, a DNA polymerase, deoxyribonucleoside triphosphates (dNTP), ribonucleoside triphosphates (rNTP), and a promoter-template complementary oligonucleotide, and optionally may also include other oligonucleotides. Assays may use detection probes for amplification of the nucleic acids in the reactions. During the amplification reaction, each detection probe binds to its specific amplicon and is converted to a form that produces a detectable signal (e.g., a hydrolysis-resistant chemiluminescent signal or higher fluorescence intensity than in the unconverted form).

A need continues to exist for analysis and accuracy in the data generated by nucleic acid amplification processes.

SUMMARY

In general, the invention relates to techniques for improving analysis accuracy of data generated by nucleic acid amplification in a system having a fluorescence detection device, such as a system for real-time polymerase chain reaction (PCR) amplification. In particular, the techniques may minimize an effect of spectral signals that may be detected from one dye by an optical module configured to detect spectral signals from a different dye, a phenomenon referred to herein as "spectral crosstalk," or simply "crosstalk."

In one exemplary embodiment, the system may include four optical modules that provide four "channels" for optical detection of four different dyes. A system capable of detecting multiple target species may be referred to as a multiplex system. Each of these four optical modules may be configured to excite different regions of a sample containing amplified nucleic acid at any given time and collect emitted fluorescent light energy at different wavelengths from the dyes. In embodiments including multiple optical modules, multiple, parallel reactions occurring within a sample may be interrogated substantially simultaneously.

Each of the optical modules may be optimized for detection of a respective fluorescent dye at a discrete wavelength band. In other words, the optical modules may be used to interrogate multiple, parallel reactions at different wavelengths. The parallel reactions may, for example, occur within a single process chamber (e.g., well) of a rotating disk. Additionally, each optical module may be removable to change the detection capabilities of the device.

The plurality of optical modules may be optically coupled to a single detector by a multi-legged optical fiber bundle. In this manner, multiplexing can be achieved by using a plurality of optical modules and a single detector, e.g., a photomultiplier tube. The optical components in each optical module may be selected to maximize sensitivity and minimize the amount of spectral crosstalk, i.e., carry-over signals from one dye on an optical module that is configured to detect spectral signals from another dye. The fluorescent dyes can be spectrally spaced closely to one another, and can be differentiated by the use of optical filters to minimize signal carry-over from one dye to another. Due to the wide absorption and emission bands of typical fluorophores, the filters may reduce but not eliminate the spectral crosstalk. The spectral crosstalk of a strongly amplifying signal will often result in a growth on a neighboring channel and may be incorrectly interpreted as a growth on a target channel. This may result in false positive determinations. The techniques described herein use a set of correction factors determined from a calibration procedure to automatically remove the interfering signals.

The techniques described herein may be applied to reduce or eliminate spectral crosstalk in nucleic acid amplification. In an exemplary embodiment, the techniques described herein may be applied to reduce or eliminate spectral crosstalk in real-time multiplex nucleic acid amplification. Spectral crosstalk occurs due to spectral overlap of one fluorescent probe (e.g., dye) onto neighboring detection channels, and can lead to false positive determinations. In accordance with the techniques of this disclosure, a set of crosstalk correction factors is determined from a calibration process. An algorithm is described that employs the set of correction factors to automatically subtract the amount of signal of neighboring channels onto the channel of interest. This may reduce or eliminate false positive determinations.

In one aspect, the disclosure is directed to a method comprising performing a nucleic acid amplification of a nucleic acid sample, wherein the nucleic acid amplification occurs over one or more interrogation periods using a detection probe, and, from the nucleic acid amplification, acquiring amplification data that indicates an amount of nucleic acid present for each of the one or more interrogation periods. The method also includes, based on the amplification data, determining a crosstalk correction value associated with a spectral neighbor to the probe to reduce spectral crosstalk from the spectral neighbor, and applying the crosstalk correction value to amplification data collected from multiplex nucleic acid amplification of nucleic acid samples.

In a preferred embodiment, based on the amplification data, a crosstalk correction value is determined that is associated with a nearest spectral neighbor to the probe to reduce spectral crosstalk from the nearest spectral neighbor; and applying the crosstalk correction value to amplification data collected from multiplex nucleic acid amplification of nucleic acid samples.

Alternatively, the method may use more than one probe to perform nucleic acid amplifications of a nucleic acid sample over one or more interrogation periods, and more than one crosstalk correction value is computed, wherein each crosstalk correction value is associated with a spectral neighbor, such as any spectral neighbor with peak fluorescence of the detection target dye and the neighboring target dye separated by a distance less than a threshold distance. For example, any spectral neighbor with peak fluorescence of the detection target dye and the neighboring target dye separated by a distance less than a threshold distance.

In another aspect, a method comprises performing a multiplex nucleic acid amplification of a nucleic acid sample, wherein the multiplex nucleic acid amplification comprises a plurality of interrogation periods, and, from the nucleic acid amplification, acquiring amplification data that indicates an amount of nucleic acid present for each of the plurality of interrogation periods. The method also comprises applying a crosstalk correction factor to the amplification data to generate modified amplification data in which spectral crosstalk signals from a spectral neighbor are reduced, wherein the crosstalk correction value is derived based on multiplex nucleic acid amplification of a second nucleic acid sample, and displaying the modified amplification data.

In another aspect, a detection system includes a detection device comprising a motor to rotate a disk having a plurality of process chambers each holding a respective sample and one or more fluorescent dyes, a plurality of optical modules, and a housing having a plurality of locations adapted to receive the optical modules. Each of the plurality of optical modules includes an optical channel having a light source selected for a different one of the dyes and a lens to capture fluorescent light emitted from the disk. The system also includes a data acquisition device coupled to the detection device, wherein the data acquisition device is configured to apply a crosstalk correction value for each of the plurality of optical modules to reduce spectral crosstalk associated with a spectral neighbor for that optical module. The crosstalk correction value is derived by performing an analysis based on amplification data from a nucleic acid amplification of a nucleic acid sample using a detection probe, wherein the nucleic acid amplification occurs over a plurality of interrogation periods, and wherein the analysis comprises acquiring the amplification data that indicates an amount of nucleic acid present for each of the plurality of interrogation periods, and determining the crosstalk correction value associated with the spectral neighbor based on the amplification data.

In a preferred embodiment, the crosstalk correction value is derived by performing an analysis based on amplification data from a nucleic acid amplification of a nucleic acid sample using a detection probe, wherein the nucleic acid amplification occurs over a plurality of interrogation periods, and wherein the analysis comprises acquiring the amplification data that indicates an amount of nucleic acid present for each of the plurality of interrogation periods, and determining the crosstalk correction value associated with the spectral neighbor based on the amplification data.

In a further aspect, a detection device includes a motor to rotate a disk having a plurality of process chambers each holding a respective sample and one or more fluorescent dyes, a plurality of optical modules, and a housing having a plurality of locations adapted to receive the optical modules. Each of the optical modules includes an optical channel having a light source selected for a different one of the dyes and a lens to capture fluorescent light emitted from the disk. The device also includes a control unit configured to apply crosstalk correction values for each of the plurality of optical modules to reduce spectral crosstalk associated with spectral neighbors for that optical module. The crosstalk correction values are derived by performing an analysis based on amplification data from a nucleic acid amplification of a nucleic acid sample using a detection probe, wherein the nucleic acid amplification occurs over a plurality of interrogation periods, and wherein the analysis comprises acquiring the amplification data that indicates an amount of nucleic acid present for each of the plurality of interrogation periods, and determining a crosstalk correction value associated with one of the spectral neighbors based on the amplification data.

In yet another aspect, a device includes a control module configured to initialize a nucleic acid amplification of a first nucleic acid sample and receive first amplification data that indicates an amount of nucleic acid present for each of a first plurality of interrogation periods. The device includes an amplification module configured to apply a crosstalk correction value an optical module to obtain corrected amplification data having reduced spectral crosstalk associated with a spectral neighbor for that optical module. The crosstalk correction value is derived by performing an analysis based on second amplification data from a nucleic acid amplification of a second nucleic acid sample using a detection probe, wherein the nucleic acid amplification occurs over a second plurality of interrogation periods, and wherein the analysis comprises acquiring the second amplification data that indicates an amount of nucleic acid present for each of the second plurality of interrogation periods, and determining a crosstalk correction value associated with the spectral neighbor based on the second amplification data. The device includes an interface module configured to update a display based on the corrected amplification data.

In one aspect, the disclosure is directed to a method including performing a polymerase chain reaction (PCR) amplification of a nucleic acid sample, wherein the PCR amplification occurs over a plurality of PCR interrogation periods using a detection probe. From the PCR amplification, data is acquired that indicates an amount of nucleic acid present for each of the plurality of PCR interrogation periods. The method also includes, based on the amplification data, determining a crosstalk correction value associated with a spectral neighbor to the probe to reduce spectral crosstalk from the spectral neighbor, and applying the crosstalk correction value to amplification data collected from multiplex PCR amplification of nucleic acid samples.

In a preferred embodiment, based on the amplification data, a crosstalk correction value is determined that is associated with a nearest spectral neighbor to the probe to reduce spectral crosstalk from the nearest spectral neighbor, and applying the crosstalk correction value is applied to amplification data collected from multiplex PCR amplification of nucleic acid samples.

Alternatively, the method may use more than one probe to perform polymerase chain reaction (PCR) amplification of a nucleic acid sample over one or more PCR interrogation periods and more than one crosstalk correction values are computed, wherein each crosstalk correction value is associated with a spectral neighbor. For example, any spectral neighbor with peak fluorescence of the detection target dye and the neighboring target dye separated by a distance less than a threshold distance.

In another aspect, a method comprises performing a multiplex polymerase chain reaction (PCR) amplification of a nucleic acid sample, wherein the multiplex PCR amplification comprises a plurality of PCR interrogation periods, and, from the PCR amplification, acquiring amplification data that indicates an amount of nucleic acid present for each of the plurality of PCR interrogation periods. The method also comprises applying a crosstalk correction factor to the amplification data to generate modified amplification data in which spectral crosstalk signals from a nearest spectral neighbor are reduced, wherein the crosstalk correction factor is derived based on multiplex PCR amplification of a second nucleic acid sample, and displaying the modified amplification data.

"Interrogation period" as used herein means the time point or time unit in which amplification of a target nucleic acid sequence occurs and/or is measured. For example, in PCR, an interrogation period is a thermal amplification cycle, while in TMA an interrogation period is a period of time, such as minutes or seconds.

The details of one or more embodiments of the invention are set forth in the accompanying drawings and the description below. Other features, objects, and advantages of the invention will be apparent from the description and drawings, and from the claims.

DETAILED DESCRIPTION

In general, the present disclosure is directed to techniques for processing nucleic acid amplification data to reduce spectral crosstalk effects. In one aspect, the present disclosure is directed to applying spectral crosstalk compensation to amplification data collected in nucleic acid amplification. In some aspects, only crosstalk due to a spectral neighbor is factored out by a compensation algorithm. While the following description is exemplifies applying crosstalk compensation to real-time PCR amplification data, it will be understood that the techniques described herein may be applied to data collected by other nucleic acid amplification, such as, for example, nucleic acid sequence based amplification (NASBA), transcription mediated amplification (TMA), ligase chain reaction (LCR), strand-displacement amplification (SDA), and the like.

Figure 1:
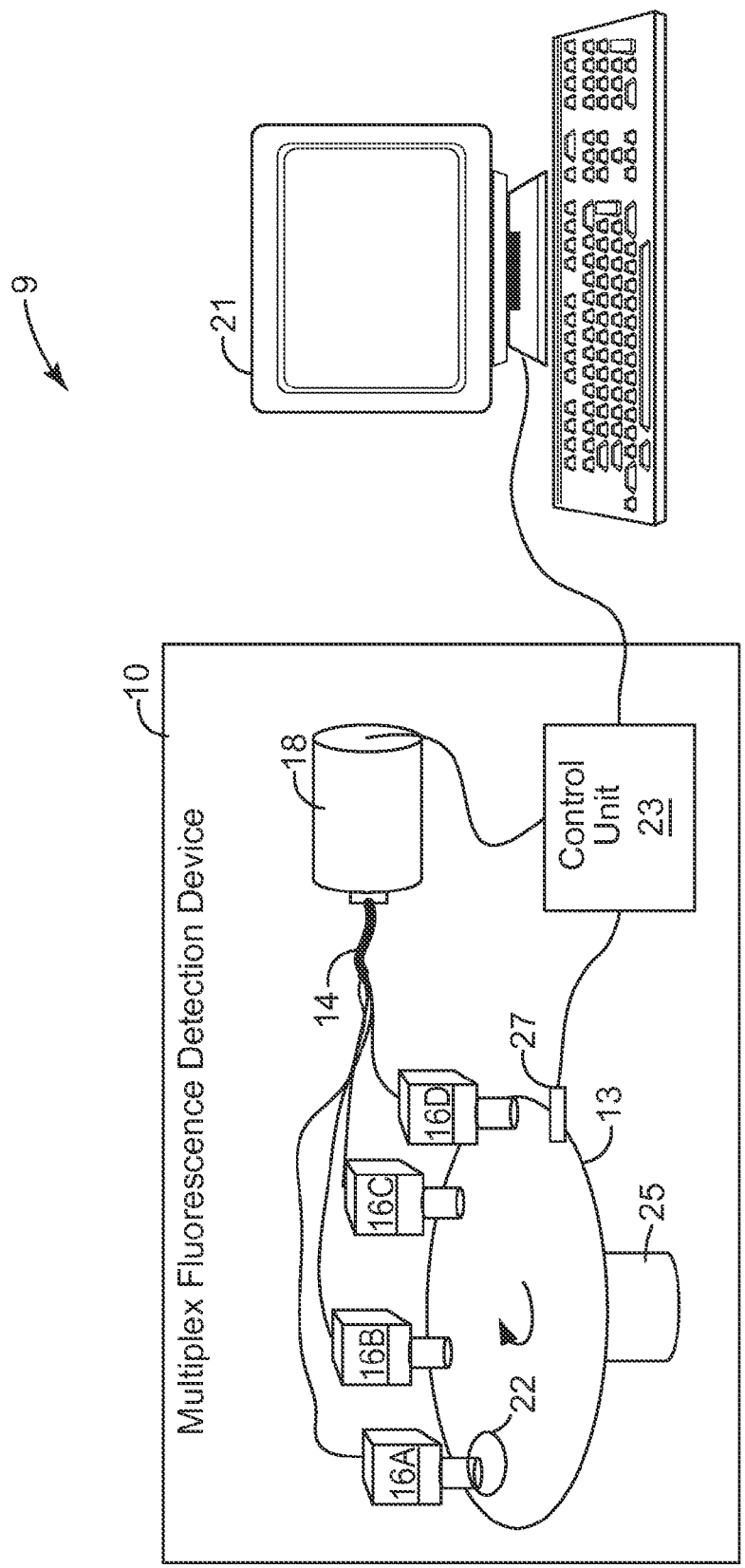
FIG. 1 is a block diagram illustrating an exemplary embodiment of a multiplex fluorescence detection device.

FIG. 1 is a block diagram illustrating an exemplary embodiment of a nucleic acid amplification system 9 including a data acquisition device 21 and a multiplex fluorescence detection device 10. System 9 collects amplification data from at least one nucleic acid sample and analyzes the amplification data using spectral crosstalk correction based on the techniques described herein. In the illustrated example, device 10 has four optical modules 16 that provide four "channels" for optical detection of four different dyes. In particular, device 10 has four optical modules 16 that excite different regions of rotating disk 13 at any given time, and collect emitted fluorescent light energy at different wavelengths from the dyes. As a result, modules 16 may be used to substantially simultaneously interrogate multiple, parallel reactions occurring within sample 22. System 9, capable of detecting multiple target species in real-time nucleic acid amplification, may be referred to as a multiplex system. In other embodiments, multiple different reactions occurring in different chambers of disk 13 may be interrogated substantially simultaneously.

The multiple reactions may, for example, occur simultaneously within a single chamber of a rotating disk 13. Each of optical modules 16 interrogates sample 22 and collects fluorescent light energy at different wavelengths as the disk 13 rotates. For example, excitation sources within modules 16 may be sequentially activated for periods sufficient to collect data at the corresponding wavelengths for each interrogation period. That is, an optical module 16A may be activated for a period of time to collect data at a first range of wavelengths selected for a first dye corresponding to a first reaction. The excitation source may then be deactivated, and an excitation source within module 16B may be activated to interrogate sample 22 at a second range of wavelengths selected for a second dye corresponding to a second reaction. This process continues until data has been captured from all optical modules 16. In one embodiment, each of the excitation sources within optical modules 16 is activated for an initial period of approximately two seconds to reach steady state followed by an interrogation period which lasts for 10-50 rotations of disk 13. In other embodiments, the excitation sources may be sequenced for shorter (e.g., 1 or 2 milliseconds) or longer periods. In some embodiments, more than one optical module may be activated simultaneously for concurrent interrogation of sample 22 without stopping the rotation of disk 13.

Although a single sample 22 is illustrated, disk 13 may contain a plurality of chambers holding samples. Optical modules 16 may interrogate some or all of the different chambers at different wavelengths. In one embodiment, disk 13 includes 96 chambers space around a circumference of disk 13. With a 96 chamber disk and four optical modules 16, device 10 may be capable of acquiring data from 384 different species. In this way, system 10 may be capable of acquiring data concurrently from samples including different nucleic acids and/or different fluorescent dyes.

In one embodiment, optical modules 16 include excitation sources that are inexpensive high power light emitting diodes (LEDs), which are commercially available in a variety of wavelengths and have long lifetimes (e.g., 100,000 hours or more). In another embodiment, conventional halogen bulbs or mercury lamps may be used as excitation sources.

As illustrated in FIG. 1, each of optical modules 16 may be coupled to one leg of a fiber optic bundle 14. Fiber optic bundle 14 provides a flexible mechanism for collection of fluorescent signals from optical modules 16 without loss of sensitivity. In general, a fiber optic bundle comprises multiple optical fibers laid side by side and bonded together at the ends and encased in a flexible protective jacket. Alternatively, fiber optic bundle 14 may comprise a smaller number of discrete, large diameter multi-mode fibers, either glass or plastic, having a common end. For example, for a four-optical module device, fiber optic bundle 16 may comprise four discrete multimode fibers, each having a 1 mm core diameter. The common end of the bundle contains the four fibers bound together. In this example, the aperture of detector 18 may be 8 mm, which is more than sufficient for coupling to the four fibers.

In this example, fiber optic bundle 14 couples optical modules 16 to a detector 18. The optical fibers carry the fluorescent light collected by optical modules 16 and effectively deliver the captured light to detector 18. In one embodiment, detector 18 is a photomultiplier tube. In another embodiment, the detector may include multiple photomultiplier elements, one for each optical fiber, within the single detector. In other embodiments, one or more solid-state detectors may be used.

The use of a single detector 18 may be advantageous in that it allows use of a highly sensitive and possibly expensive detector (e.g., a photomultiplier), while maintaining a minimal cost in that only a single detector need be used. A single detector is discussed herein; however, one or more detectors may be included for detecting a greater number of dyes. For example, four additional optical modules 16 and a second detector may be added to the system to allow for the detection of eight different wavelengths emitted from one disk. An exemplary fiber optic bundle coupled to a single detector for use with rotating disk 13 is described in U.S. Patent Application Publication No. 2006-0223172, entitled "MULTIPLEX FLUORESCENCE DETECTION DEVICE HAVING FIBER BUNDLE COUPLING MULTIPLE OPTICAL MODULES TO A COMMON DETECTOR," the entire content of which is hereby incorporated by reference.

Optical modules 16 are removable from the device and easily interchangeable with other optical modules that are optimized for interrogation at different wavelengths. For example, optical modules 16 may be physically mounted within locations of a module housing. Each of optical modules 16 may be easily inserted within a respective location of the housing along guides (e.g., recessed grooves) that mate with one or more marking (e.g., guide pins) of the optical module. Each optical module includes an optical output port (shown in FIGS. 6A and 7A) for coupling to one leg of fiber optic bundle 14. The optical output port may have a threaded end coupled to a threaded connector of the leg. Alternatively, a form of "quick-connect" may be used (e.g., a slidable connection having an o-ring and a catch pin) that allows fiber optic bundle 14 to be slidably engaged and disengaged from the optical output port. Moreover, each of optical modules 16 may have one or more electrical contacts for electronically coupling to control unit 23 when fully inserted.

The modular architecture of device 10 allows the device to be easily adapted for all of the fluorescent dyes used in a given amplification environment, such as multiplex PCR. Other chemistries that may be used in device 10 include Invader® (Third Wave, Madison, Wis.), Transcripted-mediated Amplification (GenProbe, San Diego, Calif.), fluorescence labeled enzyme linked immunosorbent assay (ELISA) or fluorescence in situ hybridization (FISH). The modular architecture of device 10 may provide another advantage in that the sensitivity of each optical module 16 can be optimized by choice of the corresponding excitation source (not shown) and excitation and detection filters for a small specific target range of wavelengths in order to selectively excite and detect a corresponding dye in the multiplex reaction.

For purpose of example, device 10 is illustrated in a 4-color multiplex arrangement, but more or less channels can be used with the appropriate fiber optic bundle 14. This modular design allows a user to easily upgrade device 10 in the field by simply adding another optical module 16 to base 20 and inserting one leg of fiber optic bundle 14 into the new optical module. Optical modules 16 may have integrated electronics that identify the optical modules and download calibration data into an internal control module or other internal electronics (e.g., control unit 23) of device 10.

In the example of FIG. 1, samples 22 are contained in chambers of disk 13, which is mounted on a rotating platform 25 under the control of control unit 23. A slot sensor trigger 27 provides an output signal utilized by control unit 23 and data acquisition device 21 for synchronizing data acquisition with chamber position during disk rotation. Slot sensor trigger 27 may be a mechanical or optical sensor. For example, the sensor may be a laser which sends a beam of light to disk 13 and control unit 23 uses a sensor detecting light passing through a slot in disk 13 to locate the chambers on the disk. In other embodiments, disk 13 may include a tab, protrusion or reflective surface in addition to or in place of the slot. Slot sensor trigger 27 may use any physical structure or mechanism to locate the radial position of disk 13 as it rotates. Optical modules 16 may be physically mounted above rotating platform 25. As a result, optical modules 16 are overlapped with different chambers at any one time.

Data acquisition device 21 provides an operating environment having hardware and software for controlling the operation of fluorescence detection device 10, including control unit 23, optical modules 16A-16D and detector 18, to detect a fluorescent dye in a sample 22. In particular, a user interacts with data acquisition device 21 to initiate nucleic acid amplification of one or more samples contained within one or more chambers of rotating disk 13 under control of control unit 23. In response, one or more of optical modules 16 of detection device 10 excites one or more corresponding regions of rotating disk 13 and collects emitted fluorescent light energy from a dye contained within the chambers. Disk 13 is mounted on a rotating platform 25. Control module 19 controls rotating platform 15 by engaging a motor associated with the rotating platform 25 to spin disk 13 at a controlled speed.

Detection device 10 also includes a heating element (not shown) for controlling, for example, the temperature of the sample 22 on disk 13. The heating element may comprise a cylindrical halogen bulb contained within a reflective enclosure. The reflective enclosure is shaped to focus radiation from the bulb onto a radial section of disk 13. Generally, the heated area of disk 13 would resemble a ring as disk 13 spins. In this embodiment, the shape of the reflective enclosure may be a combination of elliptical and spherical geometries that allow precise focusing. In other embodiments, the reflective enclosure may be of a different shape or the bulb may broadly irradiate a larger area. In other embodiments, the reflective enclosure may be shaped to focus the radiation from the bulb onto a single area of the disk 13, such as a single process chamber containing a sample 22.

In some embodiments, the heating element may heat air and force the hot air over one or more samples to modulate the temperature. Additionally, the samples may be heated directly by the disk. In this case, the heating element may be located in platform 25 and thermally couple to disk 13. Electrical resistance within the heating element may heat a selected region of the disk as controlled by control unit 23. For example, a region may contain one or more chambers, possibly the entire disk. An exemplary heating element for use with rotating disk 13 is described in U.S. Patent Application Publication No. 2007-0009382, entitled "HEATING ELEMENT FOR A ROTATING MULTIPLEX FLUORESCENCE DETECTION DEVICE," the entire content of which is hereby incorporated by reference.

Alternatively, or in addition, device 10 may also include a cooling component (not shown). A fan is included in device 10 to supply cold air, i.e., room temperature air, to disk 13. Cooling may be needed to modulate the temperature of the sample appropriately and store samples after an experiment has completed. In other embodiments, the cooling component may include thermal coupling between platform 25 and disk 13, as platform 25 may reduce its temperature when needed. For example, some biological samples may be stored at 4 degrees Celsius to reduce enzyme activity or protein denaturing.

Detection device 10 may also be capable of controlling reaction species contained within a process chamber. For example, it may be beneficial to load some species in a process chamber to generate one reaction and later adding another species to the sample once the first reaction has terminated. A laser homing valve may be added to control a valve position separating an inner holding chamber from the process chamber, thereby controlling the addition of species to the chamber during rotation of disk 13. This laser device may be located within one of optical modules 16 or separate from the optical modules. Directly below the laser, under disk 13, may be a laser sensor for positioning the laser relative to disk 13.

In one embodiment, the laser is a near infrared (NIR) laser with at least two power settings. Under a low power setting, the laser positioning sensor may indicate that the laser is in position over the chamber valve by recognizing the NIR light though a slot in disk 13. Once the laser is in position, control unit 23 directs the laser to output a short burst of high power energy to heat the valve and open it. The open valve may then allow the inner fluid specimen to flow toward from the inside chamber to the outside process chamber and conduct a second reaction. In some embodiments, disk 13 may contain a plurality of valves to generate a plurality of reactions in sequence. More than one set of laser and laser sensor may also be used when utilizing multiple chamber valves. An exemplary laser homing valve control system for use with rotating disk 13 is described in U.S. Patent Application Publication No. 2007-0009383, entitled "VALVE CONTROL SYSTEM FOR A ROTATING MULTIPLEX FLUORESCENCE DETECTION DEVICE," the entire content of which is hereby incorporated by reference.

Data acquisition device 21 may collect data from device 10 for each dye either sequentially or in parallel. In one embodiment, data acquisition system 21 collects the data from optical modules 16 in sequence, and corrects the spatial overlap by a trigger delay for each one of the optical modules measured from slot sensor trigger 27.

One application for device 10 is real-time PCR, but the techniques described herein may be extended to other platforms that utilize fluorescence detection at multiple wavelengths. Device 10 may combine rapid thermal cycling, utilizing the heating element, and centrifugally driven microfluidics for isolation, amplification, and detection of nucleic acids. By making use of multiplex fluorescence detection, multiple target species may be detected and analyzed in parallel.

For real-time PCR, fluorescence is used to measure the amount of amplification in one of three general techniques. The first technique is the use of a dye, such as Sybr® Green (Molecular Probes, Eugene, Oreg.), whose fluorescence increases upon binding to double-stranded DNA. The second technique uses fluorescently labeled probes whose fluorescence changes when bound to the amplified target sequence (hybridization probes, hairpin probes, etc.). This technique is similar to using a double-stranded DNA binding dye, but is more specific because the probe will bind only to a certain section of the target sequence. The third technique is the use of hydrolysis probes (Taqman™, Applied BioSystems, Foster City Calif.), in which the exonuclease activity of the polymerase enzyme cleaves a quencher molecule from the probe during the extension phase of PCR, making it fluorescently active.

In each of the approaches, fluorescence is linearly proportional to the amplified target concentration. Data acquisition system 21 measures an output signal from detector 18 (or alternatively optionally sampled, buffered, and communicated by control unit 23 after the PCR cycle) to observe the amplification in near real-time. In multiplex PCR, the multiple targets are labeled with different dyes that are measured independently. Generally speaking, each dye will have different absorbance and emission spectra. For this reason, optical modules 16 may have excitation sources, lenses and related filters that are optically selected for interrogation of sample 22 at different wavelengths.

The techniques described herein may be applied to reduce or eliminate spectral crosstalk in multiplex nucleic acid amplification, such as real-time PCR, performed by system 9. Spectral crosstalk occurs due to spectral overlap of one fluorescent probe (e.g., dye) onto neighboring detection channels, and can lead to false positive determinations. In accordance with the techniques of this disclosure, a set of crosstalk correction factors is determined from a calibration process. The calibration process is performed using actual real-time amplification data obtained with the appropriate probes in a series of single-plex reactions. All channels are scanned for each reaction even though only one target is present, to quantify the amount of crosstalk of that probe onto the neighboring modules. The calibration procedure calculates a crosstalk correction factor for each module 16.

While generally described in reference to real-time PCR, the techniques described herein may be applied to data collected by other nucleic acid amplifications, such as, for example, transcription mediated amplification (TMA). With respect to TMA, for example, a single-plex real-time TMA reaction occurs, and amplification data is collected over a TMA interrogation period spanning a time period, e.g., 30-60 minutes. Amplification data may be collected by each of a plurality of detection channels. The amplification data indicates an amount of nucleic acid present at different points along the interrogation period. A baseline subtraction may be performed for each channel, and crosstalk correction values may be determined for each channel, in a manner similar to that described above. Based on this, crosstalk correction values may be obtained for each module. The crosstalk correction values may be stored and applied to subsequently acquired amplification data to adjust the data.

As described in further detail below, system 9 is initialized with the crosstalk correction factors for each module 16, and is configured to perform an algorithm that employs the set of crosstalk correction factors to automatically subtract the amount of signal of neighboring channels onto the channel of interest. This may reduce or eliminate false positive determinations. For example, in some embodiments, data acquisition device 21 is configured to apply the set of crosstalk correction factors to signals obtained by multiplex fluorescence detection device 10. In other embodiments, control unit 23 of multiplex fluorescence detection device 10 is configured to apply the set of crosstalk correction factors to the obtained signals. In either case, system 9 may be configured with the set of crosstalk correction factors during the manufacturing process. Alternatively, system 9 may be configured with the set of crosstalk correction factors by software installation by a customer.

Data acquisition system 21 may store data representative of the output signal(s) for each interrogation period as amplification data in matrix or table format, where, for example, each column of one row stores the cycle number and the same column of a second row stores the associated fluorescence intensity.

Some examples of suitable systems, construction techniques or materials that may be adapted for use in connection with the present invention may be described in, e.g., commonly-assigned U.S. Pat. No. 7,507,575, entitled "MULTIPLEX FLUORESCENCE DETECTION DEVICE HAVING REMOVABLE OPTICAL MODULES, U.S. Pat. No. 6,734,401 entitled "ENHANCED SAMPLE PROCESSING DEVICES SYSTEMS AND METHODS", and U.S. Patent Application Publication No. US 2002/0064885 entitled "SAMPLE PROCESSING DEVICES," the entire contents of each of which are incorporated by reference herein. Other useable device constructions may be found in, e.g., U.S. Provisional Patent Application Ser. No. 60/214,508 filed on Jun. 28, 2000 and entitled "THERMAL PROCESSING DEVICES AND METHODS"; U.S. Provisional Patent Application Ser. No. 60/214,642 filed on Jun. 28, 2000 and entitled "SAMPLE PROCESSING DEVICES, SYSTEMS AND METHODS"; U.S. Provisional Patent Application Ser. No. 60/237,072 filed on Oct. 2, 2000 and entitled "SAMPLE PROCESSING DEVICES, SYSTEMS AND METHODS"; U.S. Provisional Patent Application Ser. No. 60/260,063 filed on Jan. 6, 2001 and entitled "SAMPLE PROCESSING DEVICES, SYSTEMS AND METHODS"; U.S. Provisional Patent Application Ser. No. 60/284,637 filed on Apr. 18, 2001 and entitled "ENHANCED SAMPLE PROCESSING DEVICES, SYSTEMS AND METHODS"; U.S. Patent Application Publication No. 2007-0010007, entitled "SAMPLE PROCESSING DEVICE COMPRESSION SYSTEMS AND METHODS;" and U.S. Patent Application Publication No. US 2002/0048533 entitled "SAMPLE PROCESSING DEVICES AND CARRIERS." Other potential device constructions may be found in, e.g., U.S. Pat. No. 6,627,159, entitled "CENTRIFUGAL FILLING OF SAMPLE PROCESSING DEVICES" (Bedingham et al.). The entire content of these disclosures are incorporated herein by reference.

Figure 2:
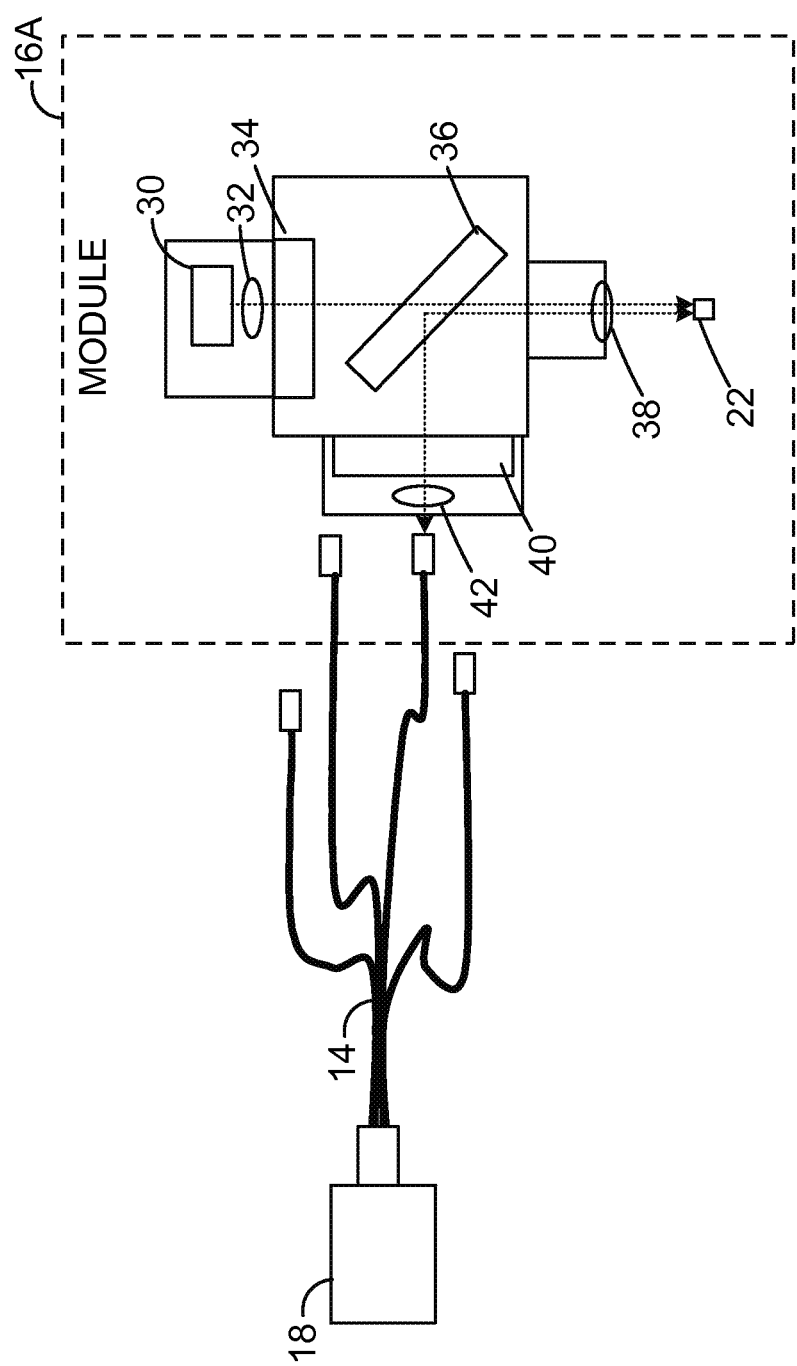
FIG. 2 is a schematic diagram illustrating an exemplary detection module, which may correspond to any of a plurality of detection modules of the fluorescence detection device of FIG. 1.

FIG. 2 is a schematic diagram illustrating an exemplary optical module 16A, which may correspond to any of optical modules 16 of FIG. 1. In this example, optical module 16A contains a high-power excitation source, LED 30, a collimating lens 32, an excitation filter 34, a dichroic filter 36, a focusing lens 38, a detection filter 40, and a lens 42 to focus the fluorescence into one leg of fiber optic bundle 14.

Consequently, the excitation light from LED 30 is collimated by collimating lens 32, filtered by excitation filter 34, transmitted through dichroic filter 36, and focused into the sample 22 by focusing lens 38. The resulting fluorescence emitted by the sample is collected by the same focusing lens 38, reflected off of dichroic filter 36, and filtered by detection filter 40 before being focused into one leg of fiber optic bundle 14. The optic bundle 14 then transfers the light to detector 18.

LED 30, collimating lens 32, excitation filter 34, dichroic filter 36, focusing lens 38, detection filter 40, and lens 42 are selected based on the specific absorption and emission bands of the multiplex dye with which optical module 16A is to be used. In this manner, multiple optical modules 16 may be configured and loaded within device 10 to target different dyes.

One advantage of the described modular, multiplex detection architecture is the flexibility in optimizing detection for a wide variety of dyes. Conceivably a user may have a bank of several different optical modules that can be plugged into device 10 as needed, of which N can used at any one time, where N is the maximum number of channels supported by the device. Therefore, device 10 and optical modules 16 may be used with any fluorescent dye and nucleic acid amplification detection method. A larger fiber optic bundle may be used to support a larger number of detection channels. Moreover, multiple fiber optic bundles may be used with multiple detectors. For example, two 4-legged fiber optic bundles may be used with eight optical modules 16 and two detectors 18.

Figure 3:
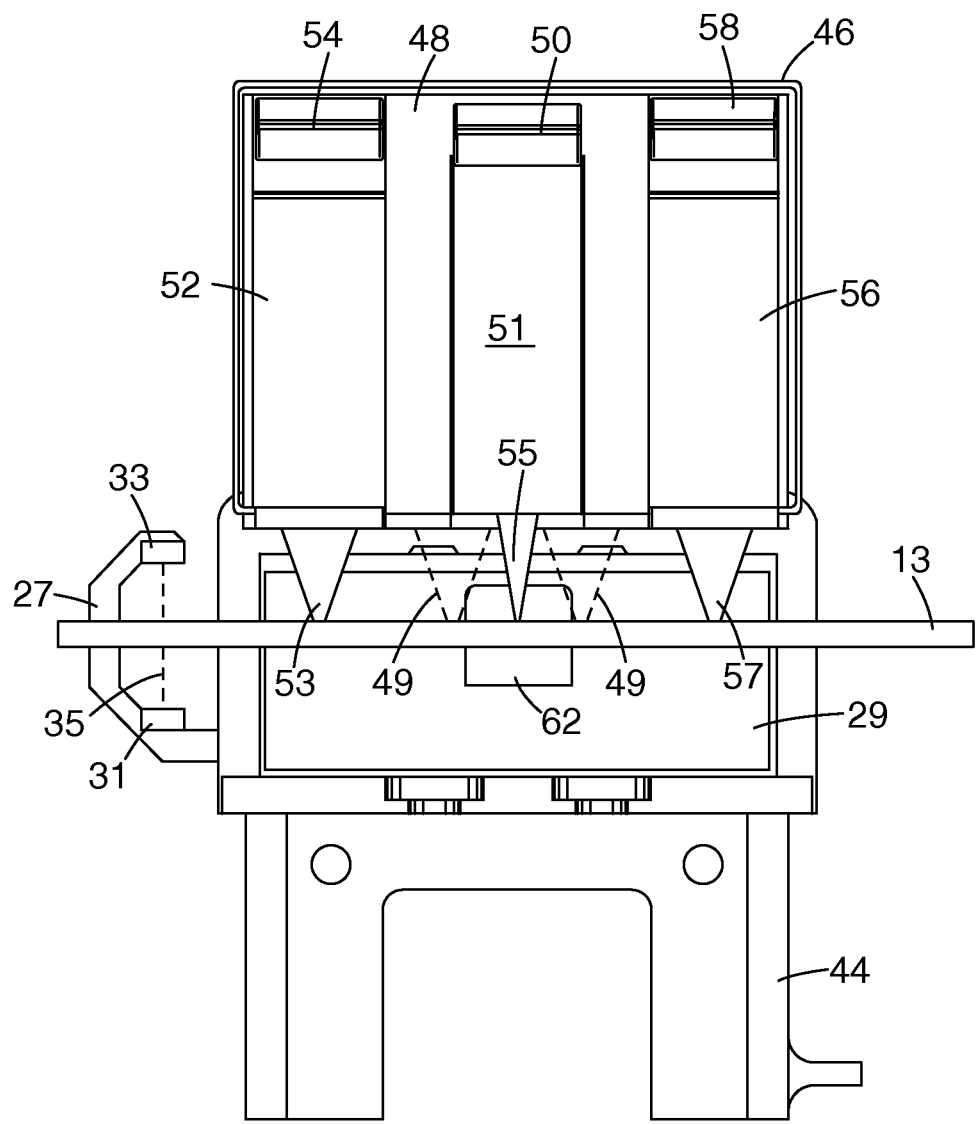
FIG. 3 is a perspective diagram illustrating a front view of an exemplary set of removable optical modules within the device housing.

FIG. 3 is a perspective diagram illustrating a front view of an exemplary set of removable optical modules within the device housing. In the example of FIG. 3, device 10 includes base arm 44 and module housing 46. Main optical module 48, supplemental optical module 52 and supplemental optical module 56 are contained within module housing 46. Optical modules 48, 52 and 56 produce optical output beams 49, 53 and 57, respectively, that sequentially excite different process chambers of disk 13. In other words, output beams 49, 53 and 57 follow the curvature of disk 13 to each excite the same radial position of the disk which contains the process chambers. Slot sensor trigger 27 includes infrared light source 31 which produces light 35 that is detected by detector 33.

Each of optical modules 48, 52 and 56 includes a respective release lever 50, 54 or 58, respectively, for engaging module housing 46. Each release lever may provide an upward bias to engage a respective latch formed within module housing 46. A technician or other user depresses release levers 50, 54 or 58, respectively, in order to unlatch and remove optical module 48, 52 or 56 from module housing 46. Barcode reader 29 includes laser 62 for identifying disk 13.

Base arm 44 extends from detection device 10 and provides support for module housing 46 and optical modules 48, 52 and 56. Module housing 46 may be securely mounted atop base arm 44. Module housing 46 may contain a location adapted to receive a respective one of optical modules 48, 52 and 56. Although described for exemplary purposes with respect to module housing 46, module housing 46 of detection device 10 may have a plurality of locations for receiving optical modules 48, 52 and 56. In other words, a separate housing need not be used for optical modules 48, 52 and 56.

Each location of module housing 46 may contain one or more tracks or guides which help to correctly position the associated optical module within the location when a technician or other user inserts the optical module. These guides may be located along the top, bottom, or sides of each location. Each of optical modules 48, 52 and 56 may include guides or tracks that mate with the guides or tracks of the locations of module housing 46. For example, module housing 46 may have protruding guides which mate with recessed guides in optical modules 48, 52 and 56.

In some embodiments, module housing 46 may not completely enclose each of optical modules 48, 52 and 56. For example, module housing 46 may provide mounting points to secure each of optical modules 48, 52 and 56 to base arm 44, but portions or all of each optical module may be exposed. In other embodiments, module housing 46 may completely enclose each of optical modules 48, 52 and 56. For example, module housing 46 may include a single door that closes over optical modules 48, 52 and 56, or a respective door for each of the modules. This embodiment may be appropriate for applications where the modules are seldom removed or detection device 10 is subjected to extreme environmental conditions.

A technician may easily remove any of optical modules 48, 52 or 56, and may be completed by using only one hand. For example, the technician may rest his or her forefinger under a molded lip located beneath release lever 54 of optical module 52. The technician's thumb may then press down release lever 54 to release optical module 52 from module housing 46. While grasping optical module 52 between the thumb and forefinger, the technician may pull back on the optical module to remove the optical module from detection device 10. Other methods may be used to remove any of optical module 48, 52 or 56, including methods utilizing two-handed removal. Inserting any of optical module 48, 52 or 56 may be accomplished in a reversed manner with one or two hands.

In the example of FIG. 3, the components of two optical modules are combined to form main optical module 48. Main optical module 48 may contain light sources that produce two different wavelengths of light and detectors for detecting each different wavelength of fluorescence from the samples in disk 13. Therefore, main optical module 48 may connect to two legs of fiber optic bundle 14. In this manner, main optical module 48 may be viewed as a dual-channeled optical module having two independent optical excitation and collection channels. In some embodiments, main optical module 48 may contain optical components for more than two optical modules. In other cases, module housing 46 contains a plurality (e.g., two or more) of single-channeled optical modules, such as supplemental optical modules 52 and 56.

As illustrated in FIG. 3, main optical module 48 may also contain components for a laser valve control system 51 (located within optical module 48). Laser valve control system 51 detects disk 13 location by a small slot located near the outer edge of disk 13. A detector (not shown) detects low power laser light 55 to map the location of disk 13 with respect to the motor which spins the disk. The control unit 23 uses the map to locate valves (not shown) on disk 13.

Laser valve control system 51 focuses laser light 55 on the valves that separate holding chambers towards the center of disk 13 from process chambers near the outer edge of disk 13. When the contents of the holding chambers are to be moved to the associated process chambers, laser valve control system 51 applies laser light 55 to heat a valve separating the chambers, causing the value open and providing fluid communication between the two chambers. In particular, once the valve is open, the contents from the inner holding chamber may then flow towards the outer process chamber as disk 13 is spinning. Detection device 10 may then monitor the subsequent reaction in the process chamber. Contents within a chamber may include substances in a fluid or solid state.

In some embodiments, laser valve control system 51 may be contained within a single-channeled optical module, e.g., supplemental optical module 54 or supplemental optical module 56. In other embodiments, laser valve control system 51 may be mounted to detection device 10 separately from any of optical modules 48, 52 or 56. In this case, laser valve control system 51 may be removable and adapted to engage a location within module housing 46 or a different housing of detection device 10.

In the example of FIG. 3, slot sensor trigger 27 is located near the removable modules, on either side of disk 13. In one embodiment, slot sensor trigger 27 contains a light source 31 to emit infrared (IR) light 35. Detector 33 detects IR light 35 when the slot in disk 13 allows the light to pass through the disk to detector 33. Control unit 23 may use this information to synchronize disk 13 locations as it is spinning with data from optical modules 48, 54 and 56. In some embodiments, slot sensor trigger 27 may extend from base arm 44 to reach the outer edge of disk 13 during device 10 operation. In other embodiments, a mechanical detector may be used to detect the position of disk 13.

Barcode reader 29 uses laser 62 to read a barcode located on the side edge of disk 13. The barcode identifies the type of disk 13 to allow proper operation of device 10. In some embodiments, the barcode may identify the actual disk to assist a technician in tracking data to specific samples from multiple disks 13.

All surface components of optical modules 48, 52 and 56 may be constructed of a polymer, composite, or metal alloy. For example, high molecular weight polyurethane may be used in forming the surface components. In other cases, an aluminum alloy or carbon fiber structure may be created. In any case, the material may be resistant to heat, fatigue, stress, and corrosion. As detection device 10 may come into contract with biological materials, the structures may be sterilizable in the event chamber contents leak out of disk 13.

Figure 4:
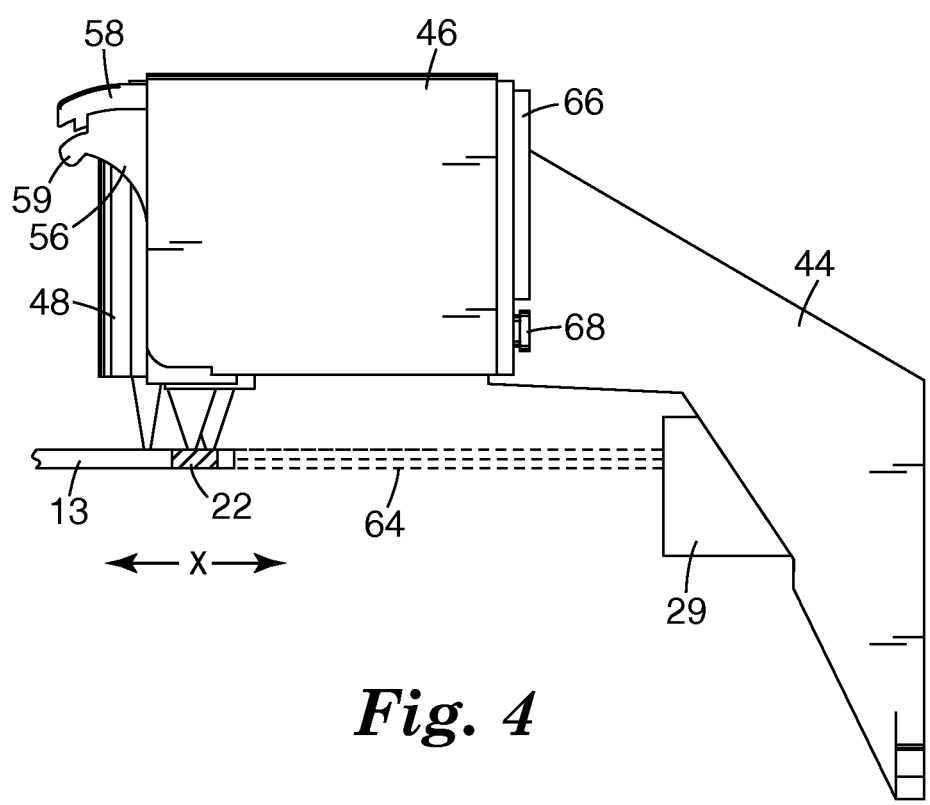
FIG. 4 is a perspective diagram illustrating the exemplary set of removable optical modules within the device housing.

FIG. 4 is a perspective diagram illustrating the exemplary set of removable optical modules 48, 52 and 56 within module housing 46 of detection device 10. In the example of FIG. 4, base arm 44 supports barcode reader 29 as well as the removable optical modules 48, 52 and 56 attached within module housing 46. Disk 13 is located beneath optical modules 48, 52 and 56 with the process chambers located under a respective optical path of each of the modules at different moments in time.

Within module housing 46, the fronts of supplementary module 56 and main optical module 48 can be seen. Supplementary module 56 contains molded lip 59 and release lever 58. As previously described, molded lip 59 may be used to grasp module 56 when removing or inserting the module into module housing 46. All of optical modules 48, 52 and 56 may have a respective molded lip and release lever, or a single release lever may be used to remove all of the optical modules. In some embodiments, optical modules 48, 52 and 56 may contain a different component for grasping the module. For example, each of optical modules 48, 52 and 56 may contain a handle for removing the respective module in a vertical or horizontal direction from module housing 46.

The location of optical modules 48, 52 and 56 within module housing 46 may be fixed in order to separately excite different samples within disk 13 at any particular moment in time. For example, main optical module 48 may be located slightly further toward base arm 44 than supplemental optical modules 52 and 56, which are offset to a location at either side of the main module. Moreover, optical modules 48, 52 and 56 may be offset in a horizontal direction (indicated by the arrow in FIG. 4, where X is the distance the outside light beams are offset from the inside light beams) so that the excitation light beams produced by the modules follows the curvature of disk 13. In this arrangement, the light beams produced by optical modules 48, 52 and 56 traverse the same path as disk 13 rotates, thereby exciting and collecting light from process chambers located along the path. In other embodiments, optical modules 48, 52 and 56 are aligned such that the excitation light beams traverse different paths around rotating disk 13.

In this example, base arm 44 contains electrical contact board 66 which extends into module housing 46. Inside module housing 46, electrical contact board 66 may contain electrical contacts for each of optical modules 48, 52 and 56. Electrical contact board 66 may be electrically coupled to control unit 23. In some embodiments, each of optical modules 48, 52 and 56 may have a separate associated electrical contact board which is connected to control unit 23.

Fiber optic coupler 68 couples one leg of the fiber optic bundle 14 to an optical output port of optical module 56. Although not shown, each of optical modules 48, 52 and 56 include an optical output port adapted to engage a respective fiber optic coupler mounted to module housing 46. The connection between fiber optic coupler 68 and the leg of fiber optic bundle 14 may be a threaded screw lock, snap closure or friction fit.

Barcode reader 29 produces laser light 64 for reading the barcode of disk 13. The laser light 64 follows a direct path where it interacts with the outer edge of disk 13. The light 64 may spread out to cover a large area of disk 13 at one time. Barcode reader 29 reads the barcode on disk 13 when the disk is rotating at slow speeds. In other embodiments, barcode reader 29 may read the barcode periodically during operation to make sure a new disk has not been loaded in device 10. The barcode reader 29 may detect more than one barcode on disk 13 in other embodiments.

In some embodiments, base arm 44 may be movable with respect to disk 13. In this case, base arm 44 could be configurable to detect samples on different sized disks or samples located within an interior of disk 13. For example, a larger disk containing more process chambers or larger process chambers may be used by moving the base arm 44 further away from the center of disk 13. Module housing 46 may also have a configurable position for each of optical module 48, 52 or 56 so that each module may be movable to one or more circular paths of process chambers around disk 13.

Figure 5:
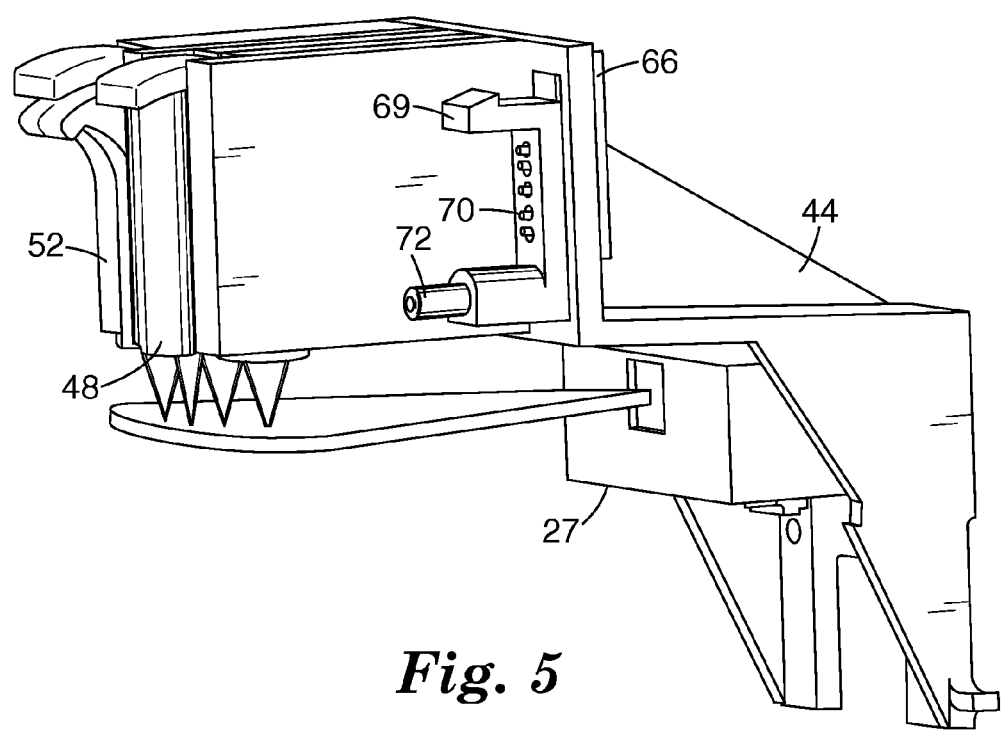
FIG. 5 is a perspective diagram illustrating a front side view of an exemplary set of removable optical modules having one module removed to expose a module connector.

FIG. 5 is perspective diagram illustrating a front side view of an exemplary set of removable optical modules having one module removed to expose a module connector. In particular, module housing 46 is not shown in FIG. 5, and optical module 56 has been removed to expose optical modules 52 and 48 along with the connections for removed module 56.

Release lever 58 (FIG. 3) of optical module 56 securely attaches to attachment post 69 mounted to base arm 44. In this example, attachment post 69 extends into optical module 56 and couples to release lever 58. In other embodiments, other attachment mechanisms may be used to fix optical module 56 to base arm 44, such as a screw or snap fixation device.

Base arm 44 provides two different operational connections within module housing 46 for receiving and engaging optical module 56, once inserted. In particular, base arm 44 provides electrical contact board 66, which includes electrical connections 70 for coupling to the electrical contacts (not shown) contained within optical module 56. Electrical connections 70 allow control unit 23 to communicate with electrical components within module 56. For example, module 56 may include electrical circuits, hardware, firmware, or any combination thereof. In one example, the internal electrical components may store and output to control unit 23 unique identification information, such as a serial number. Alternatively, or in addition, the electrical components may provide information describing the specific characteristics of the optical components contained within the removable module 56. For example, the electrical components may include programmable read-only memory (PROM), flash memory, or other internal or removable storage media. Other embodiments may include a set of resistors, a circuit or an imbedded processor for outputting a unique signature of optical modules 48, 52 or 56 to control unit 23. In another example, optical module 56 may include a laser source and other components that form part of a laser valve control system, i.e. laser valve control system 51.

Electrical contact board 66 may be removed and replaced with another version associated with a different removable optical module. This option may support upgrades in device capability. In other embodiments, connections 70 may contain more or less connection pins.

In addition, base arm 44 and module housing 46 provide optical channel 72 within the location for receiving optical module 56. Optical channel 72 is connected to fiber optic coupler 68 (FIG. 4) that interfaces with a leg of fiber optic bundle 14. Optical channel 72 inserts into a location within optical module 56. The light captured by optical module 56 may be directed through optical channel 72, fiber optic coupler 68 and fiber optic bundle 15 to the detector. Fittings between these connections may be tight to ensure that light does not escape or enter the optical path.

In some embodiments, the connections to optical module 56 may be arranged in a different configuration. For example, the connections may be located in another position for accepting optical module 56 from another direction. In other embodiments, electrical connections may be located on one side of optical module 56 while an optical connection is located on a second surface of module 56. In any case, the electrical and optical connections located within the location of module housing 46 accommodate a removable optical module, i.e., optical module 56 in this example.

The optical and electrical connections of module 56 described in FIG. 5 may be used with any module, including optical modules 48 and 52. In addition, the connections for each optical module may not be identical. Since connections may be modified for coupling with a desired removable optical module, the connections utilized by any particular optical module inserted within a particular location of module housing 46 may vary at any time.

Figure 6A:
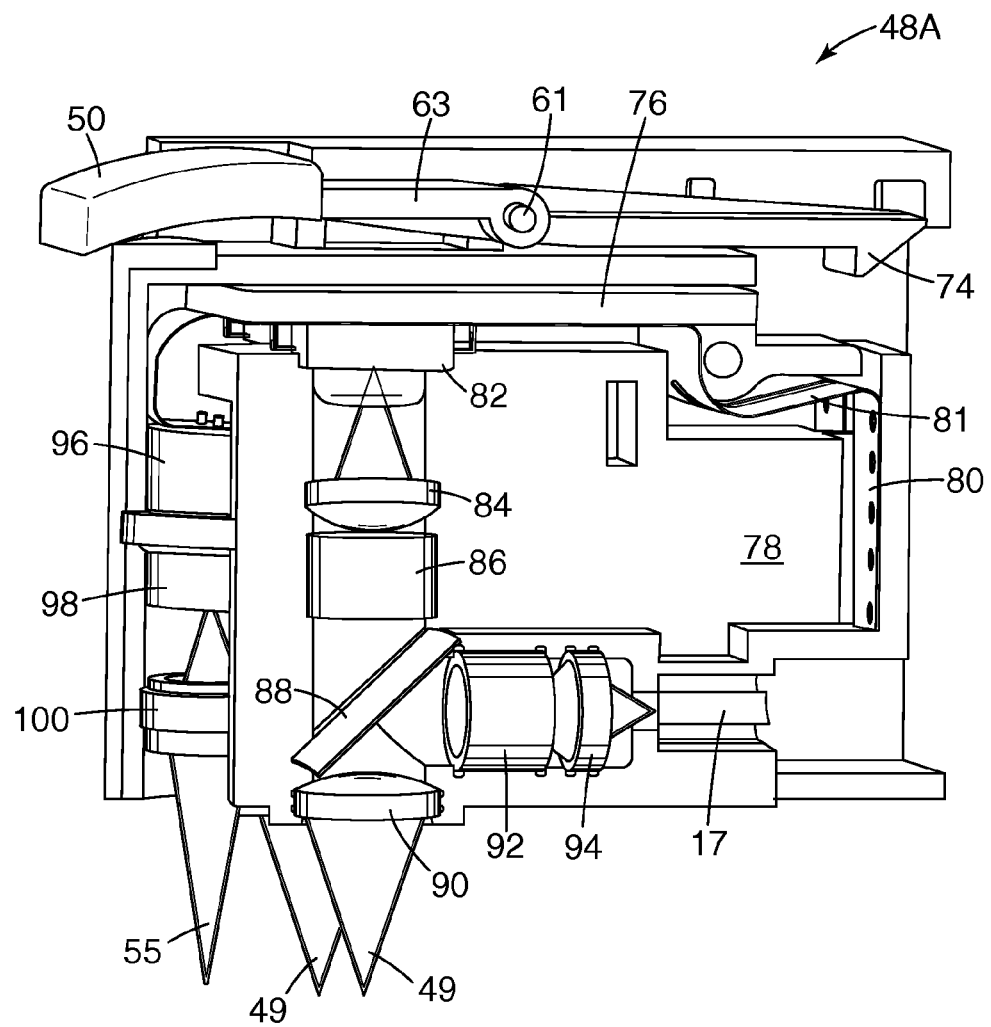
FIGS. 6A and 6B are perspective diagrams illustrating the components within exemplary main removable optical modules.

FIG. 6A is perspective diagram illustrating the components within an exemplary main removable optical module 48A. In the example of FIG. 6A, main optical module 48A includes release lever 50, pivot pin 51 and latch 74. Internal housing 78 separates each side of module 48A and contains electrical contacts pad 80 connected to ribbon 81. Optical components include LED 82, collimating lens 84, excitation filter 86, dichroic filter 88, focusing lens 90, detection filter 92 and lens 94. Optical output port 17 couples to a leg of fiber optic bundle 14. A separate set of optical components for a second optical channel (not shown) are located on the other side of internal housing 78. In addition, main module 48A includes connector 96, laser diode 98 and focusing lens 100 as part of a laser valve control system 51 controlled by control unit 23.

Release lever 50 is attached to optical module 48A by a pivot pin 61. Pivot pin 61 allows release lever 50 to rotate about the axis of the pin. When release lever 50 is depressed, arm 63 rotates counter-clockwise to raise latch 74. Once latch 74 is raised, optical module 48A may be free for removal from module housing 46. There may be a spring or other mechanism maintaining a bias force against release lever 50 to maintain latch 74 in a down position. In some embodiments, a spring may be included around pivot pin 61 to provide a moment arm that keeps latch 74 in the down, or latched, position. In other embodiments, other mounting mechanisms may be added to or used in place of the described lever. For example, optical module 48A may be attached to module housing 46 by one or more screws or pins.

Mounting board 76 may be installed within optical module 48A for attaching communication ribbon 81 and LED 82. Ribbon 81 is connected to electrical contacts pad 80 and provides a connection between the pad and electrical components within optical module 48A. Contacts pad 80 and ribbon 81 may carry the information required for both sides of main optical module 48A, including the laser valve control system 51 and any internal memory or other storage medium. Ribbon 81 may be flexible for weaving within optical module 48A. Ribbon 81 may contain a plurality of electrically conductive wires to communicate signals between the electrical components and control unit 23 and/or to deliver power to the electrical components. In some embodiments, each electrical component may have a separate cable connecting the component with control unit 23. A technician may need to disconnect a cable or flex circuit from module housing 46 when removing optical module 48A from the housing.

In some embodiments, optical module 48A may contain a detector for detecting light from disk 13 and electronics for processing and storing the data. The electronics may contain a telemetry circuit for wirelessly transmitting data representing the detected light to control unit 23. Wireless communication may be performed by infrared light, radio frequency, Bluetooth, or other telemetry technique. Optical module 48A may also include a battery to power the electronics, which may be rechargeable by control unit 23.

LED 82 is affixed to mounting board 76 and electrically coupled to ribbon 81. LED 82 produces excitation light 49 of a predetermined wavelength to excite the sample 22. After light 49 leaves LED 82, the light is expanded by collimating lens 84 before the light enters excitation filter 86. The light 49 of one wavelength band is passed by dichroic filter 88 and is focused on a sample by focusing lens 90. The light 49 excites the sample and fluorescence is collected by focusing lens 90 and delivered to detection filter 92 by dichroic filter 88. The resulting wavelength band of light is collected by lens 94 and delivered to optical output port 17 where the collected fluorescent light enters a leg of fiber optic bundle 14 for conveyance to detector 18.

Internal housing 78 may support all components included in the excitation of the sample and detection of fluorescent light emitted by the sample for a selected wavelength. On the other side of internal housing 78, a similar configuration of optical components may be included to produce light of a different wavelength and detect the corresponding different fluorescent wavelength. Separation of each side may eliminate light contamination from one side entering the optical channel of the other side.

Housed partially between each side of module 48A may be the components of the laser valve control system 51, including connector 96, laser diode 98 and focusing lens 100. Internal housing 78 may provide physical support for these components. Ribbon 81 is connected to connector 96 for communicating drive signals and power to the laser source. Laser diode 98 is connected to connector 96 and produces the laser energy 55 used to open valves on disk 13. Laser diode 98 delivers this near-infrared (NIR) light to focusing lens 100 for directing the laser energy 55 to specific valves on disk 13. An NIR sensor may be located below disk 13 for locating particular valves that need to be opened. In other embodiments, these components may be housed separately from the optical components.

In some embodiments, emission lens 98 and focusing lens 100 of laser valve control system 51 may be contained within a single-channeled optical module, such as supplemental optical module 52 and 56 (FIG. 3).

Figure 6B:
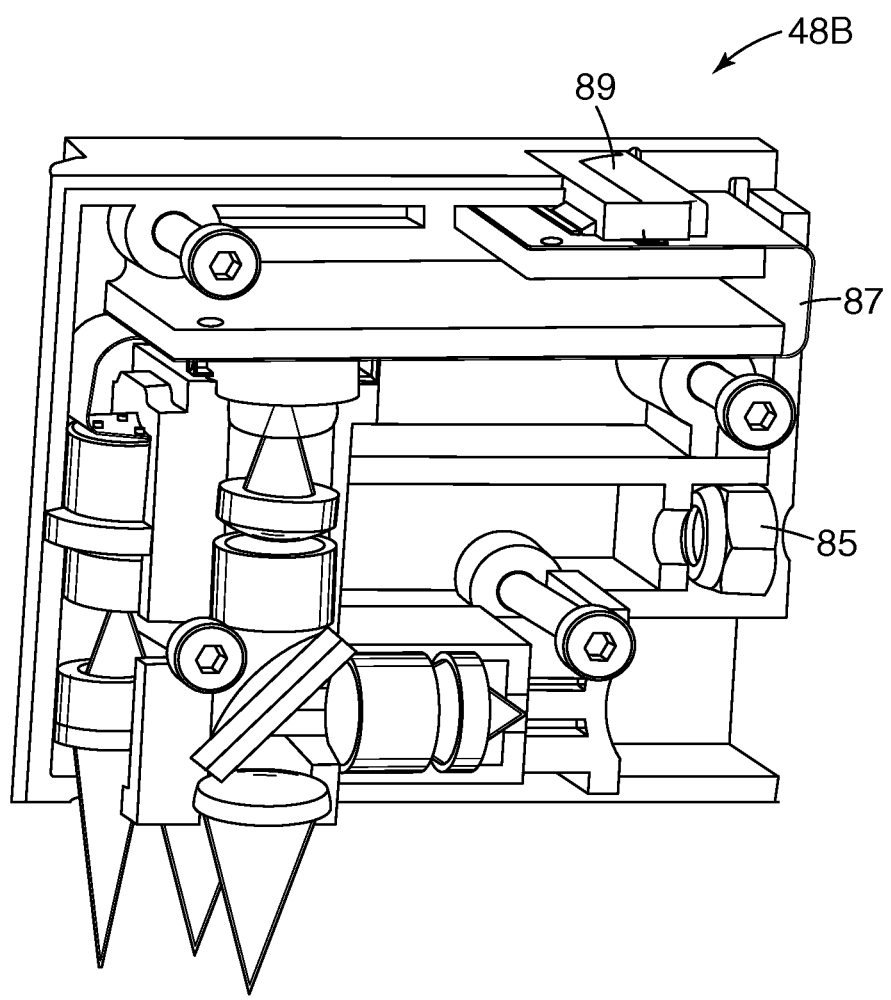

FIG. 6B is a perspective diagram illustrating the components within a different optical module substantially similar to FIG. 6A. Optical module 48B includes many of the same components as optical module 48A. Differences include nut 85, flex circuit 87 and flex circuit connector 89.

Optical module 48B does not require a latch mechanism for attaching to module housing 46. Alternatively, nut 85 is threaded and is engaged by a matching threaded bolt attached through module housing 46. Once tightened, optical module 48B is securely attached to detection device 10. In other embodiments, a different fastening device may be used. For example, a pin or track may lock optical module 48B into place.

Flex circuit 87 provides the electrical connection between components of optical module 48B with control unit 23. Flex circuit 87 is flexible to move between multiple locations. Flex circuit connector 89 is coupled to flex circuit 87 and provides a secure connection between flex circuit 87 and optical module 48B. Flex circuit connector 89 must be disengaged to completely remove optical module 48B from module housing 46.

Figure 7A:
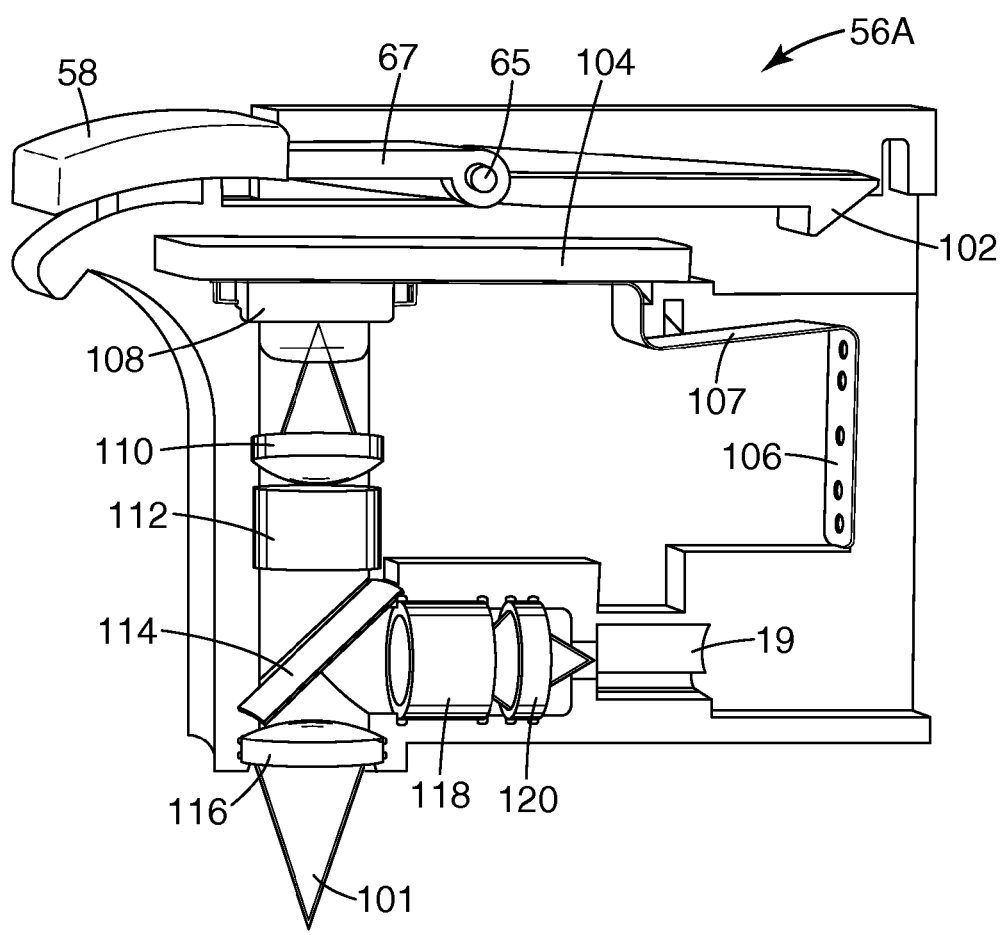
FIGS. 7A and 7B are perspective diagrams illustrating the components within exemplary supplemental removable optical modules.

FIG. 7A is a perspective diagram illustrating the components within an exemplary supplemental optical module that may be easily removed from or inserted into detection device 10. In the example of FIG. 7A, optical module 56A includes release lever 58, pivot pin 59 and latch 102, similar to main optical module 48A. Optical module 56A also includes electrical contacts pad 106 connected to ribbon 107. Ribbon 107 may also be connected to mounting board 104. Similar to main optical module 48A, optical components include LED 108, collimating lens 110, excitation filter 112, dichroic filter 114, focusing lens 116, detection filter 118 and lens 120. Optical output port 19 couples to a leg of fiber optic bundle 14.

Release lever 58 is attached to optical module 56A by a pivot pin 65. Pivot pin 65 allows the release lever to rotate about the axis of the pin. When release lever 58 is depressed, arm 67 rotates counter-clockwise to raise latch 102. Once latch 102 is raised, optical module 56A may be free for removal from module housing 46. There may be a spring or other mechanism maintaining a bias force against release lever 58 to maintain latch 102 in a down position. Alternatively, a spring may be located above latch 102. In some embodiments, a spring may be included around pivot pin 65 to provide a moment arm that keeps latch 102 in the down, or latched, position. In other embodiments, other mounting mechanisms may be added to or used in place of the described lever. For example, optical module 56A may be attached to module housing 46 by one or more screws or pins.

Mounting board 104 may be installed within optical module 56A for attaching communication ribbon 107 and LED 108. Ribbon 107 is connected to electrical contacts pad 106 and provides a connection between the pad and electrical components within optical module 56A. Contacts pad 106 and ribbon 107 may carry the information required for operating the optical components. Ribbon 107 may be flexible for weaving within optical module 56A. Ribbon 107 may contain a plurality of electrically conductive wires to communicate signals between the components and control unit 23 and/or deliver power to the electrical components. In some embodiments, each electrical component may have a separate cable connecting the component with control unit 23. A technician may need to disconnect a cable or flex circuit from module housing 46 when removing optical module 56A from the housing.

In some embodiments, optical module 56A may contain a detector for detecting light from disk 13 and electronics for processing and storing the data. The electronics may contain a telemetry circuit for wirelessly transmitting data representing the detected light to control unit 23. Wireless communication may be performed by infrared light, radio frequency, Bluetooth, or other telemetry technique. Optical module 56A may also include a battery to power the electronics, which may be rechargeable by control unit 23.

LED 108 is affixed to mounting board 104 and electrically coupled to ribbon 107. LED 108 produces excitation light 101 of a predetermined wavelength to excite the sample 22. After light 101 leaves LED 108, the light is expanded by collimating lens 110 before the light enters excitation filter 112. The light 101 of one wavelength band is passed by dichroic filter 114 and is focused on a sample by focusing lens 116. The light 101 excites the sample and fluorescence is collected by focusing lens 116 and delivered to detection filter 118 by dichroic filter 114. The resulting wavelength band of light is collected by lens 120 and delivered to optical output port 19 where the collected fluorescent light enters a leg of fiber optic bundle 14 for conveyance to detector 18.

Supplemental optical module 56A may also contain the components of the laser valve control system 51. Laser valve control system 51 may be the only system used within device 10 or one of a plurality of laser valve control systems. The components used for this system may be similar to the components described in optical module 48A of FIG. 6A.

The components of supplemental optical module 56A may be similar to any supplemental optical module or any optical module used to emit and detect one wavelength band of light. In some embodiments, the components may be altered in configuration to accommodate different experimental applications. For example, any optical modules may be modified to be inserted from a different direction or to be placed within the device at a different position with respect to disk 13. In any case, the optical modules may be removable to provide modification flexibility to device 10.

Figure 7B:
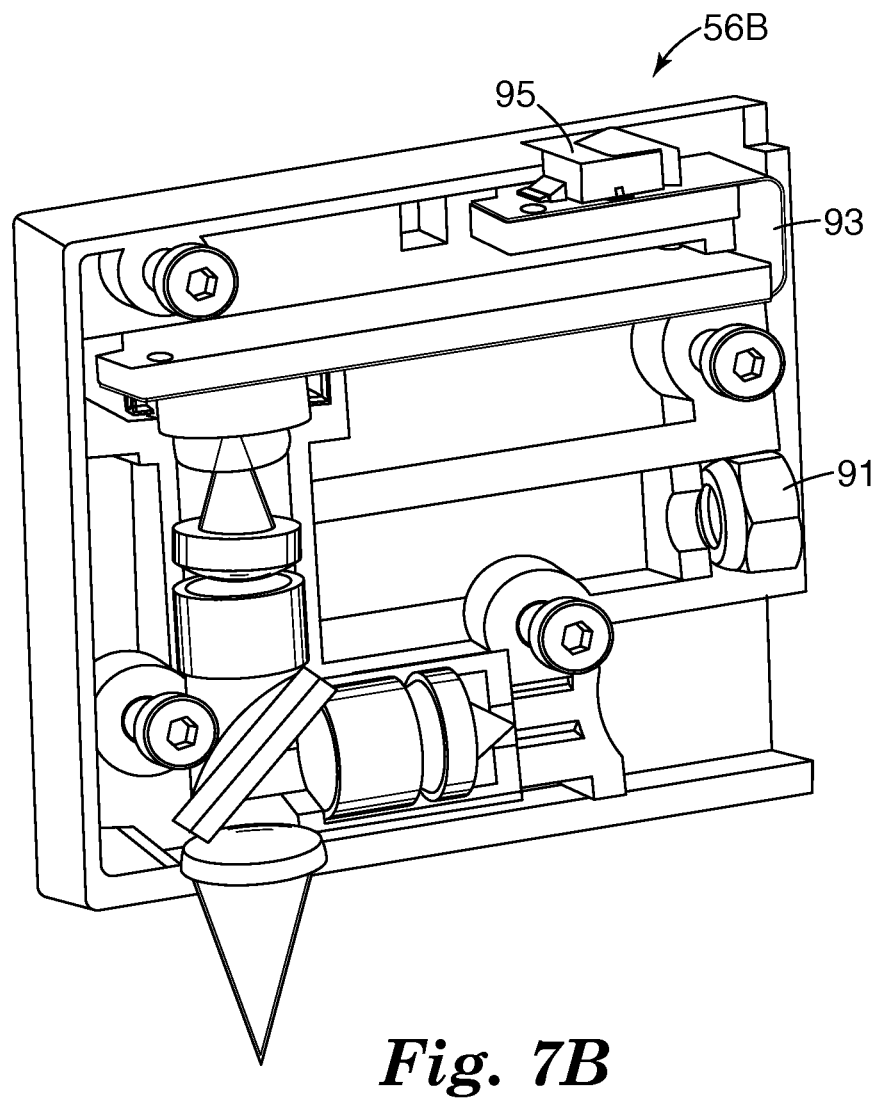

FIG. 7B is a perspective diagram illustrating the components within a different supplemental optical module substantially similar to FIG. 7A. Optical module 56B includes many of the same components as optical module 56A. Differences include nut 91, flex circuit 93 and flex circuit connector 95.

Optical module 56B does not require a latch mechanism for attaching to module housing 46. Alternatively, nut 91 is threaded and is engaged by a matching threaded bolt attached through module housing 46. Once tightened, optical module 56B is securely attached to detection device 10. In other embodiments, a different fastening device may be used. For example, a pin or track may lock optical module 56B into place.

Flex circuit 93 provides the electrical connection between components of optical module 56B with control unit 23. Flex circuit 93 is flexible to move between multiple locations. Flex circuit connector 95 is coupled to flex circuit 93 and provides a secure connection between flex circuit 93 and optical module 56B. Flex circuit connector 95 must be disengaged to completely remove optical module 56B from module housing 46.

Figure 8:
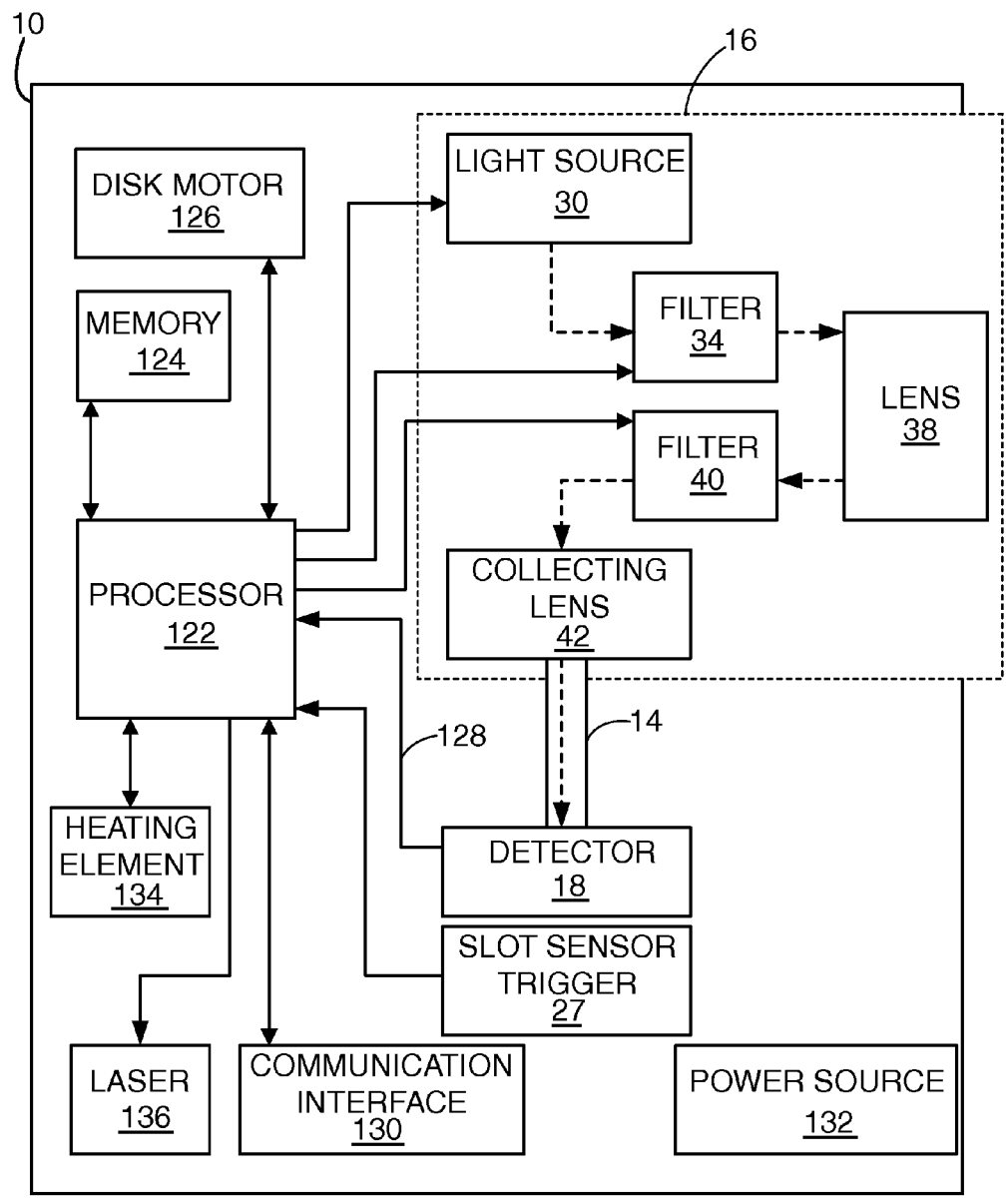
FIG. 8 is a block diagram illustrating an example embodiment of the multiplex fluorescence detection device in further detail.

FIG. 8 is a functional block diagram of an example embodiment of multiplex fluorescence detection device 10. In particular, FIG. 8 indicates the electrical connections between device components and the general paths of light through the components. In the example of FIG. 8, device 10 includes at least one processor 122 or other control logic, memory 124, disk motor 126, light source 30, excitation filter 34, lens 38, detection filter 40, collecting lens 42, detector 18, slot sensor trigger 27, communication interface 130, heating element 134, laser 136 and power source 132. As shown in FIG. 3, lens 38 and collecting lens 42 need not be electrically connected to another component. Further, light source 30, filters 34 and 40, lens 38 and collecting lens 42 are representative of one optical module 16. Although not illustrated in FIG. 8, device 10 may contain additional optical modules 16, as described previously. In that case, each additional optical module may include components arranged substantially similarly as to those shown in FIG. 8.

Light follows a certain path through several components in FIG. 8. Once light is emitted by light source 30, it enters excitation filter 34 and leaves as light of a discrete wavelength. It then passes through lens 38 where it leaves detection device 10 and excites sample 22 within a process chamber (not shown). Sample 22 responds by fluorescing at a different wavelength, at which time this fluorescent light enters lens 38 and is filtered by detection filter 40. Filter 40 removes background light of wavelengths outside of the desired fluorescence from sample 22. The remaining light is sent through collecting lens 42 and enters a leg of fiber optic bundle 14 before being detected by detector 18. Detector 18 subsequently amplifies the received light signal.

Processor 122, memory 124 and communication interface 130 may be part of control unit 23. Processor 122 controls disk motor 126 to rotate or spin disk 13 as needed to collect fluorescence information or move fluid through disk 13. Processor 122 may use disk position information received from slot sensor trigger 27 to identify the location of chambers on disk 13 during rotation and synchronize the acquisition of florescence data received from the disk 13.

Processor 122 may also control when the light source 30 within optical module 16 is powered on and off. In some embodiments, processor 122 controls excitation filter 34 and detection filter 40. Depending on the sample being illuminated, processor 122 may change the filter to allow a different wavelength of excitation light to reach the sample or a different wavelength of fluorescence to reach collecting lens 42. In some embodiments, one or both filters may be optimized for the light source 30 of the particular optical module 16 and not changeable by processor 122.

Collecting lens 42 is coupled to one leg of fiber bundle 14 that provides an optical path for the light from the collecting lens to detector 18. Processor 122 may control the operation of detector 18. While detector 18 may constantly be detecting all light, some embodiments many utilize other acquisition modes. Processor 122 may determine when detector 18 collects data and may programmatically set other configuration parameters of detector 18. In one embodiment, detector 18 is a photomultiplier tube that capture fluorescence information from light provided by collecting lens 42. In response, detector 18 produces an output signal 128 (e.g., an analog output signal) representative of the received light. Although not shown in FIG. 8, detector 18 may concurrently receive light from other optical modules 16 of device 10. In that case, output signal 128 electrically represents a combination of the optical input received by detector 18 from the various optical modules 16.

Processor 122 may also control data flow from device 10. Data such as sampled fluorescence from detector 18, temperature of the samples from heating element 134 and related sensors, and disk rotation information may be stored into memory 124 for analysis. Processor 122 may comprise any one or more of a microprocessor, digital signal processor (DSP), application specific integrated circuit (ASIC), field-programmable gate array (FPGA), or other digital logic circuitry. Moreover, processor 122 provides an operating environment for firmware, software, or combinations thereof, stored on a computer-readable medium, such as memory 124.

Memory 124 may include one or more memories for storing a variety of information. For example, one memory may contain specific configuration parameters, executable instructions, and one may contain collected data. Therefore, processor 122 may use data stored in memory 124 for controlling device operation and calibration. Memory 124 may include any one or more of a random access memory (RAM), read-only memory (ROM), electronically-erasable programmable ROM (EEPROM), flash memory, or the like.

Processor 122 may additionally control heating element 134. Based upon the instructions contained within memory 124, the heating element 134 may be selectively driven to control the temperature of one or more chambers according to desired heating profiles. Generally, heating element heats one radial section of disk 13 as the disk spins. Heating element 134 may comprise a halogen bulb and reflector for focusing heating energy on a specific area of disk 13. In other embodiments, heating element 134 may heat one or more chambers sequentially. This embodiment would require disk 13 to be stationary while a chamber is heated. In any embodiment, heating element 134 may be capable of turning on and off extremely quickly as needed.

Laser 136 is used to control valve opening which allows contents of a holding chamber to flow to another chamber on disk 13, e.g., a reaction well or process chamber. Processor 122 and supporting hardware drives laser 136 to selectively open specific valves contained with disk 13. Processor 122 may interact with a laser sensor underneath disk 13 for determining the position of the laser relative to the desired valve. When in position, processor 122 outputs signals to direct laser 136 to produce a burst of energy targeted at the valve. In some cases, the burst may last for approximately 0.5 seconds, while other embodiments may include opening times of shorter or greater duration. A laser energy and pulse duration may be controlled by processor 122 through communication with laser 136.

Processor 122 utilizes communication interface 130 to communicate with data acquisition system 21. The communication interface 130 may include a single method or combination of methods to transfer data. Some methods may include a universal serial bus (USB) port or IEEE 1394 port for hardwire connectivity with high data transfer rates. In some embodiments, a storage device may be directly attached to one of these ports for data storage for post processing. The data may be pre-processed by processor 122 and ready for viewing, or the raw data may need to be completely processed before analyzing can begin.

Communications with detection device 10 may also be accomplished by radio frequency (RF) communication or a local area network (LAN) connection. Moreover, connectivity may be achieved by direct connection or through a network access point, such as a hub or router, which may support wired or wireless communications. For example detection device 10 may transmit data on a certain RF frequency for reception by the target data acquisition device 21. Data acquisition device 21 may be, for example, a general purpose computer, a notebook computer, a handheld computing device, or an application-specific device. Further, multiple data acquisition devices may receive the data simultaneously. In other embodiments, the data acquisition device 21 may be included with detection device 10 as one integrated detection and acquisition system.

In addition, detection device 10 may be able to download updated software, firmware, and calibration data from a remote device over a network, such as the internet. Communication interface 130 may also enable processor 122 to monitor inventory report any failures. If operational problems occur, processor 122 may be able to output error information to assist a user in trouble shooting the problems by providing operational data. For example, processor 122 may provide information to help the user diagnose a failing heating element or a synchronization problem.

Power source 132 delivers operating power to the components of device 10. Power source 132 may utilize electricity from a standard 115 Volt electrical outlet or include a battery and a power generation circuit to produce the operating power. In some embodiments, the battery may be rechargeable to allow extended operation. For example, device 10 may be portable to detection of biological samples in an emergency, such as a disaster area. Recharging may be accomplished through the 115 Volt electrical outlet. In other embodiments, traditional batteries may be used.

Figure 9:
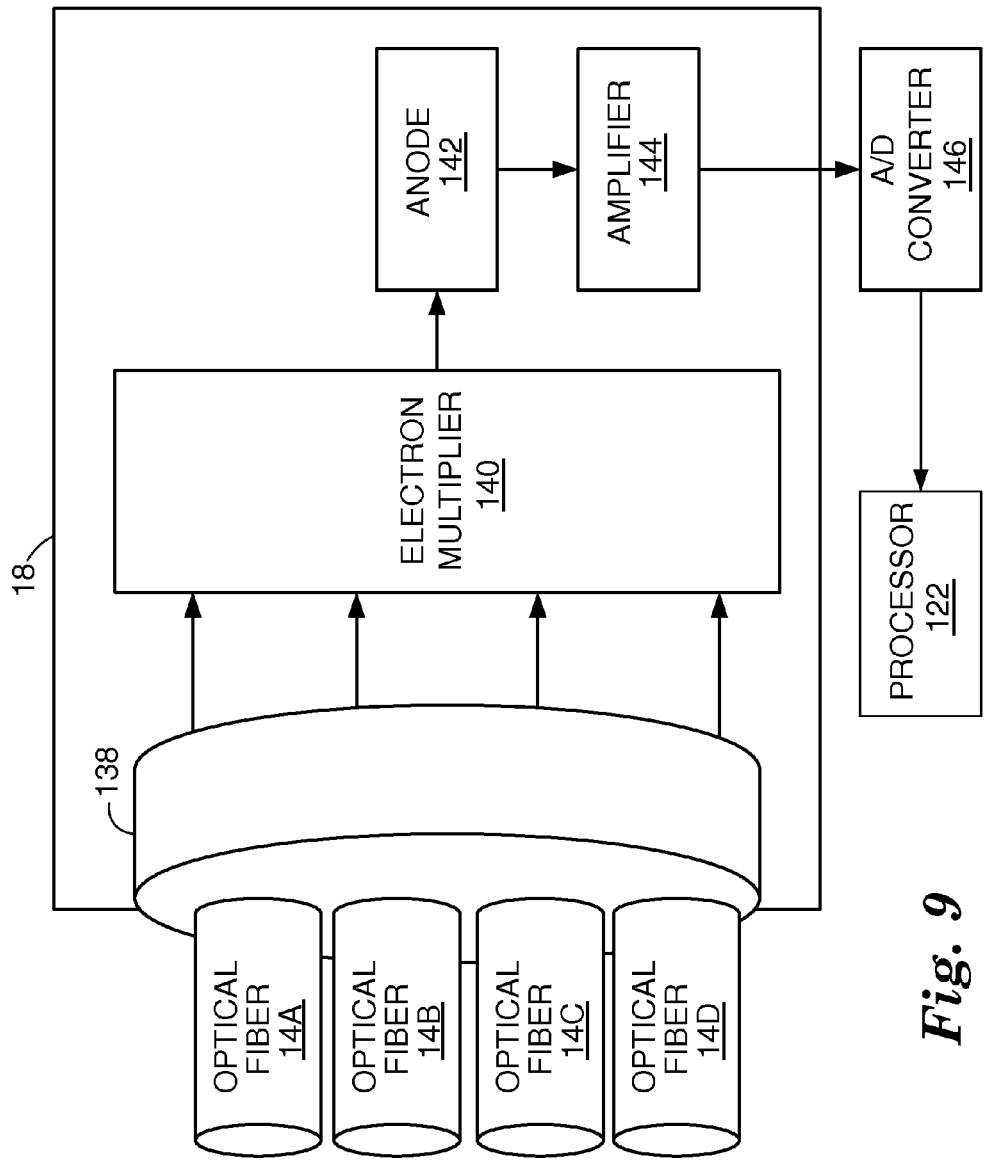
FIG. 9 is a block diagram of a single detector coupled to four optical fibers of the optical fiber bundle.

FIG. 9 is a functional block diagram of the single detector 18 coupled to four optical fibers of the optical fiber bundle. In this embodiment, detector 18 is a photomultiplier tube. Each leg of fiber optic bundle 14, optical fiber 14A, optical fiber 14B, optical fiber 14C and optical fiber 14D, couples to an optical input interface 138 of detector 18. In this manner, light carried by any of optical fibers 14 is provided to a single optical input interface 138 of detector 18. The optical input interface 138 provides the aggregate light to electron multiplier 140. Anode 142 collects the electrons and produces a corresponding analog signal as output signal.

In other words, as shown, the optical fibers 14 fit within the input optical aperture for detector 18. Consequently, detector 18 may be used to detect light from each leg of optic bundle 14 simultaneously. Optical input interface 138 provides the light to electron multiplier 140. For a photomultiplier tube, the photons from the optical fibers first hit a photoemissive cathode, which in turn releases photoelectrons. The photoelectrons then cascade by hitting a series of dynodes, more photoelectrons being emitted upon contact with each dynode. The resulting group of electrons has essentially multiplied the small light signals originally transmitted by the optical fibers 14. The increased number of electrons finally is collected by anode 142. This current from anode 142 is transferred by a current to voltage amplifier 144 as an analog output signal which is representative of the optical florescent signals from the sample provided by the plurality of optical modules 16.

Control unit 23 includes an analog to digital (A/D) converter 146 converts the analog signal to a stream of sampled digital data, i.e., a digital signal. Processor 122 receives the digital signal and stores the sampled data in memory 124 for communication to data acquisition device 21, as described in above. In some embodiments, A/D converter 146 may be contained within detector 18 instead of control unit 23.

In this manner, a single detector 18 may be utilized to collect all light from the optic bundle 14 and produce a signal representative thereof. Once the signal is amplified by amplifier 144 and converted to a digital signal, it may be digitally separated into data corresponding to the light collected by each individual optical modules 16. The entire (i.e., aggregate) signal may be separated by frequency range into each detected signal representative of each fluorescence. These frequencies may be separated by a digital filter applied by data acquisition device 21 or within device 10.

In other embodiments, the amplified signal may be separated by frequency using analog filters and sent to separate channels before A/D converter 146. Each channel may then be separately digitized and sent to the data acquisition device. In either case, the single detector is able to capture all florescence information from each optical module 16. Data acquisition device 21 may then plot and analyze the signal acquired from each chamber of disk 13 in real-time without the need for multiple detectors.

In some embodiments, detector 18 may not be a photomultiplier tube. In general, detector 18 may be any type of analog or digital detection device capable of capturing light from multiple legs of an optical delivery mechanism, i.e., fiber bundle 14, and producing a transmittable representation of the captured light.

Figure 10:
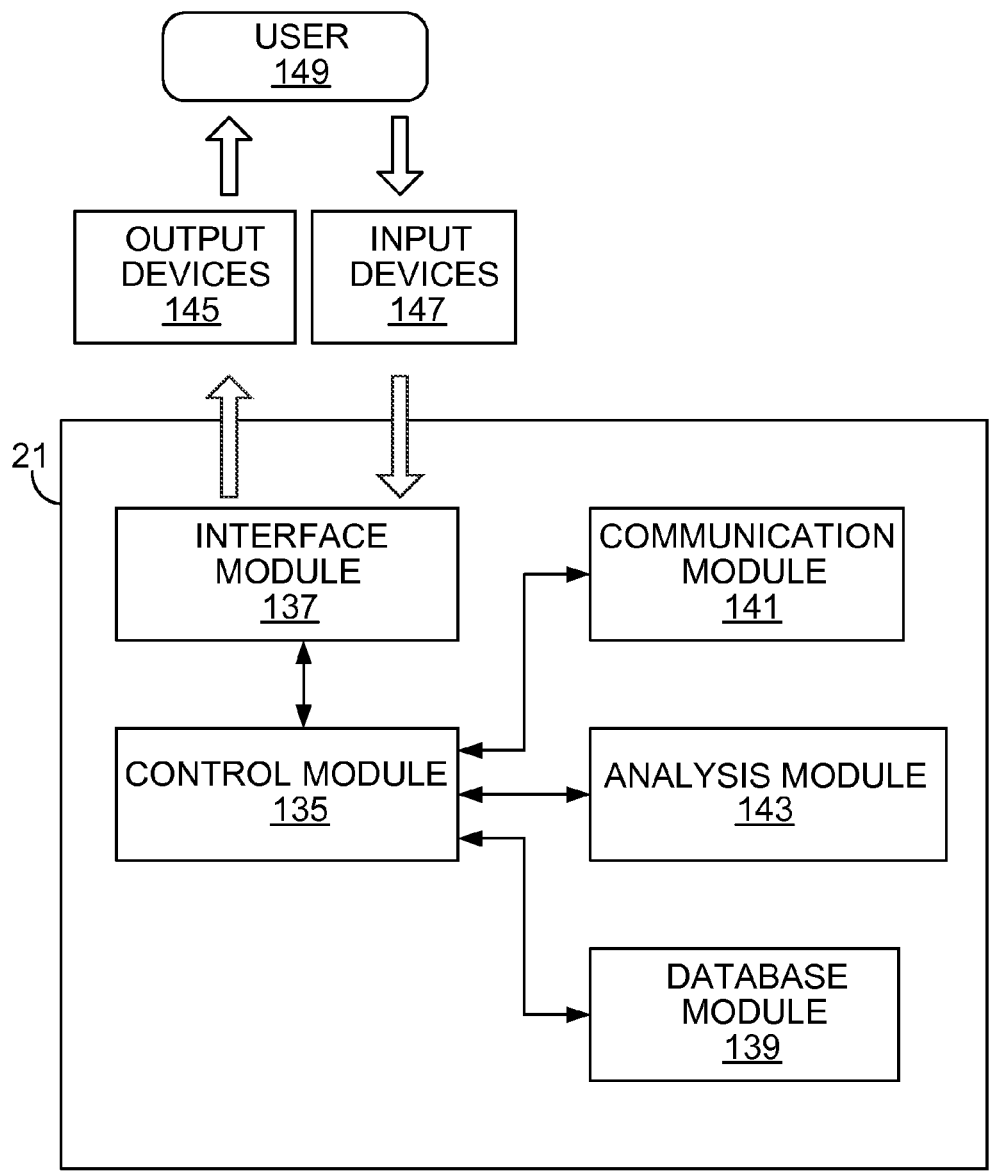
FIG. 10 is a functional block diagram illustrating an example data amplification device.

FIG. 10 is a functional block diagram illustrating further details of an exemplary data acquisition device 21, which may be a general computing device, such as a desktop computer, executing software on one or more microprocessors. In the illustrated embodiment, data acquisition device 21 may be viewed functionally as including a control module 135, an interface module 137, a database module 139, a communication module 141, and an analysis module 143.

Interface module 137 represents software and hardware necessary for interacting with a user, e.g., for receiving input from a user 149 and for outputting information to the user 149. Interface module 137 may receive input from input devices 147 and output data to output devices 145 that enable a user to interact with system 10. For example, user 149 may change operational parameters of detection device 12 and data acquisition device 21 and manipulate data stored in database module 139. Moreover, user 149 may interact with interface module 137 to initiate real-time nucleic acid amplification of samples 17 stored within chambers of disk 13. Further, user 149 may interact with data acquisition device 21 to view and manipulate the acquired data. During this process, interface module 137 may present a user with user interface screens for interacting with data acquisition device 21, including, for example, the exemplary user interface screens shown in FIGS. 18-20, 23. Exemplary input devices 147 include a keyboard, a touchscreen, a mouse, a microphone, and the like. Output devices 145 may include, for example, an LCD screen, an LED array, a CRT screen, or a touchscreen display.

Control module 135 represents control logic that, in response to input received from user 149 via interface module 137, directs the operation of fluorescence detection device 12. For example, control module 135 may comprise software instructions that, when executed, provide control logic for communicating commands to control unit 23 of fluorescence detection device 12 to commence nucleic acid amplification and data collection. Moreover, control module 135 may provide commands to request and receive buffered amplification data from control unit 23 during or upon completion of each interrogation period. Furthermore, control module 135 provides control logic for storing the buffered amplification data within database module 139, and for invoking analysis module 143 to process the data in response to commands from user 149.

Analysis module 143 receives amplification data from control module 135, processes the amplification data using spectral crosstalk correction values, and provides the processed data to interface module 137 for display. For example, analysis module 143 may calculate a corrected signal for a particular channel by subtracting from a background-corrected signal the product of a correction factor for the channel and a signal of the spectral neighbor. As another example, analysis module 143 may calculate a corrected signal for a particular channel by subtracting from a background-corrected signal the product of a correction factor for the channel and a signal of the nearest spectral neighbor.

Interface module 137 may then display the corrected data on a display of output devices 145. Interface module 137 may display the corrected data value as text, as data points on a graph, as part of a table, or the like. In other embodiments, interface module 137 may display a message based on the data on a display of output device 36. For example, analysis module 143 may interpret the data to simply mean that a certain nucleic acid is present in the sample that has undergone nucleic acid amplification. Interface module 137 may then display a message indicating the presence of this nucleic acid segment in the sample. Conversely, if no growth is not detected on a particular channel for the sample (i.e., no amplification has occurred), analysis module 143 may interpret this to indicate that no nucleic acid with a certain sequence is present in the sample, and interface module 137 may display a corresponding message.

In some embodiments, analysis module 143 or control module 135 may apply data preparation techniques, such as curve smoothing, noise reduction, or the like prior to analyzing the amplification data using crosstalk compensation.

Data acquisition device 21 may be a general-purpose workstation, desktop computer, laptop computer, a handheld computing device, a personal digital assistant (PDA), or other computing device. Data acquisition device 21 may include a microprocessor, digital signal processor (DSP), field programmable gate array (FPGA), application specific integrated circuit (ASIC) or other hardware, firmware and/or software for implementing the techniques. In other words, the analysis of PCR amplification data, as described herein, may be implemented in hardware, software, firmware, combinations thereof, or the like. If implemented in software, a computer-readable medium may store instructions, i.e., program code, that can be executed by a processor or DSP to carry out one or more of the techniques described above. For example, the computer-readable medium may comprise magnetic media, optical media, random access memory (RAM), read-only memory (ROM), non-volatile random access memory (NVRAM), electrically erasable programmable read-only memory (EEPROM), flash memory, or other media suitable for storing program code.

Figure 11:
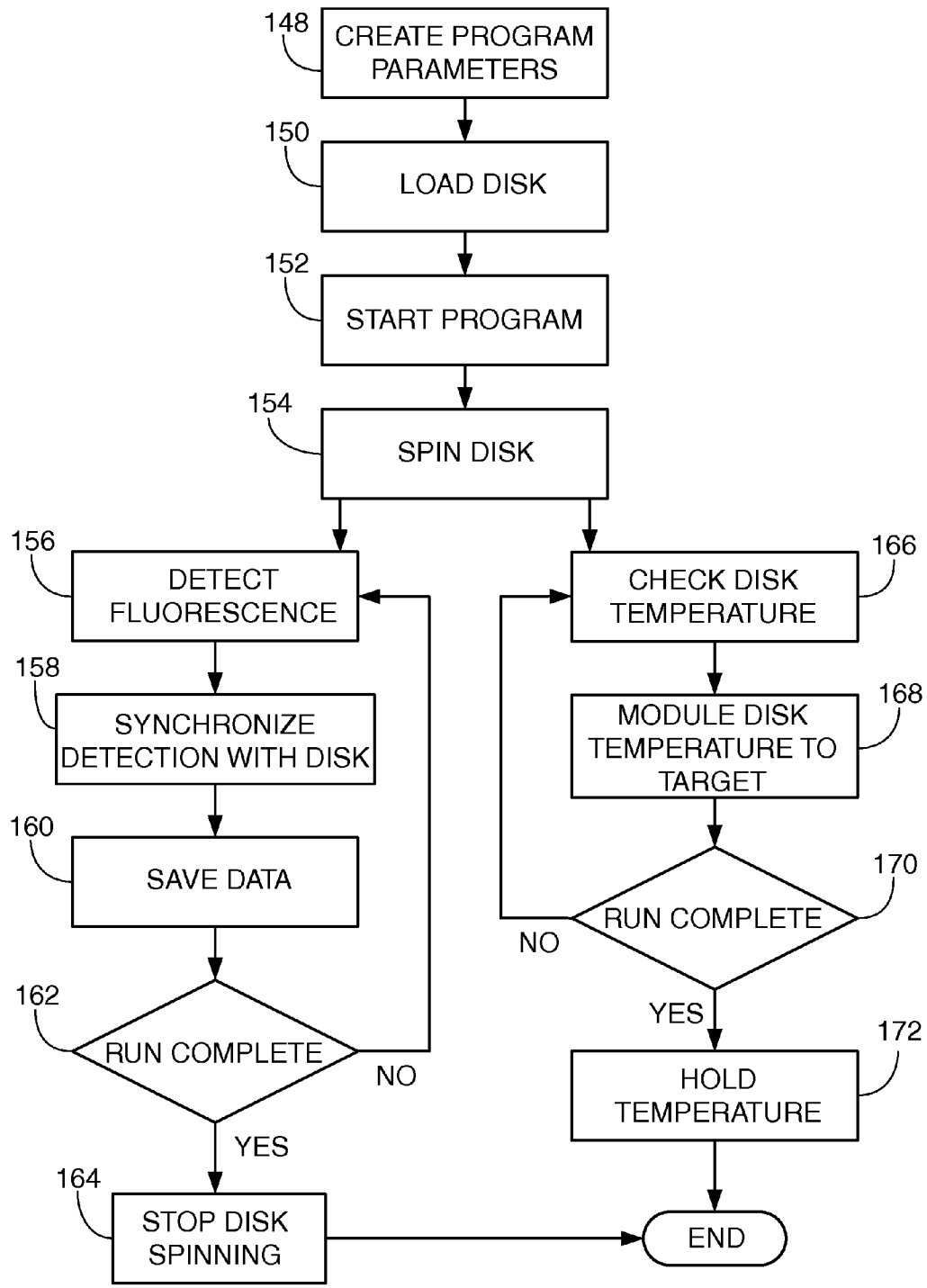
FIG. 11 is a flow diagram illustrating exemplary operation of the multiplex fluorescence detection device.

FIG. 11 is a flow diagram illustrating the operation of the multiplex fluorescence detection device 10. Initially, a user specifies program parameters on the data acquisition device 21 or via an interface with control unit 23 (148). For example, these parameters may include rotational rates and time periods for rotating disk 13, define temperature profiles for each interrogation period, sample types and sample locations on disk 13, fluorescent marker types, detector wavelengths, and the like. In some embodiments, these parameters may also include the crosstalk correction values. In other embodiments, data acquisition device 21 may be configured with the crosstalk correction values during manufacturing.

Next, the user loads disk 13 into the detection device 10 (150). Upon securing the device 10, the user starts the program (152), causing control unit 23 to control the platform 25 to begin spinning the disk (154) at the specified rate. After the disk has begun to spin, two concurrent processes may occur.

First, the detection device 10 starts to detect fluorescence from the excitation light (156) produced by one or more reactions within one or more samples. The detector 18 amplifies the fluorescence signals from each sample, which are synchronized to each respective sample and time at which the fluorescence was emitted (158). During this process, processor 122 saves the captured data to memory 124 and may communicate the data to data acquisition device 21 in real-time to monitor the progress of the run and for additional processing including application of spectral crosstalk correction values (160). Alternatively, processor 122 may save the data within device 10 until the program is complete. The processor 122 continues to detect florescence of the samples and save data until the program is complete (162). Once the run is complete, control unit 23 stops the disk from spinning (164). In some embodiments, processor 122 may itself apply the spectral crosstalk correction values as described herein, rather than data acquisition device 21.

During this process, control unit 23 monitors the disk temperature (166) and modulates the disk, or each sample, temperature to attain the target temperature for that time (168). The control unit 23 continues to monitor and control the temperatures until the program is complete (170). Once the run is complete, control unit 23 holds the temperature of the samples to a target storage temperature, usually 4 degrees Celsius (172).

The operation of device 10 may vary from the example of FIG. 11. For example, the disk revolutions per minute may be modified throughout the program, and laser 136 may be utilized to open valves between chambers on the disk to allow for multiple reactions. These steps may occur in any order within the operation, depending on the program the user defines.

Figure 12:
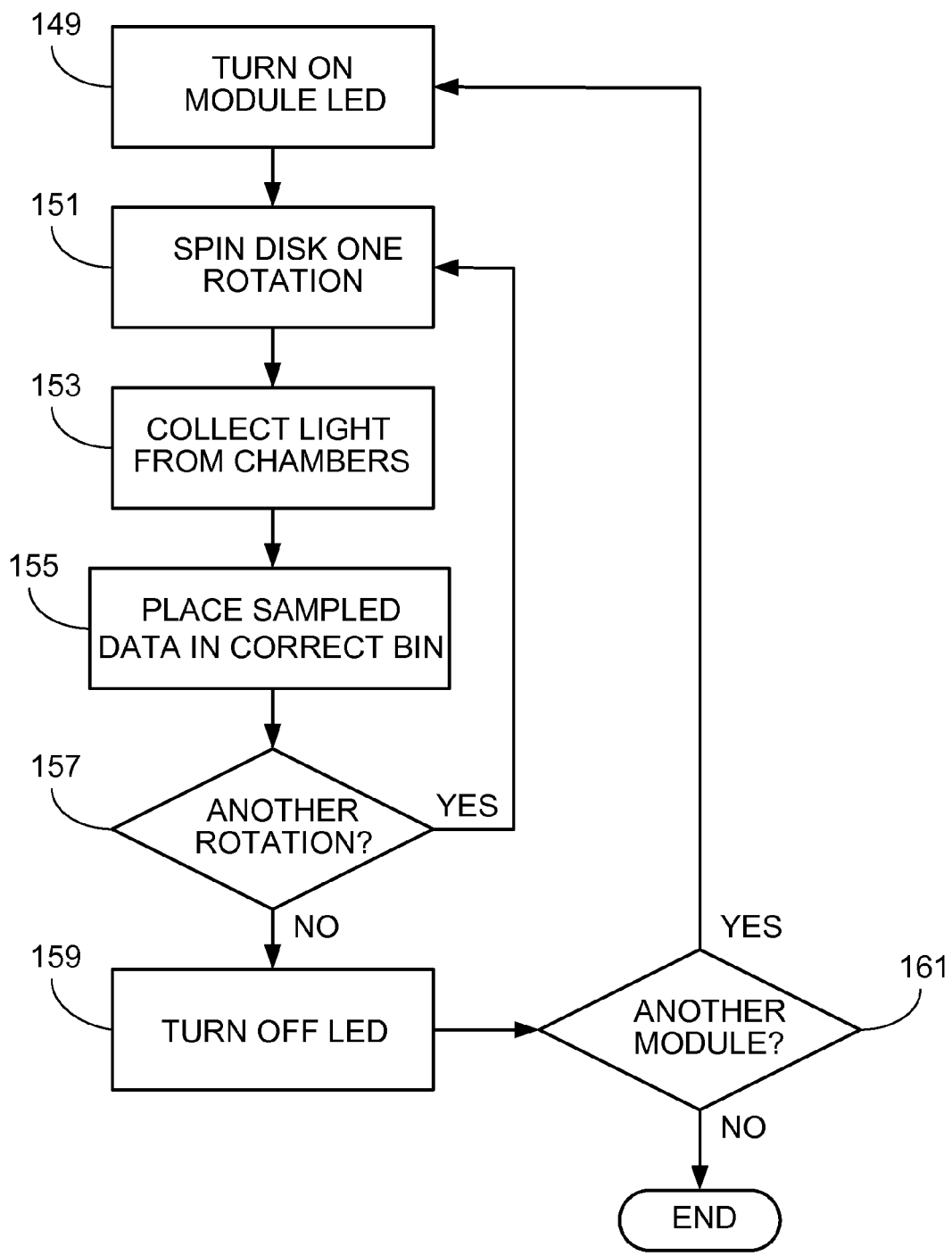
FIG. 12 is a flow diagram illustrating an exemplary method if detecting light and sampling data from the disk.

FIG. 12 is a flow diagram illustrating an exemplary method if detecting light and sampling data from the disk. Initially, a user specifies which modules will detect fluorescence from disk 13, and control unit 23 turns on the LED of a module (149). Once the LED has warmed to steady state, control unit 23 spins disk 13 one rotation at the rate of approximately 1470 revolutions per minute (151). During that rotation, the module collects light fluoresced from the process chambers of disk 13 (153), and control unit 23 places 16 samples from each process chamber in the memory BIN associated with each process chamber (155).

If disk 13 must be spun another rotation (157), control unit 23 executes another revolution of disk 13 (151). If 16 revolutions have been sampled, the module has completed detection with the LED. Therefore, each process chamber was sampled a total of 256 times and data acquisition device 21 integrates the samples to create a histogram of each process chamber. Control unit 23 turns the LED off (159). If another module must to used to continue detection (161), control unit 23 turns on the next module LED (149). If no other modules are needed to collect data, control unit 23 discontinues the collection of data from disk 13.

In some embodiments, each process chamber may be sampled more or less times. Control unit 23 may spin disk 13 at a faster rate to provide quicker results or spin disk 13 slower to acquire more samples. In other embodiments, LEDs from two or more modules may be turned on to detect fluorescence simultaneously in multiple wavelengths.

Figure 13:
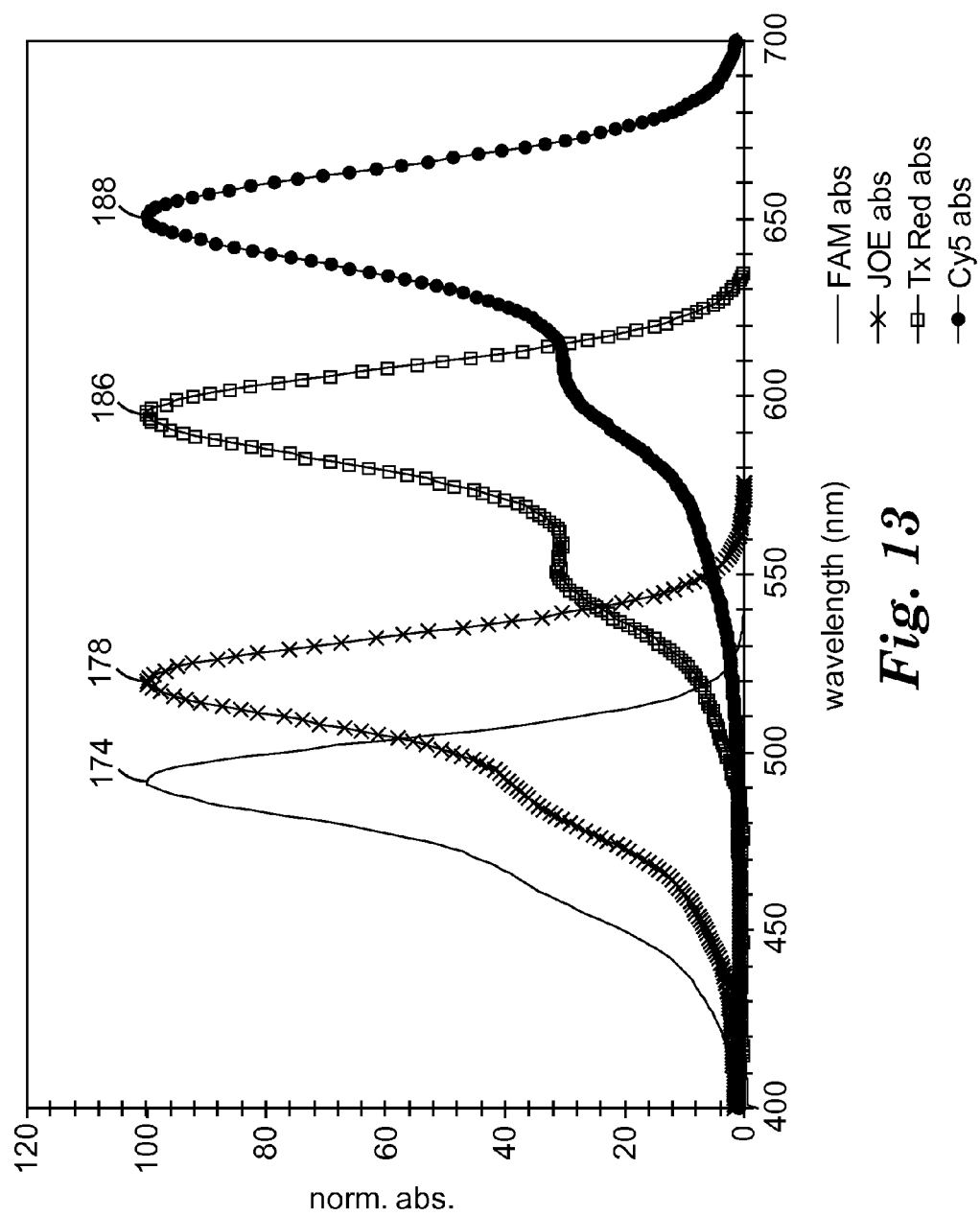
FIGS. 13 and 14 are graphs showing the absorption and emission spectra of commonly used fluorescent dyes that may be utilized for multiplex PCR.
Figure 14:
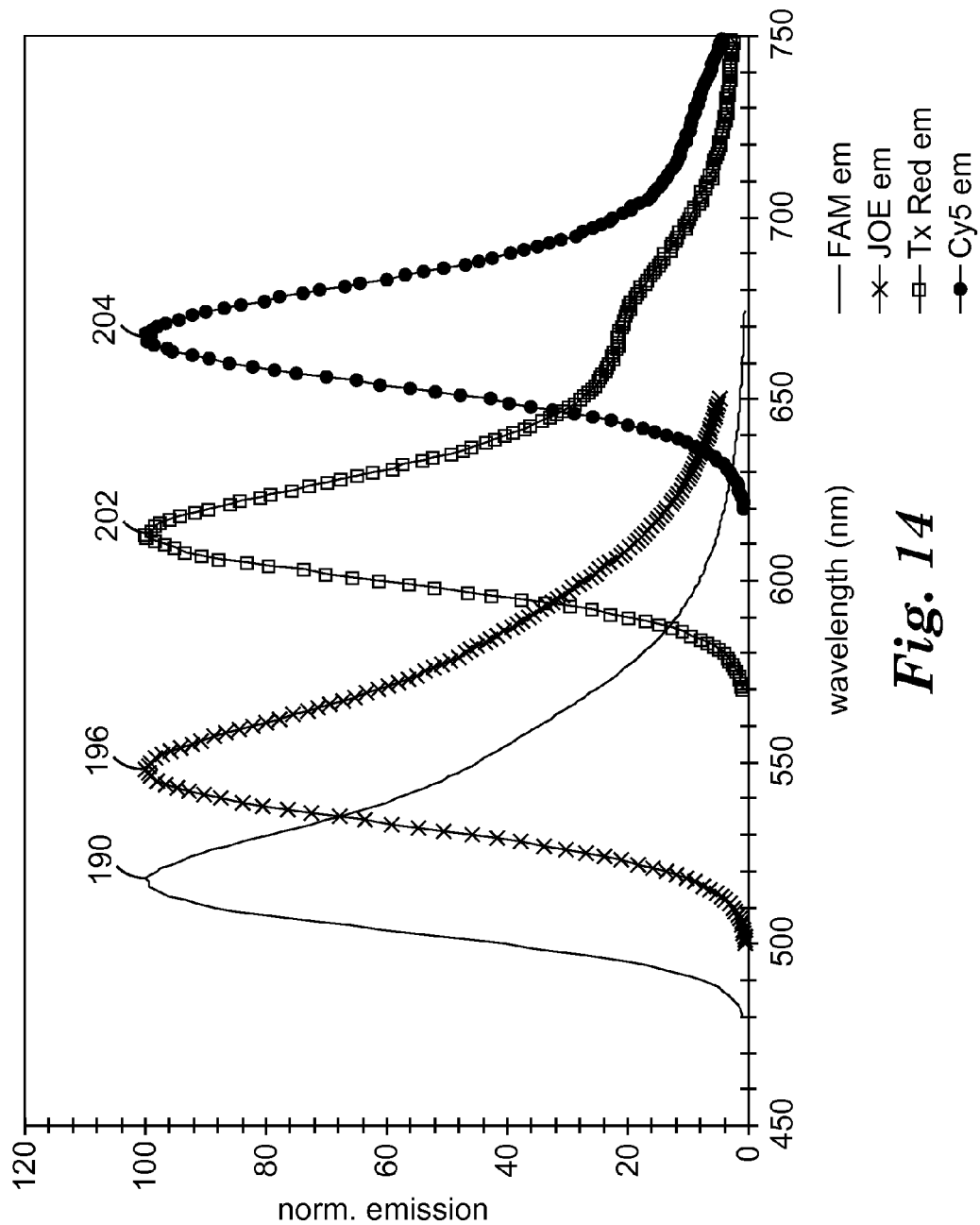

FIGS. 13 and 14 show the absorption and emission spectra, respectively, of commonly used fluorescent dyes that may be utilized with device 10 for multiplex PCR. In these examples, FIG. 13 shows that the absorption maxima of the dyes vary from 480-620 nm, and FIG. 14 shows that the resulting emission maxima vary from 520-670 nm. The absorption spectra signals for each dye in FIG. 13 are numbered as FAM 174, JOE 178, Tx Red 186, and Cy5 188. The emission spectra signals in FIG. 14 are FAM 190 JOE 196, Tx Red 202, and Cy5 204. The filters and dyes shown herein are used for purposes of example. Other example dyes that may be additionally or alternatively used include Sybr, TET, HEX, ROX, VIC, Tamra, and Cy3. FAM, HEX, JOE, VIC, TET, ROX are trademarks of Applera, Norwalk, Calif. Tamra is a trademark of AnaSpec, San Jose, Calif. Texas Red is a trademark of Molecular Probes. Cy3 and Cy5 are trademarks of Amersham, Buckinghamshire, United Kingdom.

The fluorescent dyes are spectrally spaced closely to one another, and are differentiated by the use of optical filters to minimize signal carry-over from one dye to another. Due to the wide absorption and emission bands of typical fluorophores, the filters may reduce but not eliminate the spectral crosstalk. The spectral crosstalk of a strongly amplifying signal will often result in a growth on a neighboring channel and may be interpreted as a growth on a target channel. The techniques described herein use a set of correction factors determined from a calibration procedure to automatically remove the interfering signals.

Table 1 lists exemplary components that may be used in a four-channel multiplex fluorescence detection device 10 (FIG. 1) for a variety of fluorescent dyes. Table 1 summarizes the choice of filters used in the different optical modules. The bandwidths of the excitation and emission filters are shown below.

TABLE 1

| Channel/ Optical Module Number | LED | Filter Name | Excitation Filter | Detection/ Emission Filter | Compatible Dyes |
|---|---|---|---|---|---|
| 1 | Blue | "FAM" | 475 ± 20 nm | 520 ± 10 nm | FAM, Sybr Green |
| 2 | Green | "JOE" | 520 ± 10 nm | 560 ± 10 nm | HEX, JOE, VIC, TET |
| 3 | Orange | "TxRed" | 580 ± 10 nm | 610 ± 10 nm | TAMRA, ROX, Texas Red, Cy3 |
| 4 | Red | "Cy5" | 635 ± 10 nm | 680 ± 20 nm | Cy5 |

The filters were chosen to have a small bandwidth (nominally 10 nm at full width half maximum of the peak) to maximize the signal from each dye, without detecting neighboring dyes. The dyes, however, have fairly wide bands, which may lead to crosstalk from neighboring dyes. For example, for detection of the FAM labeled probe, excitation is centered at 475 nm, which is near 50% normalized absorption intensity, but also has 10-20% normalized absorption intensity for the HEX, HOE, and TET probes. Detection of the FAM probe is centered at 520 nm (100% normalized emission intensity), which also covers 10-20% normalized emission intensity of the HEX, Joe, and TET probes. It is also evident based on the absorption and emission spectra shown in FIGS. 13 and 14 that there would be very little crosstalk of the FAM probe onto the Texas Red ("TxRed") and Cy5 channels because the FAM module filters do not overlap the spectra of those dyes.

For the other modules, the same logic applies. There may be significant crosstalk from the target dyes of interest onto the neighboring modules. The crosstalk on the Texas Red channel is contributed by the overlapping absorption band of the Cy5 dye, and the crosstalk on the Cy5 channel is due to the overlap of the Texas Red absorption and emission bands.

The data shown in the absorption and emission plots of FIGS. 13-14 are obtained based on analysis of pure dyes only. Once dye-labeled probes are produced, there will be significant changes to the spectra due to the changes in the electronic density surrounding the fluorophore by the oligonucleotide structure of the probe. The changes, in general, shift the absorption and emission bands to longer wavelengths, but happen in various amounts due to the specific nucleotide sequence specific for the probe of interest. Therefore, it may be important to calibrate the spectral compensation with amplification data, such as real-time PCR data, with the appropriate probes in a series of single-plex reactions. All channels may be scanned for each reaction even though only one target is present, to quantify the amount of crosstalk of that probe into the neighboring modules. The calibration procedure calculates a crosstalk correction factor, which is applied to multiplex data to eliminate the crosstalk.

EXAMPLES

Example 1

In one example, a 96 chamber disk was filled with different concentrations of FAM and ROX dye diluted in standard PCR reaction buffer. Four replicates of each dye were added in a 2× dilution series, starting from 200 nM FAM and 2000 nM ROX. Each sample volume was 10 L. Chamber 82 had a mixture of 5 μL of 200 nM FAM and 5 μL Of 2000 nM ROX. Device 10 was constructed as a two-channel multiplex PCR detection device having two optical modules 16 for detection of the dyes.

The first optical module (called the FAM module) contained a blue LED, 475 nm excitation filter and a 520 nm detection filter. The second optical module (called the ROX module) contained a green LED with a 560 nm excitation filter and a 610 nm detection filter. Another option would be to incorporate an orange LED and an excitation filter at 580 nm to optimize for ROX detection.

A PCR amplification was conducted, and fluorescent signals from the samples were multiplexed into a bifurcated fiber optic bundle. The fiber bundle was interfaced with a single detector, specifically a photomultiplier tube (PMT). Data was collected by a National Instruments data acquisition (DAQ) board interfaced with a Visual Basic data acquisition program executing on a general-purpose computer. Data was acquired while the disk was spinning at 1000 revolutions per minute (nominally). The FAM module and the ROX module were sequentially used to interrogate the samples. Each scan consisted of an average of 50 rotations. The raw data from the two optical modules is shown in FIGS. 15A and 15B.

Figure 15A:
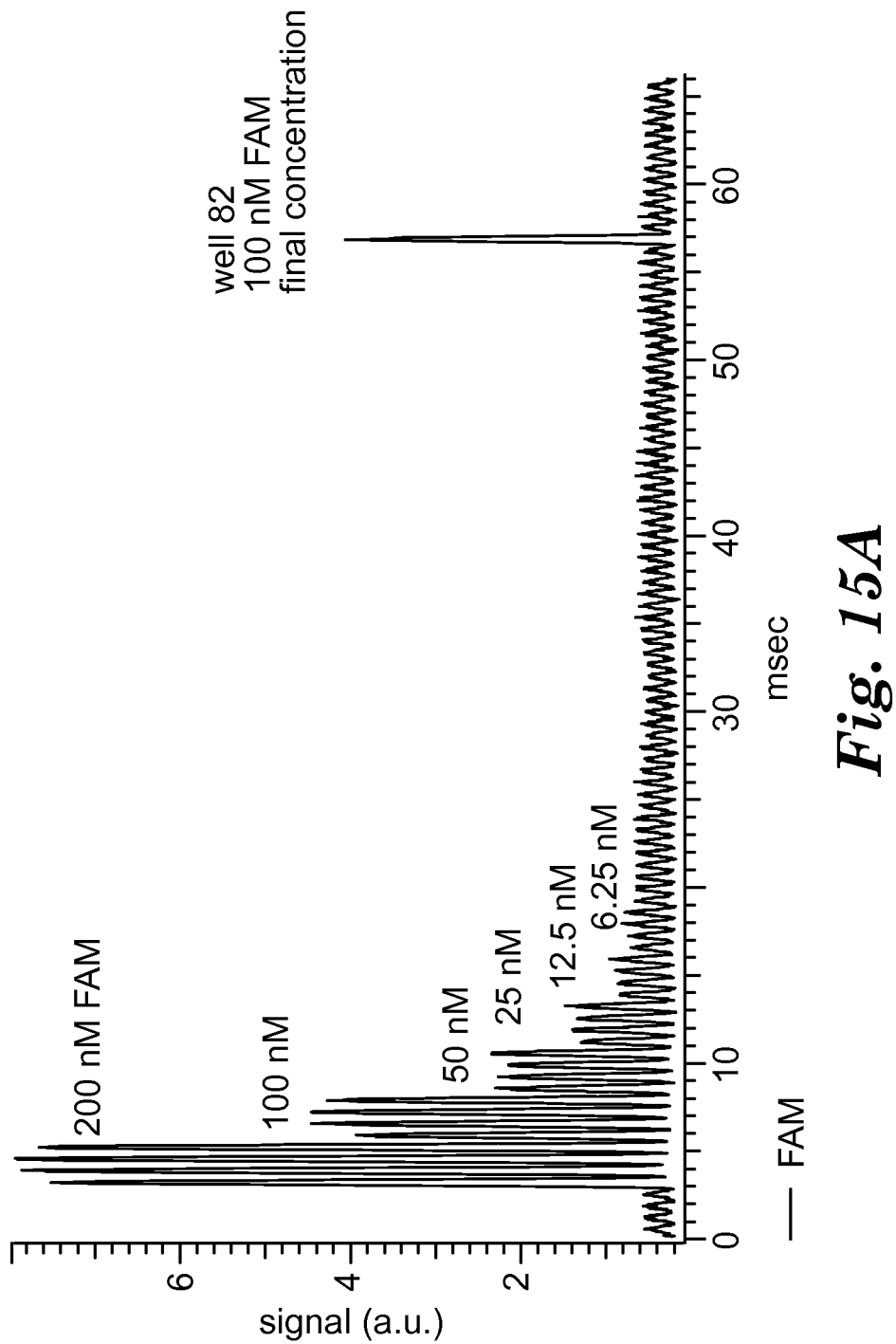
FIGS. 15A and 15B illustrate raw data acquired from two exemplary detection modules with a single detector during a PCR amplification.
Figure 15B:
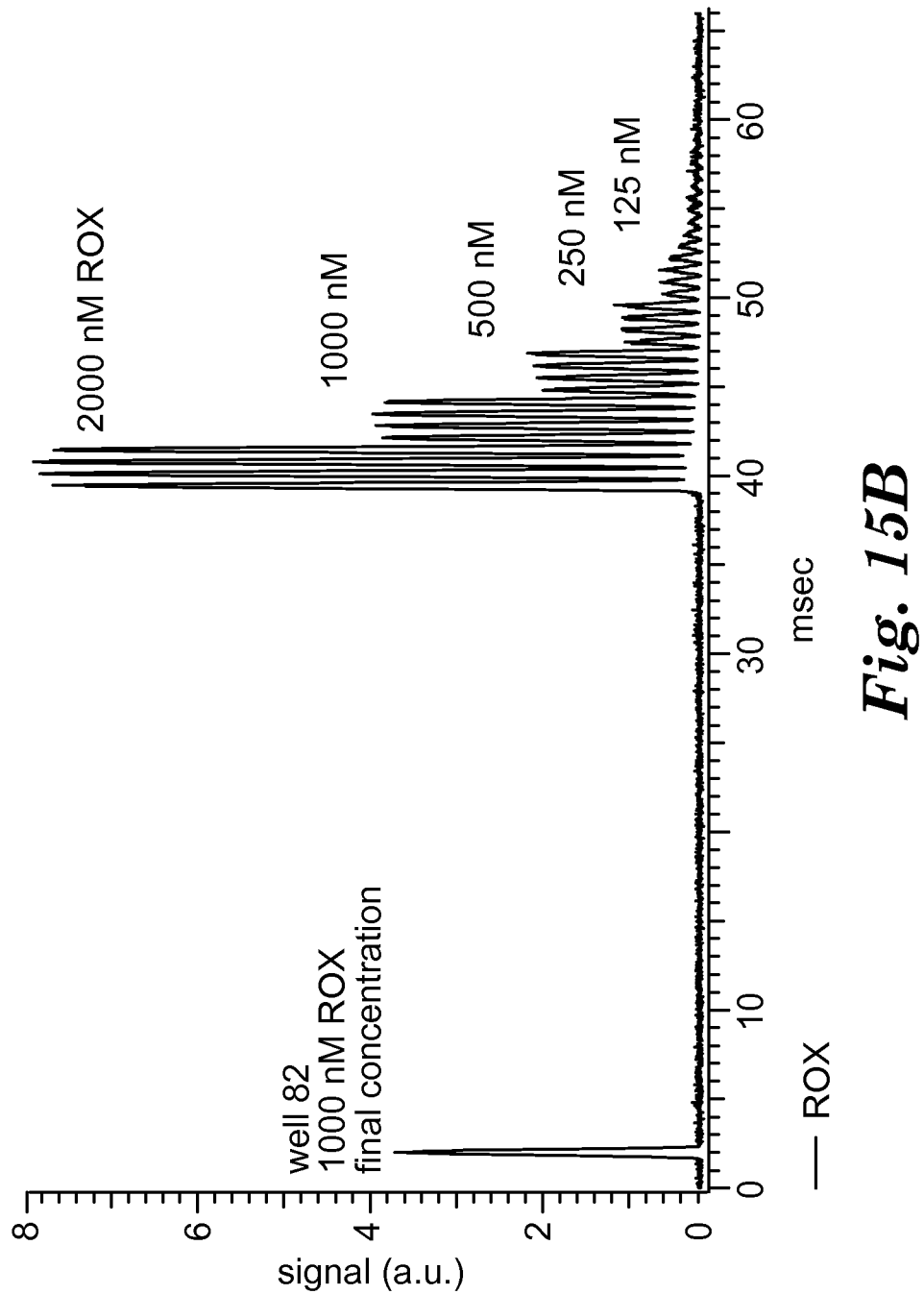

The graph in FIG. 15A was acquired by powering the LED in the FAM module, and the graph in FIG. 15B was acquired by powering the LED in the ROX module.

During the amplification, the collected data clearly showed that there was a time offset associated with optical modules being physically located over different chambers at any one time. An offset value was calculated by determining the time offset between optical modules 1 and 2 for a particular chamber, i.e., chamber 82 in this case. In other words, the time offset indicates the amount of time delay between data captured by the FAM module and data captured by the ROX module for the same chamber.

Figure 16:
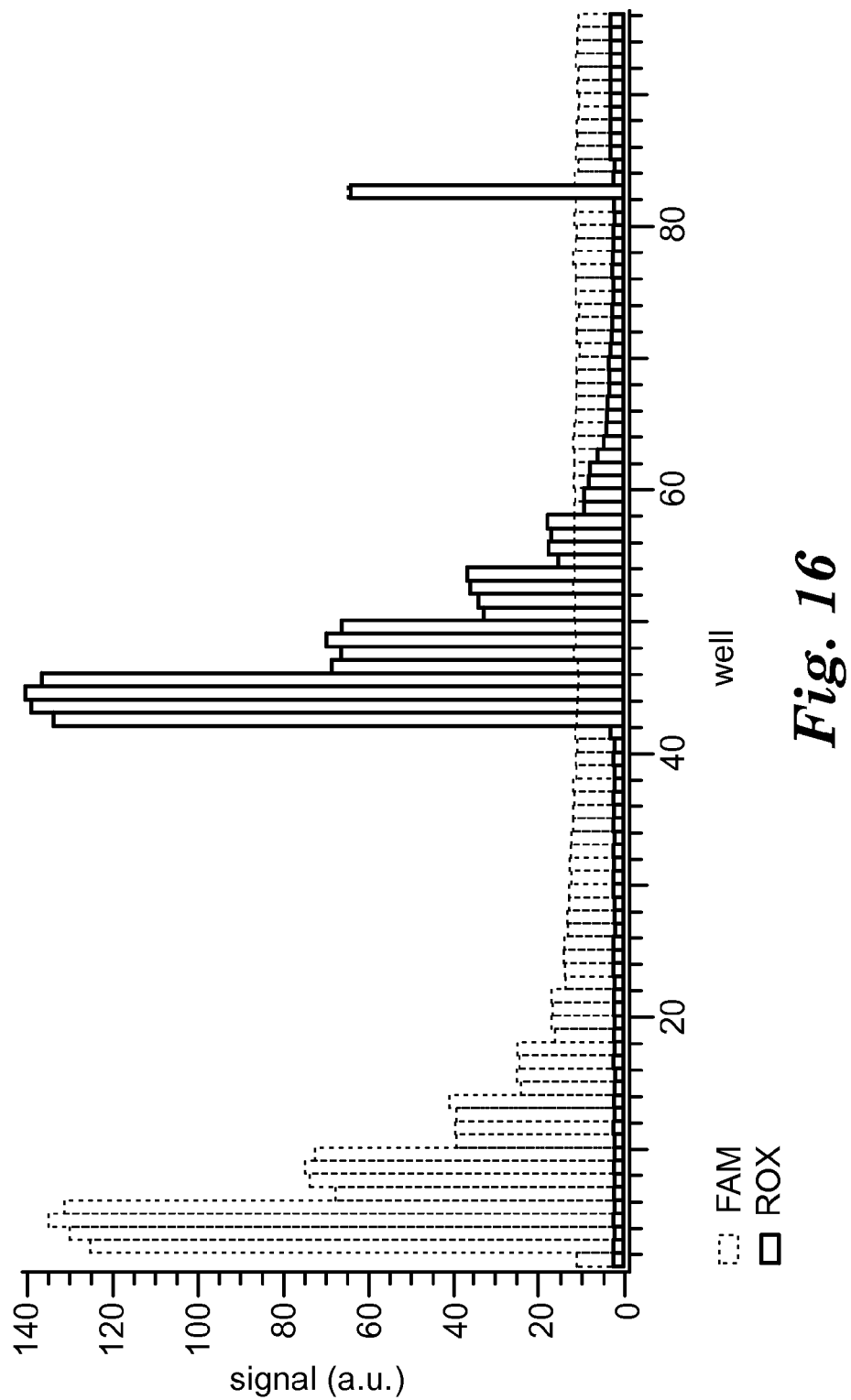
FIG. 16 is a graph that shows the data once adjusted for a time offset.

FIG. 16 is a graph that shows the offset-subtracted integrated data for each chamber. FAM is indicated by dotted line bars, ROX is indicated by solid line bars, and the ROX data is placed over the FAM data. The data showed that there was no signal from the ROX dye on optical module 1 and no signal from the FAM dye on optical module 2. There was a higher background on optical module 1, which may be rectified by using an optimized set of filters. The data was analyzed to determine the limit of detection (LOD), described as the signal equivalent to the baseline noise level. The baseline noise level was defined as the average of ten scans of a blank chamber plus 3 times the standard deviation.

Figure 17A:
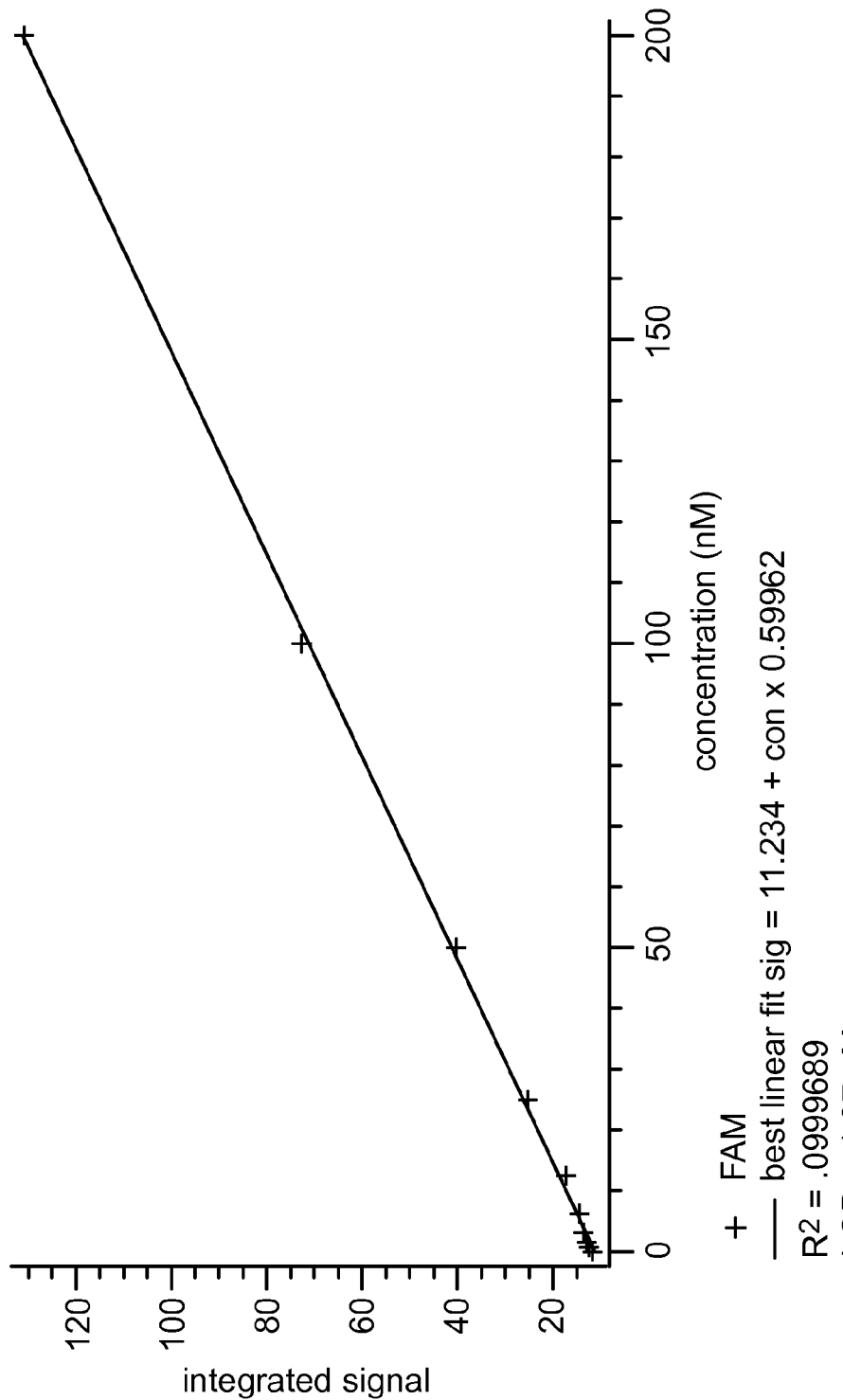
FIGS. 17A and 17B show a limit of detection (LOD) for the data received from two exemplary detection modules.
Figure 17B:
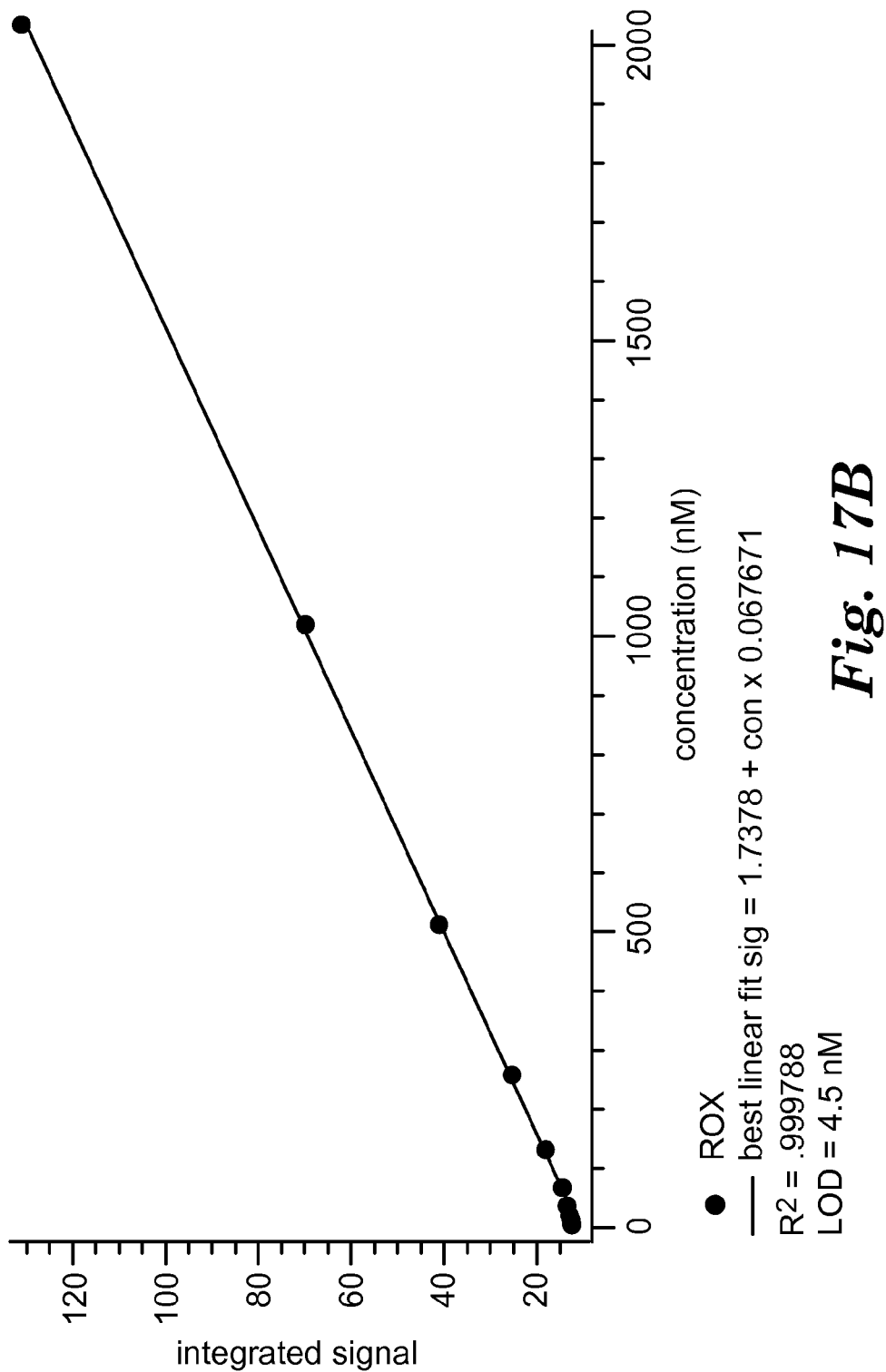

The LOD was determined by a linear least squares fit of the integrated signal plotted against the concentration of the FAM and ROX standards. The LOD of the FAM and ROX modules were calculated to be 1 and 4 nM, respectively, as shown in FIGS. 17A and 16B.

Figure 18:
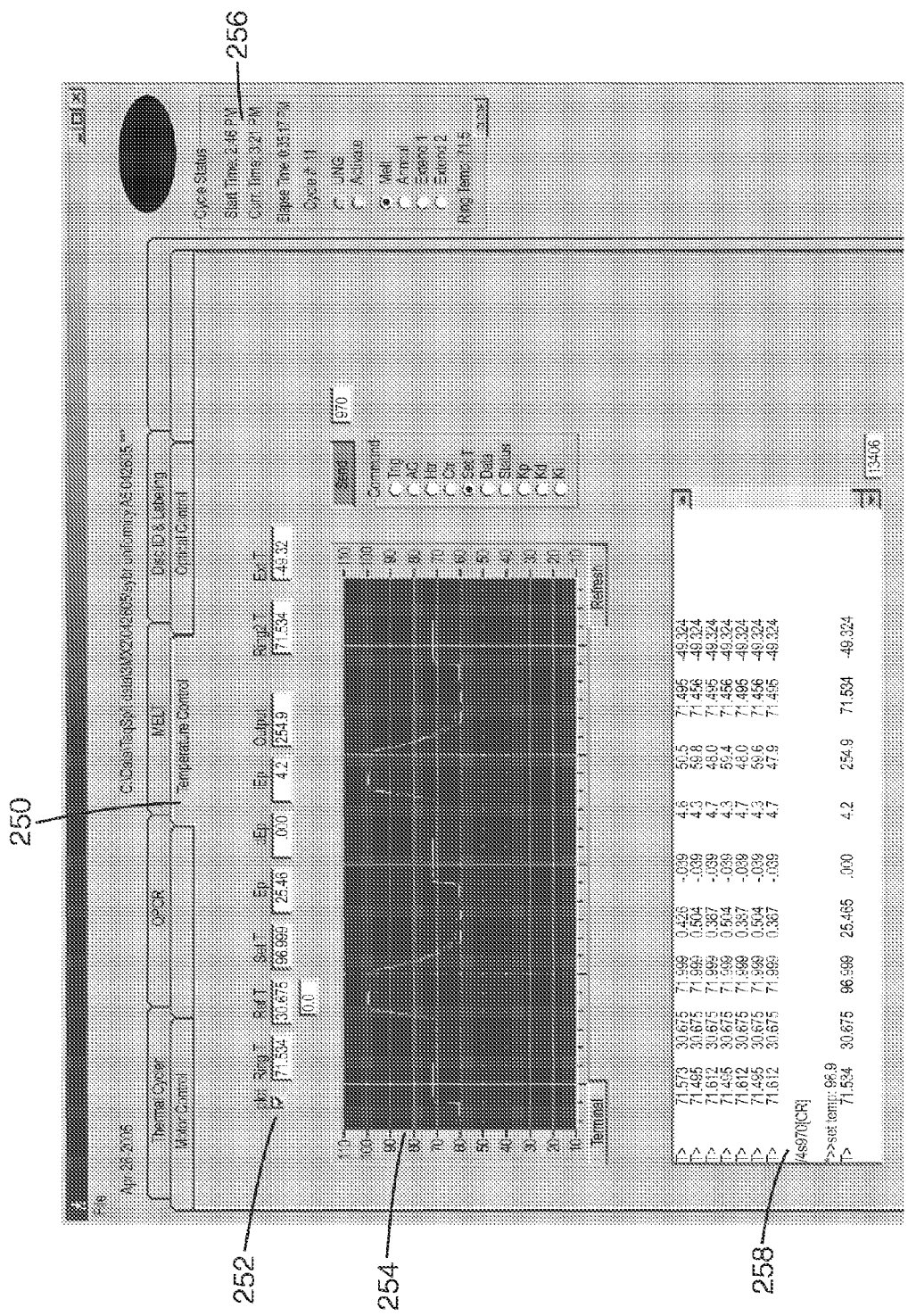
FIG. 18 is an exemplary screen shot of a temperature control user interface.

FIG. 18 is an exemplary screen shot of a temperature control user interface. Temperature control screen 250 is highlighted and shows temperature controls 252. Temperature graph 254 outputs temperature readings while status indicator 256 displays general information. Message window 258 displays commands when running detection device 10.

The technician may select temperature control screen 250 to view temperature information from device 10. Temperature control screen 250 is one of several screens which may be selected to display information associated with the operation of control unit 23 or data acquisition device 21. Screen 250 includes temperature controls 252 which display numerical information to the technician. Temperature graph 254 displays graphical temperature information as a graph of temperature as a function of time. In some embodiments, the technician may manually change the values located within temperature controls 252.

Status indicator 256 is always visible to the technician. Status indicator 256 displays relevant operational times, cycle number, temperature and other important information. Message window 258 displays current commands to control unit 23. Window 258 includes a scroll bar for locating any command delivered to control unit 23 during device 10 operation. In some embodiments, message window 258 may display error information or other important information to the technician.

Figure 19:
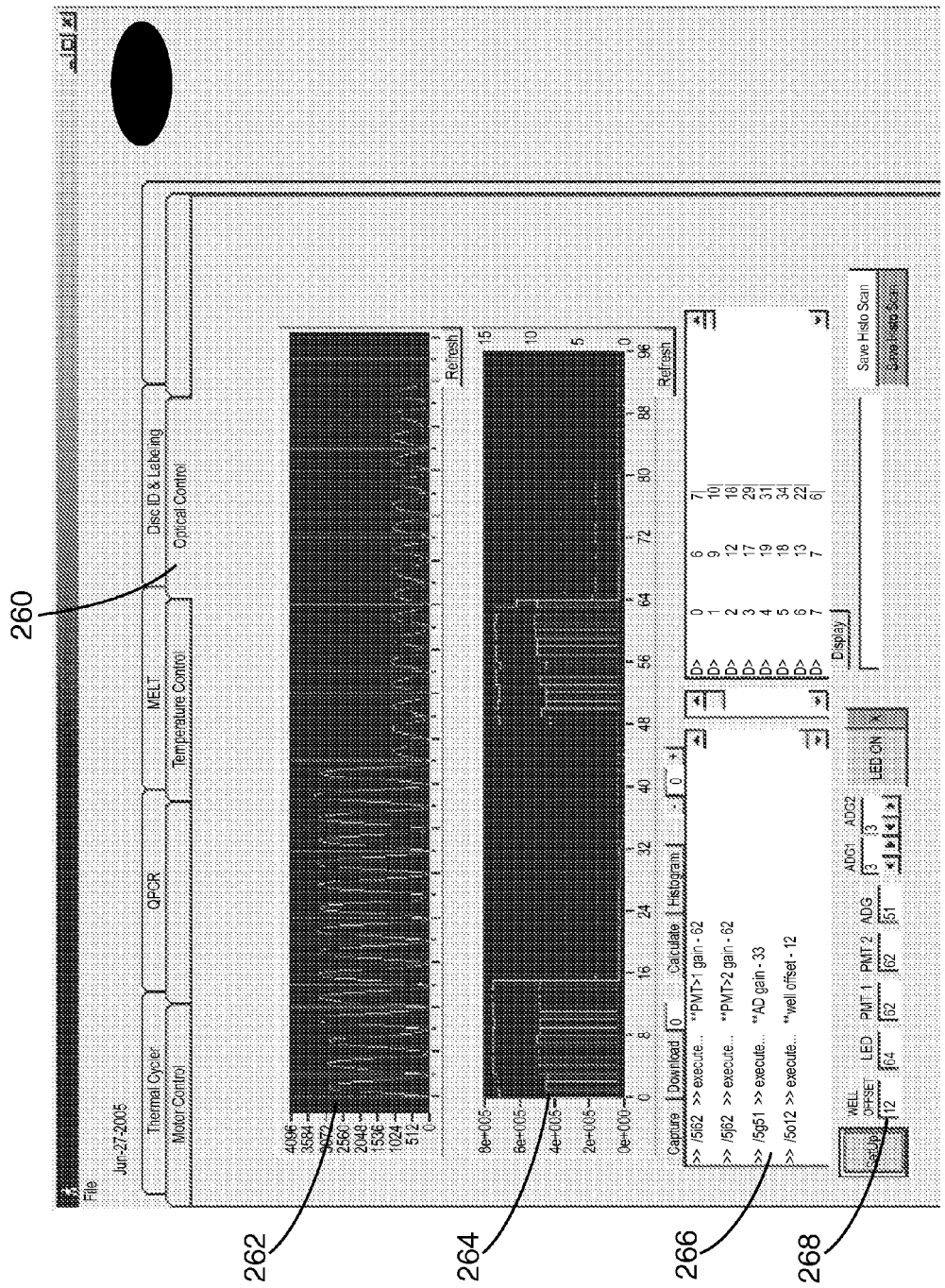
FIG. 19 is an exemplary screen shot of an optical control user interface.

FIG. 19 is an exemplary screen shot of an optical control user interface. Optical control screen 260 is highlighted and shows signal graph 262. Histogram 264 shows the integrated signal of each process chamber. Screen 260 also includes message window 266 and offset control 268.

Signal graph 262 displays the raw optical data detected by detection device 10. The signal displayed on graph 262 is the raw signal from optical modules 48, 52 and 56 and includes interrogation periods that correspond to the signal change between process chambers. The technician may change offset control 268 to match the binning of signal into appropriate bins representing each process chamber with the signal waveform. The loss of signal between each peak represents detection of light from disk 13 between each process chamber. The corresponding signal is integrated to produce histogram 264 which displays the detected signal from each of 96 process chambers. Control unit 23 integrates 16 samples from a process chamber in each of 16 rotations of disk 13. Histogram 264 therefore contains 256 samples of the contents in each samples process chamber. In some embodiments, software may automatically adjust offset control 268 by recognizing elements of the raw signal waveform. Message window 266 displays command information and error messages relating to optical control and light detection.

Figure 20:
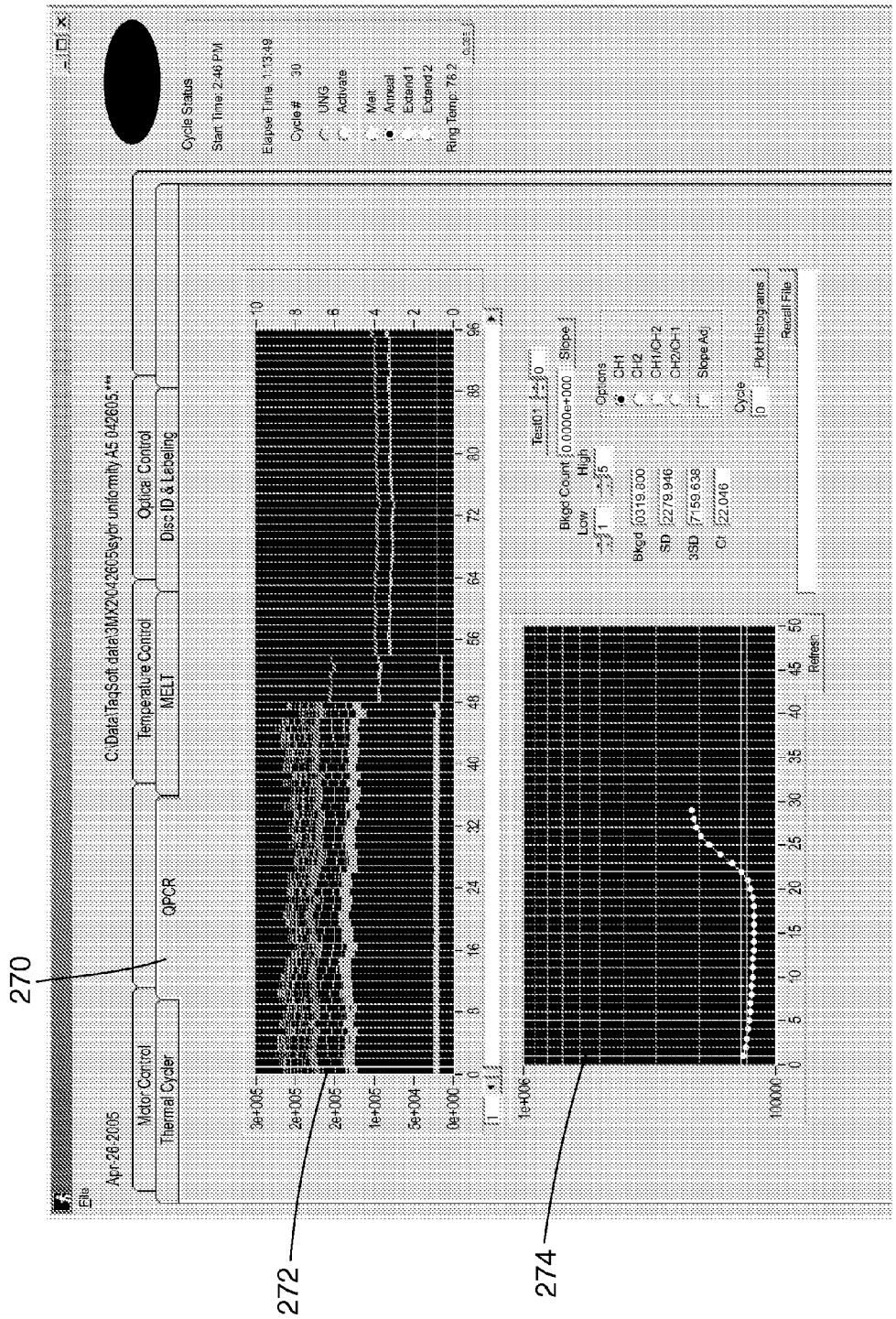
FIG. 20 is an exemplary screen shot of a real-time PCR user interface.

FIG. 20 is an exemplary screen shot of a user interface. Data screen 270 is highlighted and shows histogram 272 and product graph 274. Screen 270 shows the real-time data being collected from the process chambers of disk 13. Histogram 272 displays the integrated signal for each process chamber while product graph 274 displays the amount of amplified product as a function of number of interrogation period. In other embodiments, results for the process chambers may vary under different applications.

Figure 21:
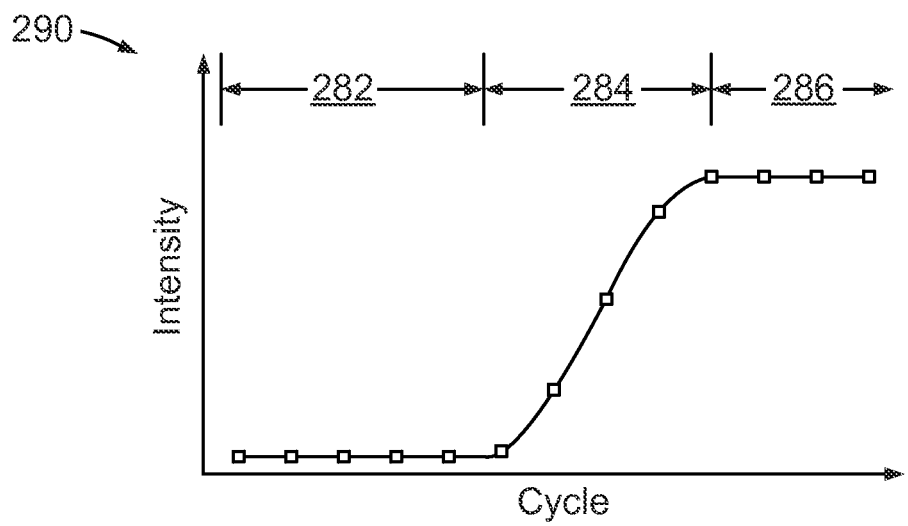
FIG. 21 is a graph illustrating a PCR amplification curve for an example nucleic acid sample.

FIG. 21 is a graph illustrating a PCR amplification curve for an example nucleic acid sample. Data acquisition device 21 may also convert the data from detector 18 for a plurality of PCR cycles in a single PCR amplification session into an amplification curve, such as amplification curve 280 shown in FIG. 21. For a typical PCR amplification session, amplification curve 280 represents the amplification of a sample sensed by fluorescence for each of a plurality of PCR cycles. The amplification curve 280 may include single fluorescence intensity value for each of the plurality of PCR cycles, with a curve fit to the data. The curve may be fit using, for example, linear regression, or may simply connect fluorescence data from adjacent interrogation periods with a smoothed or non-smoothed line. In other embodiments, the amplification curve 280 may include more than one fluorescence intensity value for each of the plurality of PCR cycles. The amplification curve for a single PCR amplification session may generally be divided into approximately three regions: the baseline period 282, the growth period 284 and the plateau period 286.

In some embodiments, data acquisition device 21 may apply wavelet transformation to the amplification data or amplification curve 280 to determine a point along the amplification curve, referred to as a threshold cycle (denoted Ct) or a $T_{max}$ value, which is a PCR cycle corresponding to a point within growth period 284 of the amplification data or amplification curve 280. In one example embodiment, wavelet transformation of the amplification data or amplification curve 280 produces a interrogation period-frequency representation of the amplification curve 280, which in general has complicated interrogation period dependence. After performing the wavelet transform, data acquisition device 21 identifies a $T_{max}$ value as a interrogation period value within the transformed amplification data at which one or more frequency components of the transformed amplification data have the largest magnitude. That is, data acquisition device 21 applies wavelet transformation to the amplification data to decompose the amplification data into a series of basis functions (i.e. wavelets). This allows the amplification data to be analyzed so as to identify the larger magnitude frequency components while maintaining the interrogation period relationship of the components. As a result, data acquisition device 21 is able to identify a interrogation period having the largest local wavelet magnitude for one or more frequency slice within the transformed amplification data and correlate this to a $T_{max}$ value for the PCR amplification session associated with the amplification data. Data acquisition device 21 may then update a display based on the $T_{max}$ value.

Figure 22:
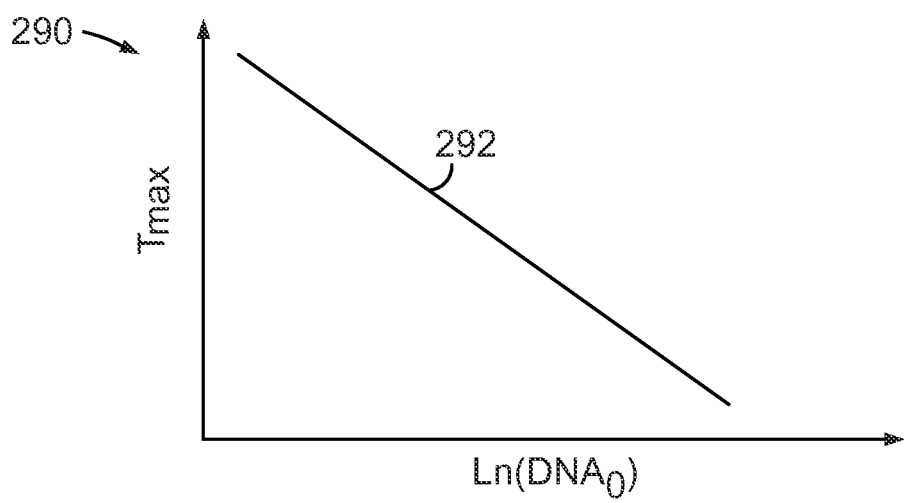
FIG. 22 is a graph illustrating a standard curve for an example nucleic acid dilution series.

FIG. 22 is a graph illustrating a standard curve for an example nucleic acid dilution series. When system 9 performs PCR on a plurality of samples including different known initial concentrations of a nucleic acid, data acquisition device 21 may generate a plot 290 including a standard curve 292 of the $T_{max}$ of the sample versus a logarithm of initial DNA concentration (DNA0), as shown in FIG. 22. The standard curve 292 may include a line fit to a plurality of (ln(DNA0), $T_{max}$) data points using linear regression or another curve fitting technique. Data acquisition device 21 may subsequently use the standard curve 292 or an equation representative of standard curve 292 to quantify an initial concentration of a nucleic acid sample having an unknown initial concentration of nucleic acid. For example, data acquisition device 21 may determine a $T_{max}$ value for the sample having an unknown initial concentration of nucleic acid. Data acquisition device 21 may then plot the $T_{max}$ value along standard curve 292 at a point corresponding to the $T_{max}$ value, or may insert the $T_{max}$ value into the equation of standard curve 292 to determine the initial concentration of nucleic acid in the sample. Data acquisition device 21 may also use the standard curve 292 to determine an efficiency of the PCR reaction. Further details relating to applying wavelet transformation to amplification data may be found in PCT Patent Application Publication No. WO2009/132,268, entitled "ANALYSIS OF NUCLEIC ACID AMPLIFICATION CURVES USING WAVELET TRANSFORMATION," the entire contents of which are incorporated by reference herein.

Figure 23:
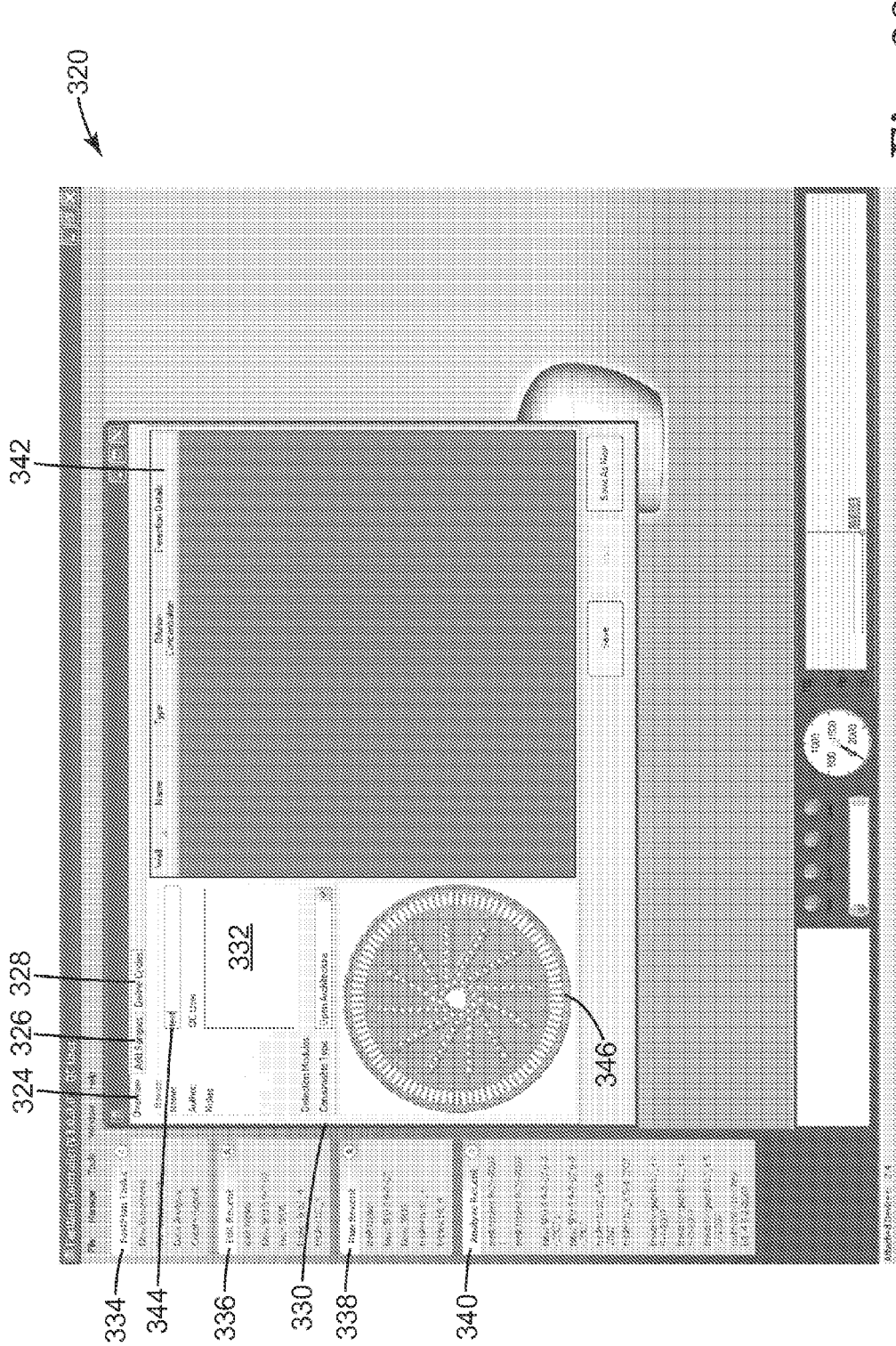
FIG. 23 is an example user interface screen presented to a user by a data amplification device.

FIG. 23 shows an exemplary user interface screen that interface module 337 may present to a user. FIG. 23 illustrates a screen 320 including a window 322 for entering parameters for the PCR reaction. The window 322 includes an "Overview" tab 324, an "Add Samples" tab 326 and a "Define Cycles" tab 328 which are linked to separate view panes within window 322. The "Overview" tab 324 is selected in screen 320. The view pane 342 linked to the "Overview" tab 324 includes a text box 332, which accepts textual entry of notes about the PCR reaction to be run, a drop-down list 330 that allows a user to enter the type of disk 13 being used, and a text box 344, which allows a user to enter a name of the test. The view pane 342 may also include a graphical display 346 of the disk 13 selected using drop-down list 330. While FIG. 23 illustrates the type of disk 13 as being selected using a drop-down list 330, in other embodiments, the type of disk 13 may be selected by another user interface element, such as, for example, a radio button, an icon, a text-box, a check box or the like.

Screen 320 also includes a plurality of navigation widgets 334, 336, 338 and 340, each including a number of hyperlinks. Tasks widget 334 includes hyperlinks that direct a user to screens for performing common tasks, such as defining a new experiment, running an experiment, analyzing data, or creating a report. Edit widget 336 includes hyperlinks that direct a user to an editing screen that allows editing of a recently defined PCR reaction parameter set. Widget 338 includes hyperlinks that direct a user to a screen that allows a user to run the currently loaded disk 13 with a recently defined PCR reaction parameter set. Widget 340 includes hyperlinks that direct a user to a screen that allows a user to analyze recently collected and saved PCR amplification data.

Figure 24:
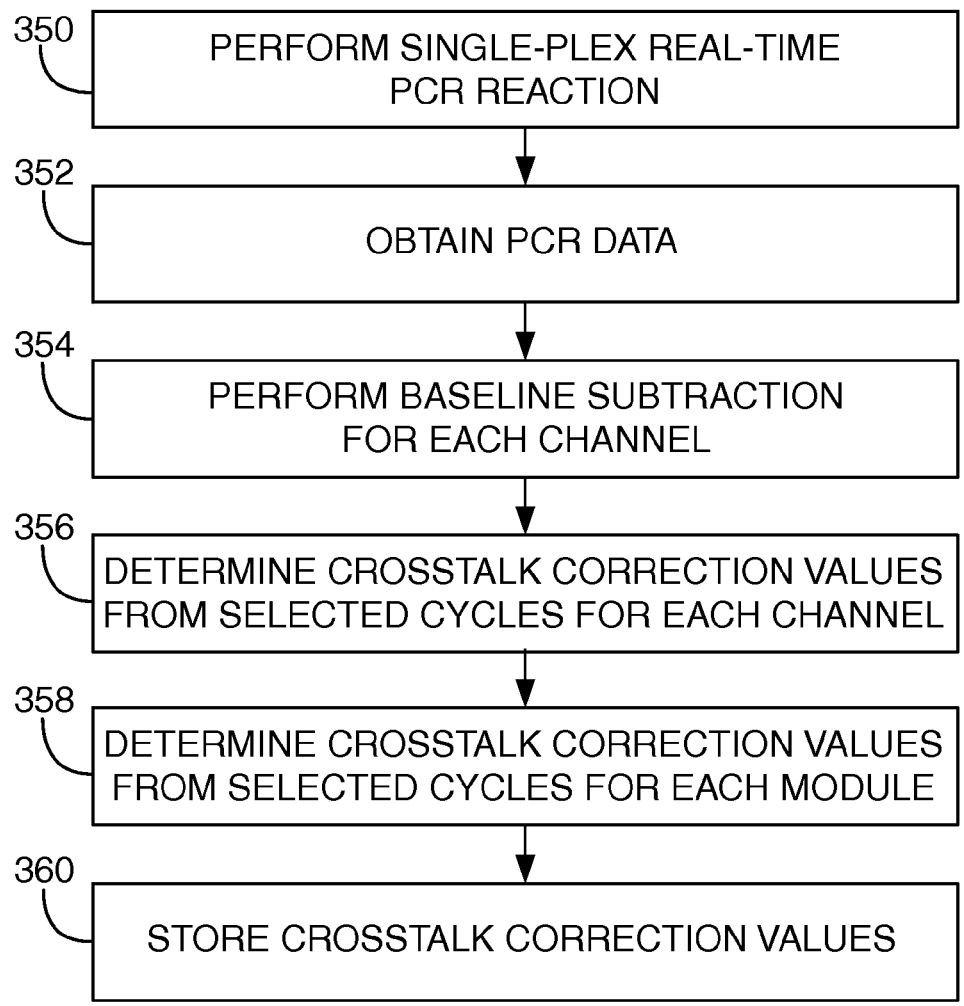
FIG. 24 is a flow diagram illustrating an example method of determining spectral crosstalk correction values for a PCR amplification system.
Figure 25:
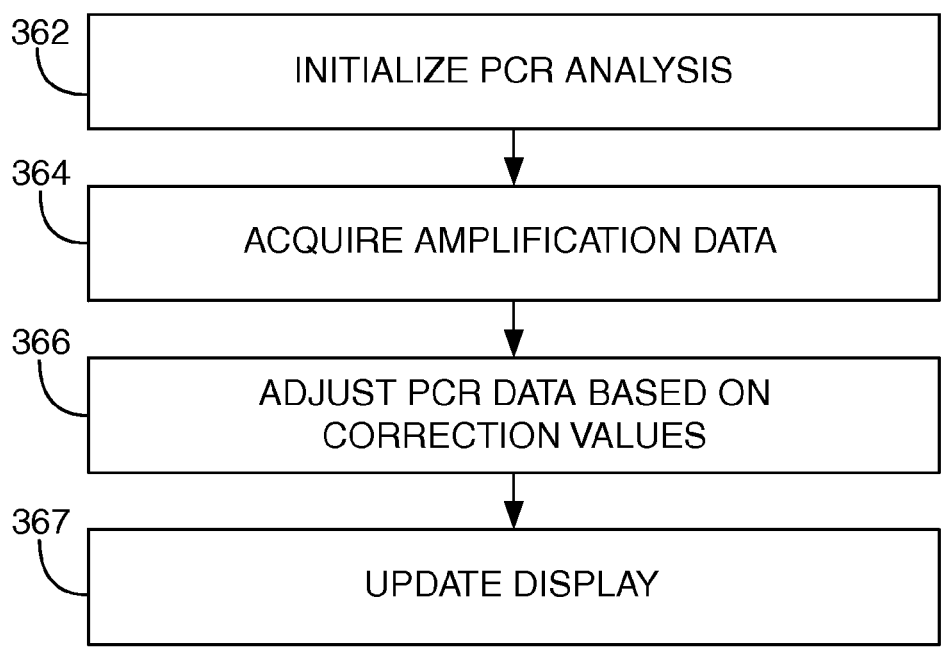
FIG. 25 is a flow diagram illustrating an example operation of a PCR amplification system.

FIG. 24 is a flowchart illustrating example operation of data acquisition device 21 (FIG. 1) in determining spectral crosstalk correction values for calibrating multiplex fluorescence detection device 10. Although described for purposes of example with respect to data acquisition device 21, the process of determining spectral crosstalk correction values may be performed by other devices, such as control unit 23 of multiplex fluorescence detection device 10, or by another device (not shown) separate from system 9. Furthermore, although described for purposes of example with respect to PCR amplification, the techniques shown in FIG. 25 are readily applicable to other techniques for nucleic acid amplification, such as transcription-mediated amplification (TMA).

A single-plex real-time PCR reaction is performed with a nucleic acid sample for each probe (e.g., dye) and corresponding module 16 of interest (350). As described above, in some embodiments, the crosstalk correction values are determined based on signals from PCR reactions performed with actual nucleic acid samples. In each of the single-plex reactions, the probe of interest is referred to as the target probe. The term "single-plex" refers to the fact that the target probe is the only probe being used in the reaction. For calibrating device 10 of FIG. 1, for example, four separate single-plex real-time PCR reactions are performed, one for each target probe corresponding to each of the four modules 16 of device 10. For each PCR reaction, a signal comprising PCR data is obtained on each channel, i.e., by each of modules 16 (352). Data acquisition device 21 performs a baseline subtraction for each channel to filter out background noise, resulting in a background-subtracted signal (354). This is denoted by Equation 1:

$$\text{signal}_{bk} = \text{signal}_i - bk_i \qquad (1),$$

where the index i corresponds to a module with a target dye, the index j corresponds to a module with a dye that is a nearest spectral neighbor to the target dye, and $bk_i$ denotes an amount attributable to background noise.

Data acquisition device 21 determines correction values $cor_i$ for every channel (356). Crosstalk correction values may be determined for each of a plurality of interrogation periods. The crosstalk correction values may be correction factors based on the nearest spectral neighbor(s). For example, the correction factors for the FAM, JOE, TxRed, and Cy5 modules are shown below:

$$Cor_{FAM} = \frac{signal_{bk,JOE}}{signal_{bk,FAM}} \qquad (2)$$

$$Cor_{JOE} = \frac{signal_{bk,FAM}}{signal_{bk,JOE}} \qquad (3)$$

$$Cor_{TxRed} = \frac{signal_{bk,Cy5}}{signal_{bk,TxRed}} \qquad (4)$$

$$Cor_{Cy5} = \frac{signal_{bk,TxRed}}{signal_{bk,Cy5}} \quad (5)$$

As illustrated by the above Equations 2-5, the nearest spectral neighbor for the FAM module is JOE, the nearest spectral neighbor for the JOE module is FAM, the nearest spectral neighbor for the TxRed module is Cy5, and the nearest spectral neighbor for the Cy5 module is TxRed. Although the above crosstalk correction values for each module includes only one factor, associated with the nearest spectral neighbor, in other embodiments or for other modules, more than one spectral neighbor may be accounted for in the correction factor for a module. A "nearest spectral neighbor" or, more broadly, a "near spectral neighbor" may be determined based on a distance from peak fluorescence of a target dye to peak fluorescence of a neighboring target dye. See, e.g., FIGS. 13-14 illustrating the peak fluorescence of various dyes. For example, neighbors with peak fluorescence separated by a distance less than a threshold distance (e.g., in nanometers) may be considered spectral neighbors, with the closest neighbor being identified as a nearest spectral neighbor. An example threshold distance may be, for example, 50 nm. Alternatively or additionally, one could determine whether to include a correction factor for a neighboring dye based on a threshold above a baseline. That is, where the signals detected by a particular module show crosstalk attributable to a different dye that exceeds a threshold amount (e.g., 10% of the baseline), the correction value for that module will include a term that factors out the crosstalk. Where the signals show crosstalk that is at a level below the threshold, the correction value may not include a term for that dye. Put another way, the correction value may be thought of as a sum of products of correction factors and signals for each channel. The correction factors, however, will be zero unless the crosstalk determined during the calibration process exceeds the threshold.

An average correction value may be determined for each channel by taking an average of the correction values obtained for each of the plurality of cycles (358). Cycles may be used occurring from, for example, 3-5 cycles after a threshold cycle Ct, and continuing on for some number of subsequent cycles. As one example, the crosstalk correction values from cycles 30-35 may be averaged. As another example, the crosstalk correction values from cycles 30-45 may be averaged. As yet another example, the crosstalk correction values from cycles 35-50 may be averaged.

The averaged crosstalk correction values for each module may be stored as parameters in memory (360). For example, the averaged crosstalk correction values for each module may be stored in database module 139 of data acquisition module 21. As another example, the averaged crosstalk correction values for each module may be stored in control unit 23 of device 10.

Each dye has a different crosstalk correction values. If modules 16 are switched out for different modules, new crosstalk correction values for the dyes to be used with the new modules are used, and such values may be determined in a similar manner to that described above and programmed into a non-volatile memory of data acquisition device 21 and/or fluorescence detection device 10.

FIG. 25 is a flowchart illustrating an exemplary method by which data acquisition device 21 collects and analyzes PCR amplification data. Although described for purposes of example with respect to PCR amplification, the techniques shown in FIG. 25 are readily applicable to other techniques for nucleic acid amplification analysis. Data acquisition device 21 initializes the PCR amplification (362). For example, data acquisition device 21 (e.g., control module 135) controls the operation of fluorescence detection device 10 according to parameters stored in database module 139 or input by a user 149 via interface module 137. The parameters may include the crosstalk correction factors determined according to the techniques described herein, such as by the method discussed in FIG. 24. In some aspects, data acquisition device 21 may be configured with the crosstalk correction values during manufacturing. The parameters may also include, for example, sample type and number, fluorescent marker type, detector wavelength, cycle number, cycle steps, cycle temperature profiles and temperature ramp rates, disk rotation speeds, fluorescence detection times, and the like.

Data acquisition device 21 initializes the PCR amplification by, for example, outputting commands to control unit 23 directing fluorescence detection device 10 to prepare for a new PCR amplification session based on the operating parameters specified by the user. In addition, data acquisition device 21 may initialize one or more files for storage of amplification curve data to be received from fluorescence detection device 10.

In response, control unit 23 acquires PCR amplification data (364) using optical modules 16 and detector 18. The control unit 23 may acquire fluorescence data for each PCR interrogation period, and may collect data for a certain length of time, such as, for example, a certain number of revolutions of disk 13, for each PCR interrogation period. Control unit 23 may integrate the fluorescence detected by detector 18 to produce a single fluorescence value for each PCR interrogation period, or may acquire and retain a plurality of fluorescence values for a single PCR interrogation period. The control unit 23 may buffer the amplification data until the end of the PCR amplification session, or may communicate the data to data acquisition device 21, which may store the amplification data in database module 139 for later amplification or may transfer the amplification data to analysis module 143 for substantially real-time amplification.

In any case, analysis module 143 of data acquisition device 21 applies the crosstalk correction values to the PCR amplification data (366). For example, to obtain a corrected signal for a module in which crosstalk detected by the module due to a dye associated with a spectral neighbor is removed, analysis module 143 may obtain a background-corrected signal for the module, and subtracts from the background signal the product of the correction value for the spectral neighbor and a signal from the nearest spectral neighbor channel. This calculation is represented by Equation 6:

$$signal_{cor,i} = signal_{bk,i} - cor_i(signal_j), \quad (6)$$

where the index i corresponds to a module with a target dye, the index j corresponds to a module with a dye that is a nearest spectral neighbor to the target dye, and $signal_{bk}$ denotes a background corrected signal. For example, for the FAM channel, which has the JOE channel as its nearest neighbor, Equation 6 would result in the following calculation:

$$signal_{cor,FAM} = signal_{bk,FAM} - cor_{FAM}(signal_{JOE}).$$

Interface module 137 updates a display based on the corrected data (367). In some embodiments, the interface module 137 may display the corrected data on a graph, as an entry in a table, or in any other suitable format. In other embodiments, interface module 137 may display a message based on the corrected data on a display of output device 36. For example, analysis module 143 may interpret the determination of a $C_t$ value to simply mean that a certain nucleic acid segment is present in the sample that has undergone PCR amplification. Interface module 137 may then display a message indicating the presence of this nucleic acid segment in the sample. Conversely, if a $C_t$ value is not determined by a given module for the sample (i.e., no amplification has occurred), analysis module 143 may interpret this to indicate that no nucleic acid with a certain sequence is present in the sample, and interface module 137 may display a corresponding message. This may be desirable in nucleic acid amplification used to determine the presence of a pathogen, for example. Based on the corrected data, the analysis module 143 may identify and interpret one or more other characteristics of amplification curves, and may present the findings to a user.

Example 2

The following example illustrates application of the spectral crosstalk compensation algorithm. A series of four single-plex quadruplicate reactions were performed in the following layout:

Wells 1-4, 500 copies cDNA template 10 micro-liter reaction volume, FAM-labeled probe only.

Wells 5-8, 500 copies of cDNA, JOE-labeled probe only.

Wells 9-12, 500 copies of cDNA, Texas Red-labeled probe only.

Wells 13-16, 3000 copies cDNA, Cy5-labeled probe only.

For simplicity and clarity, the following graphs show data from Wells 1, 5, 9, and 13.

Figure 26A:
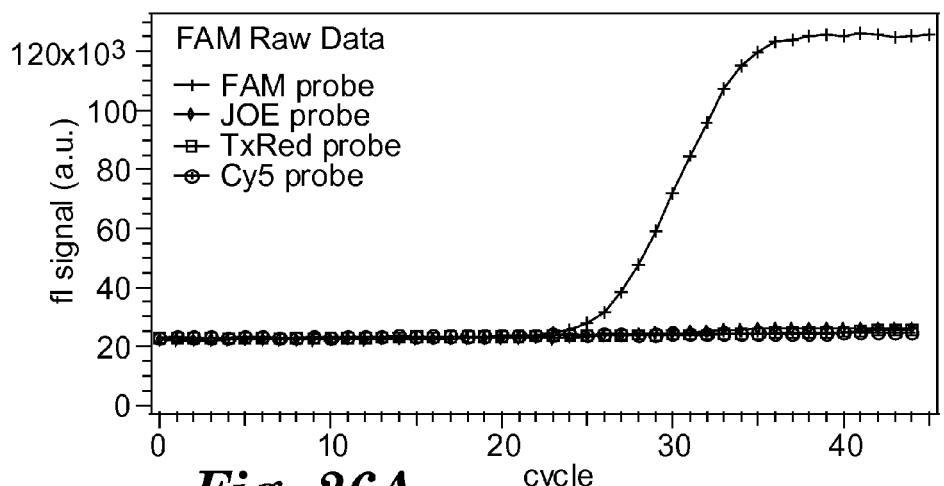
FIGS. 26A-26C are graphs illustrating amplification curves based on traces of single-plex data based on a FAM probe.
Figure 26B:
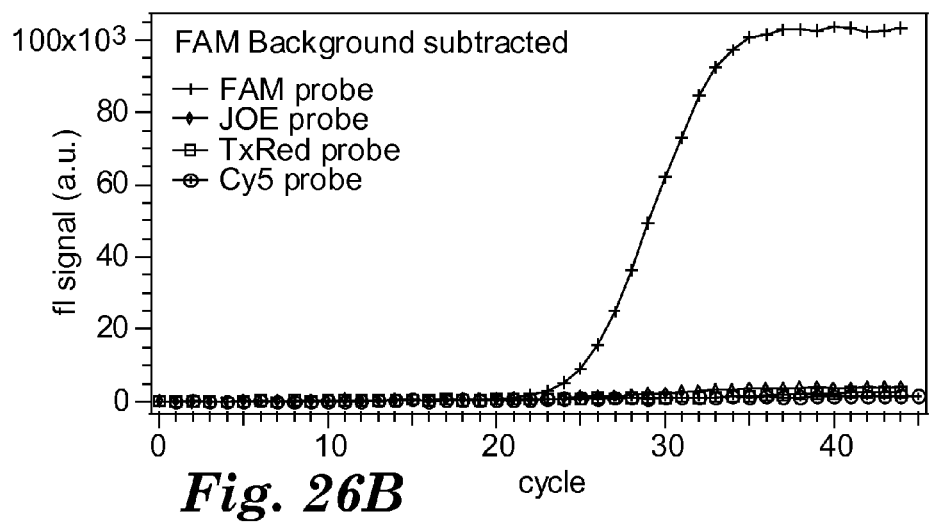
Figure 26C:
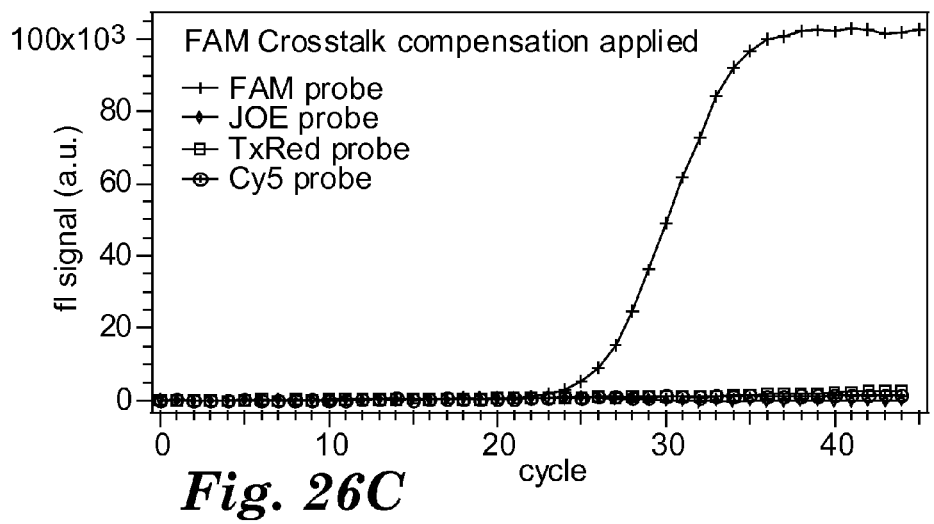

FIGS. 26A-26C are graphs illustrating amplification curves based on traces of single-plex data obtained when using a FAM probe. The amplification curves represent an intensity of a sample sensed by fluorescence versus each of a plurality of PCR interrogation periods. FIG. 26A is a graph illustrating raw data detected by a single-plex FAM channel detection in which a FAM probe is used for analysis of a nucleic acid sample.

After acquiring the single-plex data, the raw data is background-subtracted. This can be done in a number of different ways. In this example, the background for each well is calculated as the average of the data acquired during cycles 2-6 for that well. A wider range than this can be chosen, because there is no amplification signal until about cycle 25. FIG. 26B is a graph illustrating an amplification curve based on the FAM channel detection data that has been background-corrected. As compared to FIG. 26A, the data in FIG. 26B is shifted down relative to the y-axis. In accordance with the techniques described above, crosstalk correction factors are calculated, e.g., by control unit 23 of device 10, or by data acquisition device 21. The correction factors calculated in this example are: $cor_{FAM}$=0.09408; $cor_{JOE}$=0.06402; $cor_{TxRed}$=0; $cor_{Cy5}$=0.1202.

FIG. 26C is a graph illustrating an amplification curve based on FAM channel detection data that has been background-corrected and to which crosstalk correction has been applied. FIGS. 26A-26C show little to no crosstalk on the FAM channel detection data attributed to any of the probes other than the FAM probe, both before and after the correction is applied.

Figure 27A:
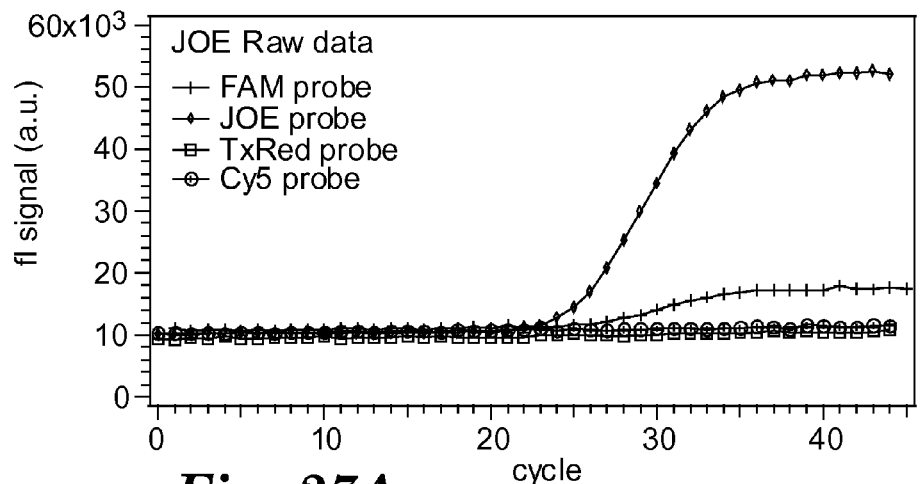
FIGS. 27A-27C are graphs illustrating amplification curves based on traces of single-plex data obtained based on a JOE probe.
Figure 27B:
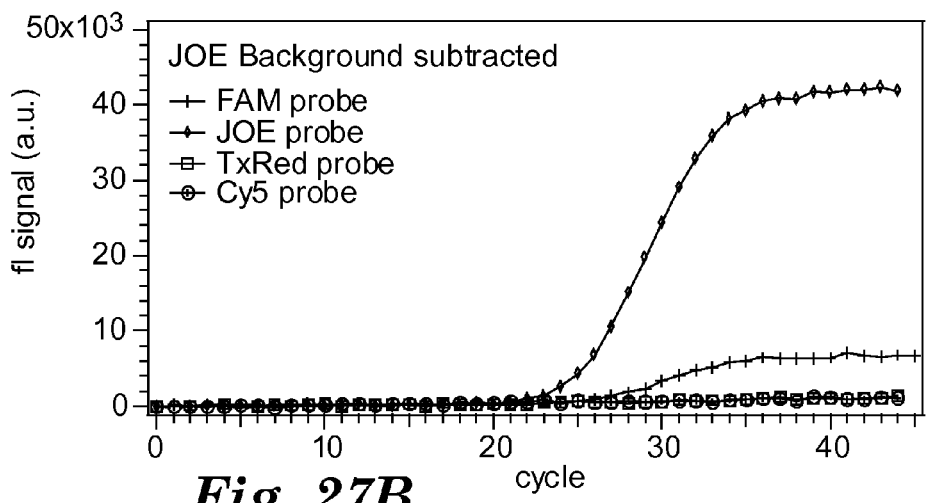
Figure 27C:
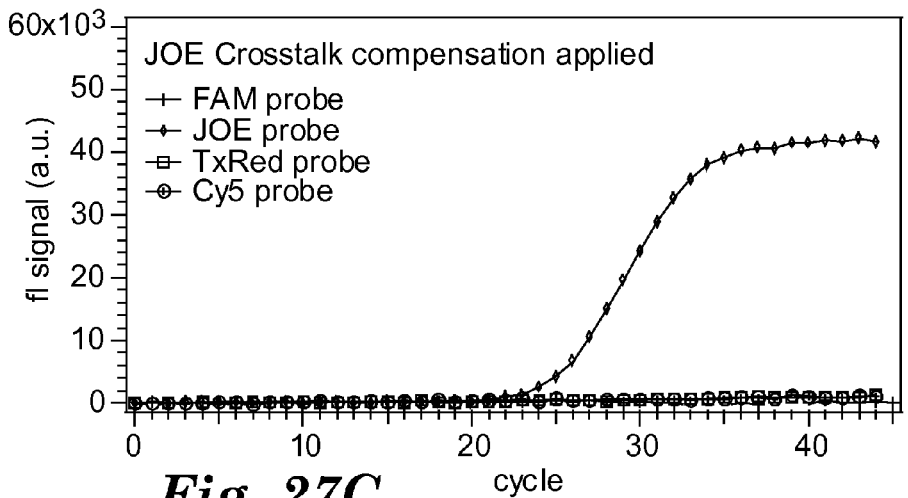

FIGS. 27A-27C are graphs illustrating amplification curves based on traces of single-plex data obtained when using a JOE probe. FIG. 27A is a graph illustrating raw data detected by a single-plex JOE channel detection in which a JOE probe is used for analysis of a nucleic acid sample. As shown in FIG. 27A, the JOE channel detection exhibits significant crosstalk attributed to the FAM labeled probe.

FIG. 27B is a graph illustrating an amplification curve based on the JOE channel detection data that has been background-corrected. As compared to FIG. 27A, the data in FIG. 27B is shifted down relative to the y-axis. From FIG. 27C, a graph illustrating an amplification curve based on JOE channel detection that has been background-corrected and to which crosstalk correction has been applied, it can be seen that application of the correction factors has reduced or eliminated the crosstalk.

Figure 28A:
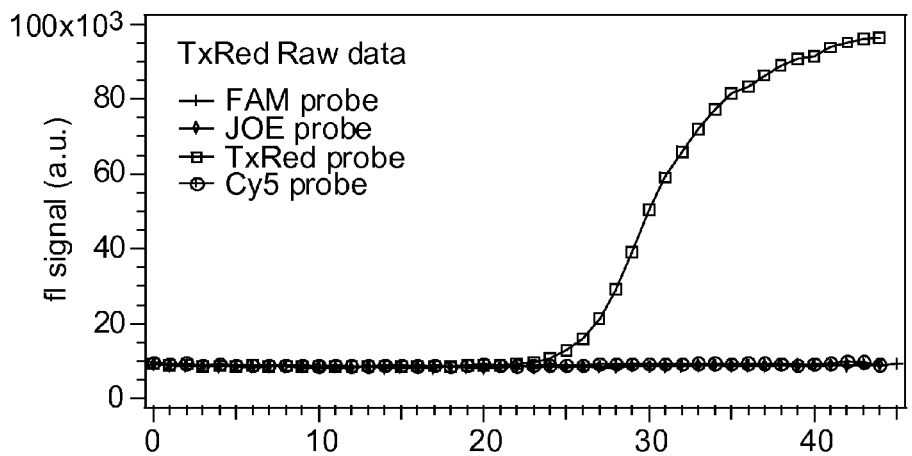
FIGS. 28A-28C are graphs illustrating amplification curves based on traces of single-plex data obtained based on a TxRed probe.
Figure 28B:
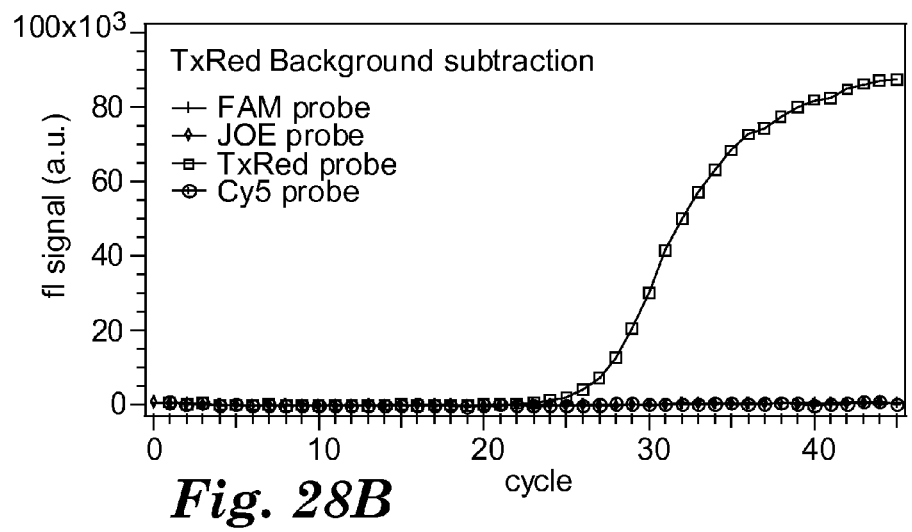
Figure 28C:
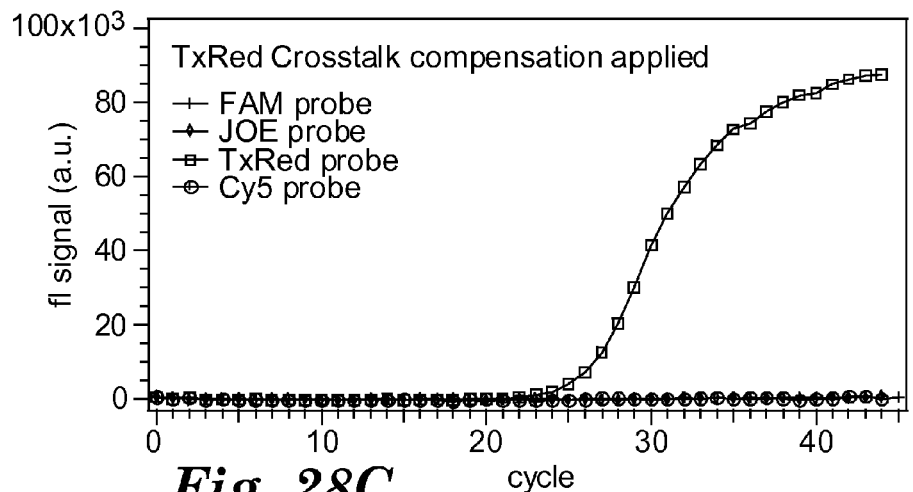

FIGS. 28A-28C are graphs illustrating amplification curves based on traces of single-plex data obtained when using a TxRed probe. FIG. 28A is a graph illustrating raw data detected by a single-plex TxRed channel detection in which a TxRed probe is used for analysis of a nucleic acid sample. FIG. 28B is a graph illustrating an amplification curve based on the TxRed channel detection data that has been background-corrected. FIG. 28C is a graph illustrating an amplification curve based on TxRed channel detection data that has been background-corrected and to which crosstalk correction has been applied. FIG. 28A-28C show little to no crosstalk on TxRed channel detection due to the probes other than the TxRed labeled probe.

Figure 29A:
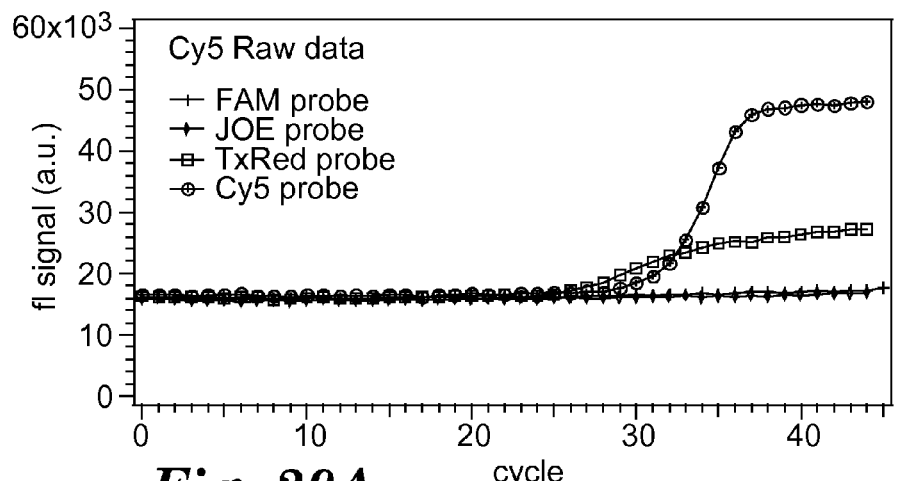
FIGS. 29A-29C are graphs illustrating amplification curves based on traces of single-plex data obtained based on a Cy5 probe.
Figure 29B:
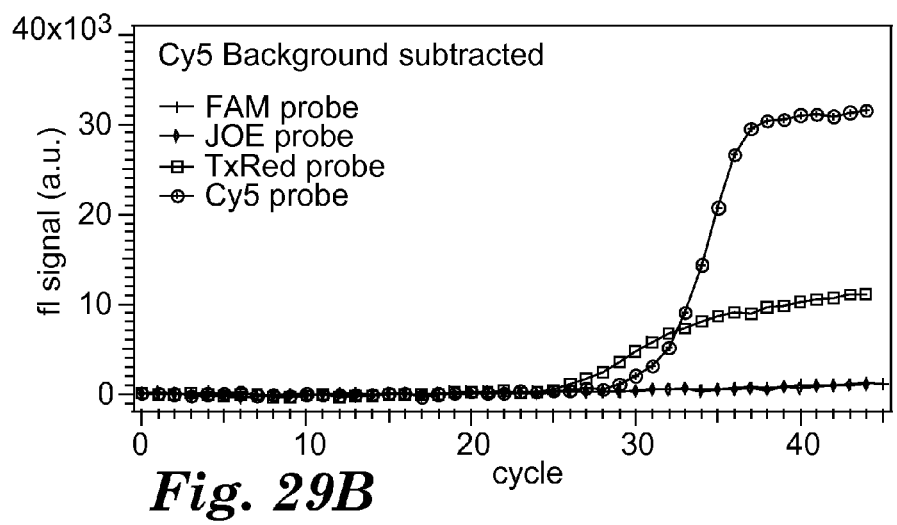
Figure 29C:
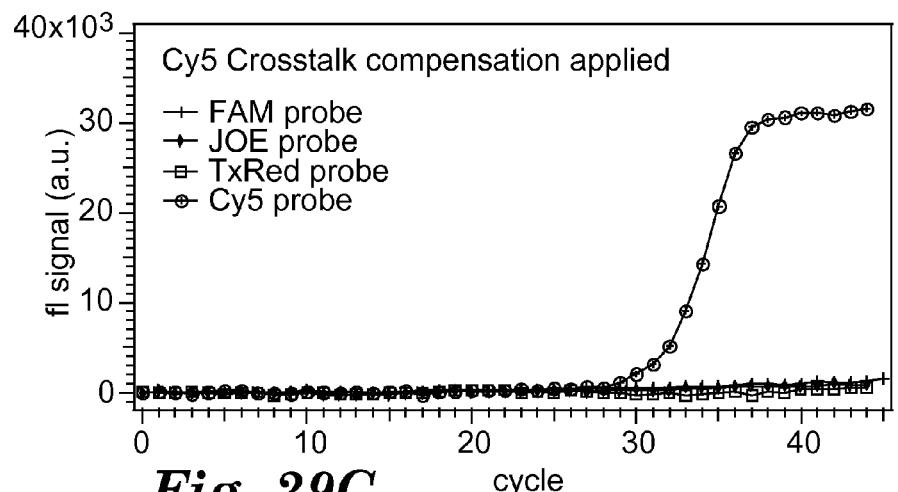

FIGS. 29A-29C are graphs illustrating amplification curves based on traces of single-plex data obtained when using a Cy5 probe. FIG. 29A is a graph illustrating raw data detected by a single-plex Cy5 channel detection in which a Cy5 probe is used for analysis of a nucleic acid sample. FIG. 29B is a graph illustrating an amplification curve based on the Cy5 channel detection data that has been background-corrected. FIG. 29C is a graph illustrating an amplification curve based on Cy5 channel detection data that has been background-corrected and to which crosstalk correction has been applied. As shown in FIGS. 29A-29C, the Cy5 channel detection exhibits significant crosstalk attributed to the Texas Red labeled probe. From FIG. 29C, it can be seen that application of the correction factors has reduced or eliminated the crosstalk attributable to a TxRed probe on the Cy5 channel.

The effectiveness of the algorithm may be demonstrated, for example, by comparing the threshold cycle Ct of the data before and after the spectral crosstalk compensation has been applied. The Ct may be identified by applying a manual or automatic threshold technique to identify a cycle corresponding to a point within a growth period of the amplification data. The manual threshold technique relies on a user to set threshold fluorescence intensity. An analysis module 143 of data acquisition device 21 (FIG. 10) then determines when the amplification data crosses this threshold and returns the cycle at which this occurs as the $C_t$ value.

If the automatic threshold technique is selected, analysis module 143 automatically determines threshold fluorescence intensity. For example, the analysis module 143 may determine an average and a standard deviation of the fluorescence signal in the baseline region of the amplification curve. The analysis module 143 may then set the threshold as a certain number of standard deviations above the average baseline fluorescence signal, such as, for example, five standard deviations above the average fluorescence signal. The threshold techniques are described in further detail in U.S. Patent Application Publication No. 2003/0044826, entitled "AUTOMATIC THRESHOLD SETTING FOR QUANTITATIVE POLYMERASE CHAIN REACTION," which is incorporated herein by reference in its entirety.

In some embodiments, analysis module 143 may allow user 149 to choose a Fourier transform technique or a double sigmoid fit technique to determine a cycle corresponding to a point within a growth period of the amplification data. The Fourier transform technique is described in detail in U.S. Patent Application Publication No. 2006/0286587, entitled "METHODS FOR QUANTITATIVE ANALYSIS OF A NUCLEIC ACID AMPLIFICATION REACTION," and the double sigmoid fit technique is described in detail in U.S. Patent Application Publication No. 2007/0143385, entitled "PCR ELBOW DETERMINATION BY USE OF A DOUBLE SIGMOID FUNCTION CURVE FIT WITH THE LEVENBERG-MARQUARDT ALGORITHM AND NORMALIZATION," which are incorporated herein by reference in its entirety. In other embodiments, analysis module 143 may also allow user 149 to choose a derivative technique as a different mechanism for determining a cycle corresponding to a point within a growth period of the amplification data. In the derivative technique, the analysis module 143 may compute an nth order derivative of the amplification data, determine a maximum, minimum, or zero value of the nth order derivative, and output the PCR cycle at which this value of the derivative is found as the Ct value. The derivative techniques are described in further detail in U.S. Patent Application Publication No. 2002/0028452, entitled "METHOD FOR QUANTIFICATION OF AN ANALYTE," which is incorporated herein by reference in its entirety.

Table 2 below shows the threshold cycles Ct calculated using the derivative method on the raw data obtained in this example. It would be expected that there should only be Ct reported in wells 1-4 for the FAM probe, wells 5-8 for the JOE probe, wells 9-12 for the Texas Red probe, and wells 13-16 for the Cy5 probe. However, the shaded portions of Table 2 (JOE module, wells 1-4 and Cy5 module, wells 9-12) correspond to false positive indications due to the crosstalk from nearest spectral neighbors.

TABLE 2

| Well | FAM Ct | JOE Ct | TxRed Ct | Cy5 Ct |
|---|---|---|---|---|
| 1 | 26.501 | 26.322 | | |
| 2 | 26.487 | 26.135 | | |
| 3 | 26.492 | 26.557 | | |
| 4 | 26.504 | 26.495 | | |
| 5 | | 26.174 | | |
| 6 | | 26.134 | | |
| 7 | | 26.604 | | |
| 8 | | 26.543 | | |
| 9 | | | 27.272 | 26.930 |
| 10 | | | 27.428 | 27.142 |
| 11 | | | 27.353 | 27.377 |
| 12 | | | 27.455 | 27.256 |
| 13 | | | | 32.540 |
| 14 | | | | 32.198 |
| 15 | | | | 32.486 |
| 16 | | | | 32.225 |

Table 3 below shows the threshold cycles Ct after the spectral crosstalk compensation techniques have been applied. As shown by Table 3, any false positives have been filtered out.

TABLE 3

| Well | FAM Ct | JOE Ct | TxRed Ct | Cy5 Ct |
|---|---|---|---|---|
| 1 | 26.502 | | | |
| 2 | 26.488 | | | |
| 3 | 26.492 | | | |
| 4 | 26.504 | | | |
| 5 | | 26.180 | | |
| 6 | | 26.131 | | |
| 7 | | 26.603 | | |
| 8 | | 26.540 | | |
| 9 | | | 27.272 | |
| 10 | | | 27.428 | |
| 11 | | | 27.353 | |
| 12 | | | 27.455 | |
| 13 | | | | 32.539 |
| 14 | | | | 32.197 |
| 15 | | | | 32.484 |
| 16 | | | | 32.232 |

Table 4 below shows the threshold cycles Ct's calculated using the wavelet method on the raw data obtained in this example. Similar to the example above, it would be expected that there should only be Ct reported in wells 1-4 for the FAM probe, wells 5-8 for the JOE probe, wells 9-12 for the Texas Red probe, and wells 13-16 for the Cy5 probe. However, the shaded portions of Table 2 (JOE module, wells 1-4 and Cy5 module, wells 9-12) correspond to false positive indications due to the crosstalk from nearest spectral neighbors.

TABLE 4

| Well | FAM Ct | JOE Ct | TxRed Ct | Cy5 Ct |
|---|---|---|---|---|
| 1 | 25.22 | 25.25 | | |
| 2 | 25.21 | 25.02 | | |
| 3 | 25.28 | 25.14 | | |
| 4 | 25.28 | 25.05 | | |
| 5 | | 25.20 | | |
| 6 | | 25.58 | | |
| 7 | | 25.78 | | |
| 8 | | 25.85 | | |
| 9 | | | 25.83 | 26.03 |
| 10 | | | 26.15 | 26.28 |
| 11 | | | 25.97 | 26.18 |
| 12 | | | 26.25 | 26.29 |
| 13 | | | | 30.15 |
| 14 | | | | 29.72 |
| 15 | | | | 30.09 |
| 16 | | | | 29.78 |

Table 5 below shows Ct's after the spectral crosstalk compensation techniques have been applied to the wavelet analysis. As shown by Table 5, any false positives have been filtered out.

TABLE 5

| Well | FAM Ct | JOE Ct | TxRed Ct | Cy5 Ct |
|---|---|---|---|---|
| 1 | 25.22 | | | |
| 2 | 25.21 | | | |
| 3 | 25.29 | | | |
| 4 | 25.28 | | | |
| 5 | | 25.20 | | |
| 6 | | 25.58 | | |
| 7 | | 25.78 | | |
| 8 | | 25.85 | | |
| 9 | | | 25.83 | |
| 10 | | | 26.15 | |
| 11 | | | 25.97 | |
| 12 | | | 26.25 | |

TABLE 5-continued

| Well | FAM Ct | JOE Ct | TxRed Ct | Cy5 Ct |
|---|---|---|---|---|
| 13 | | | | 30.15 |
| 14 | | | | 29.72 |
| 15 | | | | 30.08 |
| 16 | | | | 29.79 |

Figure 30:
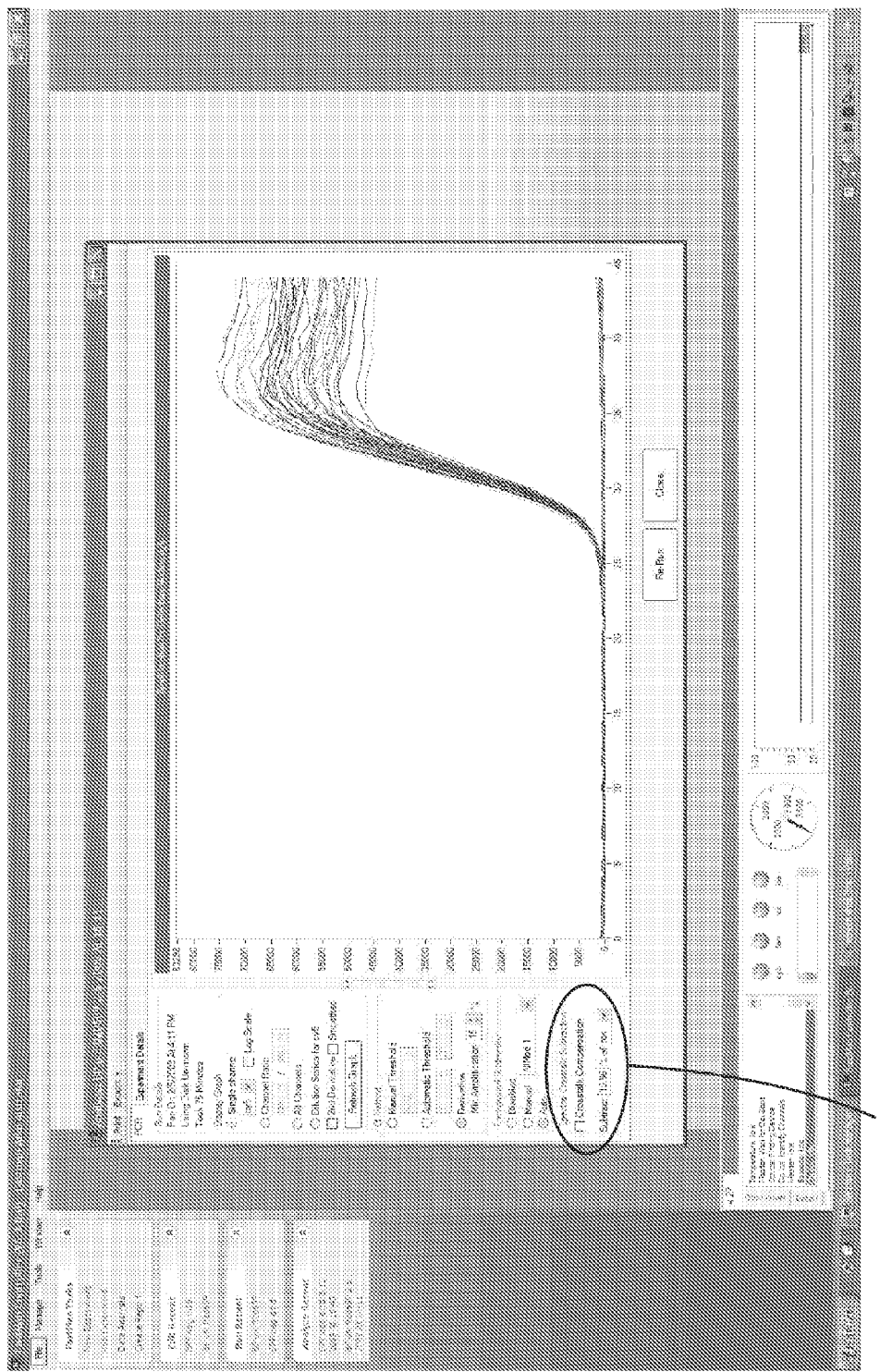
FIG. 30 is an example user interface screen presented to a user by a data acquisition device.

FIG. 30 is an example user interface screen presented to a user by a data acquisition device. The screen includes a Crosstalk Compensation control portion 370. In the example of FIG. 30, the control portion 370 allows a user to turn the crosstalk compensation feature on or off. In some embodiments, access to the Crosstalk Compensation control portion 370 may be user-specific based on user privileges. For example, in some embodiments, a user must have administrator status to be able to turn the crosstalk compensation feature on or off, and if the user does not have administrator status the user is locked out from adjusting crosstalk compensation parameters. In some embodiments, a user having a particular status may also be able to configure or change the compensation factors. For example, a different user interface screen may be presented that provides a management interface to allow the user to select parameters for one or more instruments, including the modules 16 of device 10. For example, such a management interface may present a matrix table that allows the user to input coefficients that control the crosstalk compensation.

Various embodiments of the invention have been described. These and other embodiments are within the scope of the following claims.

The invention claimed is:

1. A method comprising:
a calibration process comprising
performing a nucleic acid amplification of a nucleic acid sample using a plurality of detection probes, wherein the nucleic acid amplification occurs over a plurality of interrogation periods; wherein performing the nucleic acid amplification in the calibration process comprises applying the corresponding detection probe to the nucleic acid sample; scanning each of a plurality of channels to detect amplification data on the channels attributable to the corresponding detection probe, wherein one of the plurality of channels is configured to detect amplification data due to the corresponding detection probe, and wherein the other ones of the plurality of channels are not configured to detect amplification data due to the corresponding detection probe; wherein determining a plurality of crosstalk correction values comprises determining each crosstalk correction value based on the identified amplification data associated with one of the plurality of channels not configured to detect amplification data due to the corresponding detection probe;
from the nucleic acid amplification, acquiring amplification data that indicates an amount of nucleic acid present for each of the plurality of interrogation periods; and
based on the amplification data, determining the plurality of crosstalk correction values, each crosstalk correction value associated with a spectral neighbor to a corresponding detection probe to reduce spectral crosstalk from the spectral neighbor;
the method further comprising a nucleic acid amplification analysis comprising
applying the crosstalk correction value obtained from the calibration process to amplification data collected from nucleic acid amplification of nucleic acid samples,
wherein each of the plurality of crosstalk correction values is the ratio of a signal detected for the spectral neighbor to the signal detected for the amplification data of the corresponding detection probe, and
wherein applying the crosstalk correction value to the amplification data comprises subtracting a product of the crosstalk correction value and amplification data of the spectral neighbor from the amplification data of the corresponding detection probe.

2. The method of claim 1, wherein each spectral neighbor is a nearest spectral neighbor and further comprising:
generating an amplification curve from the amplification data, the amplification curve representing growth of the nucleic acid sample versus interrogation period; and
prior to determining the crosstalk correction value associated with the nearest spectral neighbor, determining the nearest spectral neighbor based on a threshold distance between a peak fluorescence for the channel configured to detect amplification data due to the corresponding detection probe and a peak fluorescence for the nearest spectral neighbor.

3. The method of claim 1, wherein the nucleic acid amplification uses a plurality of optical modules each associated with a different channel for optical detection of different fluorescent dyes.

4. The method of claim 1, further comprising calibrating a nucleic acid amplification device that performs the nucleic acid amplification with the determined crosstalk correction value.

5. The method of claim 1, further comprising:
subtracting a background signal from the amplification data detected by the probe to obtain background-corrected signal for the probe;
calculating a ratio of a signal for the nearest spectral neighbor to the background-corrected signal for the corresponding detection probe for each of a plurality of selected interrogation periods;
averaging the calculated ratios across the plurality of selected interrogation periods; and
identifying the average of the calculated ratios as the crosstalk correction value for the probe.

6. The method of claim 5, wherein the selected interrogation periods comprise interrogation periods selected from those interrogation periods occurring after a threshold cycle $C_t$.

7. A method comprising:
performing a multiplex nucleic acid amplification of a nucleic acid sample in a nucleic acid amplification analysis, wherein the multiplex nucleic acid amplification comprises a plurality of interrogation periods; wherein performing the nucleic acid amplification in the calibration process comprises applying the corresponding detection probe to the nucleic acid sample; scanning each of a plurality of channels to detect amplification data on the channels attributable to the corresponding detection probe, wherein one of the plurality of channels is configured to detect amplification data due to the corresponding detection probe, and wherein the other ones of the plurality of channels are not configured to detect amplification data due to the corresponding detection probe; wherein determining a crosstalk correction value comprises determining the crosstalk correction value based on the identified amplification data associated with one of the plurality of channels not configured to detect amplification data due to the corresponding detection probe;

from the nucleic acid amplification, acquiring amplification data that indicates an amount of nucleic acid present for each of the plurality of interrogation periods;

applying the crosstalk correction value to the amplification data to generate modified amplification data in which spectral crosstalk signals from a spectral neighbor are reduced, wherein applying the crosstalk correction value to the amplification data comprises subtracting a product of the crosstalk correction value and amplification data of the spectral neighbor from the amplification data of the detection probe, wherein the crosstalk correction value is derived based on multiplex nucleic acid amplification of a second nucleic acid sample in a calibration process; and displaying the modified amplification data, wherein the crosstalk correction value is the ratio of a signal detected for the spectral neighbor to the signal detected for the amplification data of the detection probe.

8. The method of claim 7, wherein applying the crosstalk correction value to the amplification data comprises:

subtracting a background signal from the amplification data to obtain a background-corrected signal; and subtracting, from the background-corrected signal, a product of the crosstalk correction value and the signal detected by the spectral neighbor.

9. The method of claim 8, wherein the crosstalk correction value is determined by calculating a ratio of a signal for the spectral neighbor to a background-corrected signal for the probe for each of a plurality of selected interrogation periods, and averaging the calculated ratios across the plurality of selected interrogation periods.

10. The method of claim 7, wherein applying the crosstalk correction value comprises applying the crosstalk correction value with a multiplex nucleic acid amplification device that performs the multiplex nucleic acid amplification.

11. The method of claim 7, wherein applying the crosstalk correction value comprises applying the crosstalk correction value with an amplification device in communication with a multiplex nucleic acid amplification device that performs the multiplex nucleic acid amplification.

12. The method of claim 7, wherein the nucleic acid amplification uses a plurality of optical modules each associated with a different channel for optical detection of different fluorescent dyes.

13. A detection device comprising:

a motor to rotate a disk having a plurality of process chambers each holding a respective sample and one or more fluorescent dyes;

a plurality of optical modules, and a housing having a plurality of locations adapted to receive the optical modules;

wherein each of the plurality of optical modules includes an optical channel having a light source selected for a different one of the dyes and a lens to capture fluorescent light emitted from the disk;

a data acquisition device coupled to the detection device, wherein the data acquisition device is configured to apply a crosstalk correction value for each of the plurality of optical modules in a nucleic acid amplification analysis to reduce spectral crosstalk associated with a spectral neighbor for that optical module, wherein applying the crosstalk correction value comprises subtracting a product of the crosstalk correction value and amplification data of the spectral neighbor from the amplification data of the detection probe, wherein the crosstalk correction value is derived in a calibration process by performing an analysis based on amplification data from a nucleic acid amplification of a nucleic acid sample using a detection probe, wherein performing the nucleic acid amplification in the calibration process comprises applying the corresponding detection probe to the nucleic acid sample; and a scanner for scanning each of a plurality of channels to detect amplification data on the channels attributable to the corresponding detection probe, wherein one of the plurality of channels is configured to detect amplification data due to the corresponding detection probe, and wherein the other ones of the plurality of channels are not configured to detect amplification data due to the corresponding detection probe; wherein determining the plurality of crosstalk correction values comprises determining each crosstalk correction value based on the identified amplification data associated with one of the plurality of channels not configured to detect amplification data due to the corresponding detection probe;

wherein the nucleic acid amplification occurs over a plurality of interrogation periods, and wherein the analysis comprises acquiring the amplification data that indicates an amount of nucleic acid present for each of the plurality of interrogation periods, and determining a crosstalk correction value associated with the spectral neighbor based on the amplification data, wherein the crosstalk correction value is the ratio of a signal detected for the spectral neighbor to the signal detected for the amplification data of the detection probe.

14. A detection device having one or more processors comprising:

a motor to rotate a disk having a plurality of process chambers each holding a respective sample and one or more fluorescent dyes;

a plurality of optical modules;

a housing having a plurality of locations adapted to receive the optical modules, wherein each of the optical modules includes an optical channel having a light source selected for a different one of the dyes and a lens to capture fluorescent light emitted from the disk;

a control unit executing on the one or more processors, wherein the control unit is configured to apply crosstalk correction values for each of the plurality of optical modules in a nucleic acid amplification analysis to reduce spectral crosstalk associated with spectral neighbors for that optical module, wherein applying the crosstalk correction values comprises subtracting a product of the crosstalk correction value and amplification data of the one of the spectral neighbors from the amplification data of the detection probe, wherein the crosstalk correction values are derived in a calibration process by performing an analysis based on amplification data from a nucleic acid amplification of a nucleic acid sample using a detection probe, wherein performing the nucleic acid amplification in the calibration process comprises applying the corresponding detection probe to the nucleic acid sample; and a scanner for scanning each of a plurality of channels to detect amplification data on the channels attributable to the corresponding detection probe, wherein one of the plurality of channels is configured to detect amplification data due to the corresponding detection probe, and wherein the other ones of the plurality of channels are not configured to detect amplification data due to the corresponding detection probe; wherein determining the plurality of crosstalk correction values comprises determining each crosstalk correction value based on the identified amplification data associated with one of the plurality of channels not configured to detect amplification data due to the corresponding detection probe;

wherein the nucleic acid amplification occurs over a plurality of interrogation periods, and wherein the analysis comprises acquiring the amplification data that indicates an amount of nucleic acid present for each of the plurality of interrogation periods, and determining a crosstalk correction value associated with one of the spectral neighbors based on the amplification data, wherein the crosstalk correction value is the ratio of a signal detected for the spectral neighbor to the signal detected for the amplification data of the detection probe.

15. A device having one or more processors comprising:

a control module executing on the one or more processors and configured to initialize a nucleic acid amplification of a first nucleic acid sample and receive first amplification data that indicates an amount of nucleic acid present for each of a first plurality of interrogation periods; wherein performing the nucleic acid amplification in the calibration process comprises applying the corresponding detection probe to the nucleic acid sample; and a scanner for scanning each of a plurality of channels to detect amplification data on the channels attributable to the corresponding detection probe, wherein one of the plurality of channels is configured to detect amplification data due to the corresponding detection probe, and wherein the other ones of the plurality of channels are not configured to detect amplification data due to the corresponding detection probe; wherein determining a crosstalk correction value comprises determining the crosstalk correction value based on the identified amplification data associated with one of the plurality of channels not configured to detect amplification data due to the corresponding detection probe;

an analysis module executing on the one or more processors and configured to apply the crosstalk correction value for an optical module to obtain corrected amplification data having reduced spectral crosstalk associated with a spectral neighbor for that optical module, wherein the crosstalk correction value is derived in a calibration process by performing an analysis based on second amplification data from a nucleic acid amplification of a second nucleic acid sample using a detection probe, wherein the nucleic acid amplification occurs over a second plurality of interrogation periods, and wherein the analysis comprises acquiring the second amplification data that indicates an amount of nucleic acid present for each of the second plurality of interrogation periods, and determining the crosstalk correction value associated with the spectral neighbor based on the second amplification data; and an interface module executing on the one or more processors and configured to update a display based on the corrected amplification data, wherein the crosstalk correction value is the ratio of a signal detected for the spectral neighbor to the signal detected for the amplification data of the detection probe, and wherein applying the crosstalk correction value comprises subtracting a product of the crosstalk correction value and amplification data of the spectral neighbor from the amplification data of the detection probe.

16. A method comprising:

a calibration process comprising performing a polymerase chain reaction (PCR) amplification of a nucleic acid sample using a detection probe, wherein the PCR amplification occurs over a plurality of PCR interrogation periods; wherein performing the nucleic acid amplification in the calibration process comprises applying the corresponding detection probe to the nucleic acid sample; scanning each of a plurality of channels to detect amplification data on the channels attributable to the corresponding detection probe, wherein one of the plurality of channels is configured to detect amplification data due to the corresponding detection probe, and wherein the other ones of the plurality of channels are not configured to detect amplification data due to the corresponding detection probe; wherein determining a crosstalk correction value comprises determining the crosstalk correction value based on the identified amplification data associated with one of the plurality of channels not configured to detect amplification data due to the corresponding detection probe;

from the PCR amplification, acquiring amplification data that indicates an amount of nucleic acid present for each of the plurality of PCR interrogation periods; and based on the amplification data, determining the crosstalk correction value associated with a spectral neighbor to the detection probe to reduce spectral crosstalk from the spectral neighbor;

the method further comprising PCR amplification analysis including applying the crosstalk correction value obtained from the calibration process to amplification data collected from PCR amplification of nucleic acid samples, wherein the crosstalk correction value is the ratio of a signal detected for the spectral neighbor to the signal detected for the amplification data of the detection probe, and wherein applying the crosstalk correction value to the amplification data comprises subtracting a product of the crosstalk correction value and amplification data of the spectral neighbor from the amplification data of the detection probe.

17. The method of claim 16, wherein performing the PCR amplification comprises applying the detection probe to the nucleic acid sample; and scanning each of a plurality of channels to detect amplification data on the channels attributable to the detection probe, wherein one of the plurality of channels is configured to detect amplification data due to the detection probe, and wherein the other ones of the plurality of channels are not configured to detect amplification data due to the detection probe;

wherein determining the crosstalk correction value comprises determining the crosstalk correction value based on the identified amplification data associated with one of the plurality of channels not configured to detect amplification data due to the detection probe.

18. A method comprising:

a calibration process comprising performing a single-plex polymerase chain reaction (PCR) amplification of a nucleic acid sample using a detection probe, wherein the single-plex PCR amplification occurs over a plurality of PCR interrogation periods; wherein performing the nucleic acid amplification in the calibration process comprises applying the corresponding detection probe to the nucleic acid sample; scanning each of a plurality of channels to detect amplification data on the channels attributable to the corresponding detection probe, wherein one of the plurality of channels is configured to detect amplification data due to the corresponding detection probe, and wherein the other ones of the plurality of channels are not configured to detect amplification data due to the corresponding detection probe; wherein determining a crosstalk correction value comprises determining the crosstalk correction value based on the identified amplification data associated with one of the plurality of channels not configured to detect amplification data due to the corresponding detection probe;

from the PCR amplification, acquiring amplification data that indicates an amount of nucleic acid present for each of the plurality of PCR interrogation periods; and based on the amplification data, determining the crosstalk correction value associated with a nearest spectral neighbor to the probe to reduce spectral crosstalk from the nearest spectral neighbor;

the method further comprising PCR amplification analysis including applying the crosstalk correction value obtained from the calibration process to amplification data collected from multiplex PCR amplification of nucleic acid samples, wherein the crosstalk correction value is the ratio of a signal detected for the nearest spectral neighbor to the signal detected for the amplification data of the detection probe, and wherein applying the crosstalk correction value to the amplification data comprises subtracting a product of the crosstalk correction value and amplification data of the nearest spectral neighbor from the amplification data of the detection probe.

* * * * *